(12) United States Patent
Seul

(10) Patent No.: US 9,428,799 B2
(45) Date of Patent: *Aug. 30, 2016

(54) METHOD FOR DETERMINING AN ALLELE PROFILE OF NUCLEIC ACID

(75) Inventor: Michael Seul, Basking Ridge, NJ (US)

(73) Assignee: Bioinventors & Entrepreneurs Network LLC, Warren, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/190,147

(22) Filed: Jul. 25, 2011

(65) Prior Publication Data

US 2013/0029857 A1  Jan. 31, 2013

(51) Int. Cl.
*G01N 33/48* (2006.01)
*C12Q 1/68* (2006.01)
*G06F 19/20* (2011.01)

(52) U.S. Cl.
CPC ............. *C12Q 1/6858* (2013.01); *G06F 19/20* (2013.01)

(58) Field of Classification Search
CPC ....................................... G06F 19/20
USPC .......................................... 702/19
See application file for complete search history.

(56) References Cited

U.S. PATENT DOCUMENTS

| | | | |
|---|---|---|---|
| 5,144,139 A | 9/1992 | Hillman et al. | |
| 6,114,179 A | 9/2000 | Lapierre et al. | |
| 6,352,828 B1 | 3/2002 | Brenner | |
| 7,081,339 B2 | 7/2006 | Slepnev | |
| 7,083,914 B2 | 8/2006 | Seul et al. | |
| 7,312,034 B2 | 12/2007 | Virgos et al. | |
| 7,368,246 B2 | 5/2008 | Slepnev et al. | |
| 7,387,887 B2 | 6/2008 | Wittwer et al. | |
| 7,445,893 B2 | 11/2008 | Slepnev | |
| 7,456,281 B2 | 11/2008 | Dujols | |
| 7,498,054 B2 | 3/2009 | Banerjee et al. | |
| 7,550,266 B2 | 6/2009 | Slepnev | |
| 7,635,565 B2 * | 12/2009 | Hashmi et al. ............... | 435/6.12 |
| 7,635,566 B2 * | 12/2009 | Brenner ....................... | 435/6.18 |
| 7,858,307 B2 | 12/2010 | Ho | |
| 7,871,770 B2 | 1/2011 | Ho | |
| 8,021,842 B2 * | 9/2011 | Brenner ....................... | 435/6.11 |
| 2005/0147998 A1 | 7/2005 | White et al. | |
| 2006/0269932 A1 | 11/2006 | Slepnev et al. | |
| 2007/0065864 A1 | 3/2007 | Korzheva et al. | |
| 2007/0072223 A1 | 3/2007 | Slepnev | |
| 2007/0077582 A1 | 4/2007 | Slepnev | |
| 2009/0075274 A1 | 3/2009 | Slepnev et al. | |
| 2009/0136951 A1 | 5/2009 | Hart et al. | |

FOREIGN PATENT DOCUMENTS

WO      WO 0131056       3/2001

OTHER PUBLICATIONS

Hashmi et al., "A Flexible Array Format for Large-Scale, Rapid Blood Group DNA Typing", Transfusion, vol. 45, May 2005.*

'Blood Grouping Reagent Anti-D' product information, Micro Typing Systems Inc. [online], [retrieved on Apr. 11, 2011]. Retrieved from the California Blood Bank Society website using the Internet <URL: http://www.cbbsweb.org/enf/attachments/mts_dmonopi.pdf>.
Bosse, Yohan et al., "Identification of susceptibility genes for complex diseasesusing pooling-based genome-wide association scans," Jan. 29, 2009, Journal of Human Genetics, 125. pp. 305-318.
Cardoso et al, 1998 "Mini-pool screening by nucleic acid testing for hepatitis B virus, hepatitis C virus and HIV: preliminary results," Transfusion, 38(10): 905-907.
Chattopadhyay, P.K., et al., 2006, "Quantum dot semiconductor nanoctystals for immunophenotyping by polychromatic flow cytometry," Nat Med. 12(8): 972-7. Epub Jul. 23, 2006, Abstract only.
Colas, P., 2008, "The eleven-year switch of peptide aptamers," Journal of Biology, 7:2.
Crawford, M., et al., 2003, "Peptide aptamers: Tools for biology and drug discovery," Briefings in Functional Genomics and Proteomics, 2 (1): 72-79.
Clavijio, O.P., et al., "HLA-Cw*1701 is associated with two sub-Saharan African-derived HLA haplotypes: HLA-B*4201, DRB*03 and HLA-B*4202 without DRB1*03," 1999, Tissue Antigens, 54, pp. 303-306.
Davis, J.A., et al., 2006, "Deterministic hydrodynamics: Taking blood apart," PNAS, 103(40):14779-14784.
Fawcett, T., 2006, "An introduction to ROC analysis," Pattern Recognition Letters 27: 861-874.
Farrar, Kerrie et al., "Construction and screening of BAC libraries made from Brachypodium genomic DNA," Jun. 28, 2007, Nature Protocols, vol. 2 No. 7, pp. 1661-1674.
Gale, B.K. 'Bonding, Packaging, and Sacrificial Processes' [online], 2001 [retrieved Apr. 11, 2011] Retrieved from the Internet <URL: http://www.eng.utah.edu/~gale/mems/Lecture%2016a%20Bonding.pdf>.
Garcia, E.P., et al., 2005, "Scalable Transcriptional Analysis Routine—Mutiplexed Quantitative Real-Time Polymerase Chain Reaction Platform for Gene Expression Analysis and Molecular Diagnostics", Journal of Molecular Diagnostics, 7(4):444-454.

(Continued)

*Primary Examiner* — Jerry Lin
(74) *Attorney, Agent, or Firm* — Drinker Biddle & Reath LLP

(57) ABSTRACT

A method of identifying alleles of polymorphic sites in a plurality of nucleic acid samples including the steps of determining a source tag sharing number "d" for each of the alleles; performing a first reaction in a plurality of pools of the alleles to be identified to produce reaction products including a source tag identifying said each pool; pooling the pools to provide pooled pools; for each of the alleles to be identified, performing a second reaction using said reaction products to produce allele-specific second reaction products comprising a marker tag and a derived source tag; identifying said allele-specific second reaction products to identify the alleles. If "d" is equal to or larger than a maximum pool size, the first reaction may not be performed. Alleles may be binned together. A microparticle comprising one or more capture probes each comprising an oligonucleotide complementary to a subsequence of a target polynucleotide.

31 Claims, 24 Drawing Sheets

(56) References Cited

OTHER PUBLICATIONS

Herzenberg, L.A., et al., 2002, "The History and Future of the Fluorescence Activated Cell Sorter and Flow Cytometry: A View from Stanford," Clinical Chemistry 48(10): 1819-1827.

Iannone, Marie et al., "Multiplexed Single Nucleotide Polymorphism Genotyping by Oligonucleotide Ligation and Flow Cytometry," 2000, Cytometry, 39, pp. 131-140.

Kozlov, I.A., et al., 2004, "Efficient strategies for the conjugation of oligonucleotides to antibodies enabling highly sensitive protein detection." Biopolymers, 73(5): 621-30. Abstract only.

Lind and Kubista. Real-Time Immuno-PCR on the ICycler IQ™ System, Rev. A. [online], [retrieved on Apr. 4, 2011]. Retrieved from the Internet <URL: http://www.biocompare.com/Articles/ApplicationNote/1173/Real-Time-Immuno-PCR-On-The-1Cycler-IQ-System-Rev-A.html>.

Niemeyer, C.M., et al., 2005, "Immuno-PCR: high sensitivity detection of proteins by nucleic acid amplification," Trends in Biotechnology, 23(4): 208-216.

Pasanen, P.A., et al., 1993, "Receiver operating characteristic (ROC) curve analysis of the tumour markers CEA, CA 50 and CA 242 in pancreatic cancer; results from a prospective study," Br. J. Cancer (1993), 67: 852-855.

'Pooled BVD PCR Testing, Appendix I' Molecular Diagnostics [online], Jun. 30, 2011 [retrieved Jul. 13, 2011]. Retrieved from <URL: http://ahdc.vet.cornell.edu/docs/BVD_PCR_Pooled_Testing.pdf>.

Radisic, M., et al., 2006, "Micro- and nanotechnology in cell separation," International Journal of Nanomedicine; 1(1): 3-14.

Sacher et al., "Widmann's Clinical Interpretation of Laboratory Tests, 11$^{th}$ edition," F.A. Davis Company, Philadelphia, PA, 2000, chapter 1, pp. 3-7.

Sritharan, D. 'Size-based cell sorting by deterministic lateral displacement' Northeastern University, Chemical Engineering Master's Theses, Paper 8 [online], 2009 [retrieved Apr. 11, 2011]. Retrieved from the Internet <URL: http://hdl.handle.net/2047/d10019078>.

Stewart, C.C., et al., "Clinical Immunophenotyping by Flow Cytometry," Med TechNet Presentations [online], 1995 [retrieved Apr. 11, 2011]. Retrieved from the Internet <URL: http://www.medtechnet.com/public_pdf/mtc13.pdf>.

Tait Stevens, W., et al., 2008, "Introduction to BioArray Solutions' BeadChip Technology," Scientific Communications, ASHI Quarterly, Second Quarter [online], 2008 [retrieved Apr. 11, 2011]. Retrieved from the Internet <URL: http://www.immucor.com/bioarray/pdf/Introduction_to_BioArray_Solutions_BeadChip_Technology.pdf>.

Tyagi, Sanjay et al., "Molecular Beacons: Probes that Fluoresce upon Hybridization," Mar. 1996, Nature Biotechnology, 14, pp. 303-308.

'West Nile Virus-Procleix® WNV Assay—Summary Basis of Approval', Gen-Probe Incorporated [online], [retrieved on Apr. 11, 2011]. Retrieved from the US Food and Drug Administration using Internet <URL: http://www.fda.gov/downloads/BiologicsBloodVaccines/BloodBloodProducts/ApprovedProducts/LicensedProductsBLAs/BloodDonorScreening/InfectiousDisease/UCM090365.pdf>.

Won, J.I., et al., 2005, "Protein polymer drag—tags for DNA separations by end-labeled free-solution electrophoresis", Electrophoresis, 26: 2138-2148.

Zhao and Zhang, 2006, "Cellular mechanics study in cardiac myocytes using PDMS pillars array," Sensors and Actuators A: Physical, 125(2): 398-404.

Reischl, Udo, "PCR-Based Cloning and Subsequent Expression of Antigenic Proteins in *Escherichia coli*," Methods in Molecular Medicine, 1998, Molecular Diagnosis of Infectious Disease, 13, pp. 157-168.

Ye, Fei et al., "Fluorescent Microsphere-Based Readout Technology for Multiplexed Human Single Nucleotide Polymorhpisim Analysis and Bacterial Identification," 2001, Human Mutation, 17, pp. 305-316.

Vreeland, Wyatt N. et al., "Multiplexed, High-Throughput Genotyping by Single-Base Extension and End-Labeled Fre-Solution Electrophoresis," Sep. 1, 2002, Analytical Chemistry, vol. 74, No. 17, pp. 4328-4333.

Office Action mailed Sep. 5, 2012; U.S. Appl. No. 13/190,163.
Office Action mailed Aug. 31, 2012; U.S. Appl. No. 13/190,154.
Office Action mailed May 21, 2015; U.S. Appl. No. 13/190,154.
Office Action mailed Mar. 27, 2013; U.S. Appl. No. 13/190,154.
Office Action mailed May 30, 2013; U.S. Appl. No. 13/190,163.

\* cited by examiner

| | 700 | 710 | 720 | 730 | 740 |
|---|---|---|---|---|---|
| | | Blood Group System | Polymorphism | Number of alleles | Antigens |
| | | MNS | GYPA 59 C > T | 2 | M \| N |
| | | | GYPB 143 T > C | 2 | S \| s |
| | | | GYPB 230 C > T | 2 | |
| | | | +5 g > t | 2 | |
| | | RhC | RHCE 307 C>T | 2 | C \| c |
| | | | 733 C > G | 2 | V, VS |
| | | | 1006 G>T | 2 | |
| | | RhE | RHCE 676 G > C | 2 | E \| e |
| | | Lutheran | LU230 A > G | 2 | Lu^a \| Lu^b |
| | | Kell | KEL698 T > C | 2 | K \| k |
| | | | KEL1910 T>C | 2 | Js(a)/Js(b) |
| | | | KEL961 T>C | 2 | Kp(a)/Kp(b) |
| | | Duffy | FY125 G > A | 2 | Fy^a \| Fy^b |
| | | | FY265 C > T | 2 | |
| | | | FY -33 T > C | 2 | |
| | | Kidd | JK838 G > A | 2 | Jk^a \| Jk^b |
| | | Diego | DI2561 T > C | 2 | Di^a \| Di^b |
| | | Scianna | SC169 G > A | 2 | ScI \| ScII |
| | | Dombrock | DO323 G > T | 2 | Do^a \| Do^b |
| | | | DO350 C > T | 2 | Hy \| Jo |
| | | | DO793 A > G | 2 | |
| 760 → | | Colton | CO134 C > T | 2 | Co^a, Co^b |
| | | Landsteiner-Wiener | LW308 A > G | 2 | LW^a, LW^b |
| 750 → | | Hemoglobin S | HbS173 | 2 | |
| 770 → | | Number of Polymorphisms | | 24 | |

1200 — African American

| 1250 | 1252 | 1254 | 1256 | 1258 | 1260 | 1262 | 1264 | 1266 | 1274 | 1270 | | | 1272 |
|---|---|---|---|---|---|---|---|---|---|---|---|---|---|
| | | | | | | | | | | Cutoff (=C) | | | Max PoolSz |
| | | | | | | | MinFreq | | | 0.1800 | | | 32 |
| | | | | | | | 0.001 | | | | | | |
| Blood Grp System | ISBT Design | Alleles | A | B | F | d(s) | | pwr of 2 | 32 | 16 | 8 | 4 | 2 | 1 |
| Kell | 6-KEL | K(1/2) | 0.01 | 0.99 | 0.01 | 9.8729 | 3 | 8 | | | | | | 1 |
| Lutheran | 5-LU | LU | 0.03 | 0.97 | 0.03 | 3.2577 | 1 | 2 | | | | | 2 | |
| Duffy | 8-FY | FY | 0.12 | 0.88 | 0.12 | 0.7762 | 0 | 1 | | | | | LU | FY |
| MNSs | 2-MNS | GYPBS | 0.18 | 0.82 | 0.18 | 0.5000 | 0 | 1 | | | | | | GYPBS |
| Duffy | 8-FY | GATA | 0.29 | 0.71 | 0.29 | 0.2897 | 0 | 1 | | | | | | GATA |
| Dombrock | 14-DO | DO-793 | 0.31 | 0.69 | 0.31 | 0.2674 | 0 | 1 | | | | | | DO-793 |
| MNSs | 2-MNS | GYPA | 0.48 | 0.52 | 0.48 | 0.1517 | 0 | 1 | | | K(1/2) | | | GYPA |
| Kidd | 9-JK | JK | 0.72 | 0.28 | 0.72 | 0.3021 | 0 | 1 | | | | | | JK |
| Hemoglobin S | | HbS173 | 0.948 | 0.052 | 0.948 | 1.8581 | 0 | 1 | | | | | | HbS173 |
| Dombrock | 14-DO | DO-323 | 0.96 | 0.04 | 0.96 | 2.4307 | 1 | 2 | | | | | DO-323 | |
| Dombrock | 14-DO | DO-350 | 0.96 | 0.04 | 0.96 | 2.4307 | 1 | 2 | | | | | DO-350 | |
| Duffy | 8-FY | FY265 | 0.99 | 0.01 | 0.99 | 9.8729 | 3 | 8 | | | FY265 | | | |
| Scianna | 13-SC | SC(1/2) | 0.998 | 0.002 | 0.998 | 49.5631 | 5 | 32 | SC | | | | | |
| Diego | 10-Di | DI (B/A) | 1 | 0 | 1 | 99.1758 | 6 | 32 | DI (B/A) | | | | | |
| Colton | 15-CO | CO | 1 | 0 | 1 | 99.1758 | 6 | 32 | CO | | | | | |
| Landsteiner Wiener | 16-LW | LW | 1 | 0 | 1 | 99.1758 | 6 | 32 | LW | | | | 1220 | |
| | | | | | | | | 1210 | 4 | 0 | 2 | 0 | 3 | 7 |

Caucasian

| | | | | | | | | | MinFreq 0.001 | Cutoff (=C) 0.1800 | | | | Max PoolSz 32 |
|---|---|---|---|---|---|---|---|---|---|---|---|---|---|---|
| 1250 | 1252 | 1254 | 1256 | 1258 | 1260 | 1262 | 1264 | 1266 | 1274 | 16 | 8 | 4 | 2 | 1 |
| Blood Grp System | ISBT Design | Alleles | A | B | f | d(s) | | pwr of 2 | 32 | | | | 2 | 1 |
| Kell | 6-KEL | K(1/2) | 0.03 | 0.97 | | 3.2577 | 1 | 2 | | | | | K(1/2) | |
| Lutheran | 5-LU | LU | 0.03 | 0.97 | | 3.2577 | 1 | 2 | | | | | LU | |
| MNSs | 2-MNS | GYPBS | 0.34 | 0.66 | | 0.2388 | 0 | 1 | | | | | | GYPBS |
| Dombrock | 14-DO | DO-793 | 0.37 | 0.63 | | 0.2148 | 0 | 1 | | | | | | DO-793 |
| Duffy | 8-FY | FY | 0.41 | 0.59 | | 0.1881 | 0 | 1 | | | | | | FY |
| Kidd | 9-JK | JK | 0.52 | 0.48 | | 0.1517 | 0 | 1 | | | | | | JK |
| MNSs | 2-MNS | GYPA | 0.57 | 0.43 | 0.43 | 0.1765 | 0 | 1 | | | | | | GYPA |
| Duffy | 8-FY | GATA | 0.95 | 0.05 | 0.05 | 1.9345 | 0 | 1 | | | | | | GATA |
| Duffy | 8-FY | FY265 | 0.99 | 0.01 | 0.01 | 9.8729 | 3 | 8 | | | FY265 | | | |
| Scianna | 13-SC | SC(1/2) | 0.994 | 0.006 | 0.006 | 16.4879 | 4 | 16 | | SC(1/2) | | | | |
| Hemoglobin S | | HbS173 | 0.998 | 0.002 | 0.002 | 49.5631 | 5 | 32 | HbS173 | | | | | |
| Colton | 15-CO | CO | 0.999 | 0.001 | 0.001 | 99.1758 | 6 | 32 | CO | | | | | |
| Dombrock | 14-DO | DO-323 | 1 | 0 | 0.001 | 99.1758 | 6 | 32 | DO-323 | | | | | |
| Dombrock | 14-DO | DO-350 | 1 | 0 | 0.001 | 99.1758 | 6 | 32 | DO-350 | | | | | |
| Diego | 10-DI | DI (B/A) | 1 | 0 | 0.001 | 99.1758 | 6 | 32 | DI (B/A) | | | | | |
| Landsteiner Wiener | 16-LW | LW | 1 | 0 | 0.001 | 99.1758 | 6 | 32 | LW | | | | | 1240 |
| | | | | | | | | 1230 | 6 | 1 | 1 | 0 | 2 | 6 |

…

METHOD FOR DETERMINING AN ALLELE PROFILE OF NUCLEIC ACID

FIELD

The invention relates to methods of determining an allele profile for each of a plurality of nucleic acid samples, and more specifically to determining allele profiles of nucleic acid samples by determining source tag sharing numbers for the alleles and by using source tags and marker tags where the source tags may be shared among different nucleic acid samples that have the same source tag sharing number.

BACKGROUND

In the discussion of the background that follows, reference is made to certain structures and/or methods. However, the following references should not be construed as an admission that these structures and/or methods constitute prior art. Applicants expressly reserve the right to demonstrate that such structures and/or methods do not qualify as prior art.

Replacement human blood is vital to medical treatment. Many medical treatments including many surgical procedures would not be possible without the availability of donated blood to replace blood lost during such procedures or due to injuries.

One problem in supplying replacement blood is that it is perishable. Blood, contains cellular components, principally red blood cells ("erythrocytes"), platelets ("thrombocytes") and white blood cells ("leukocytes"), suspended in plasma. As soon as blood is collected, red cells within the blood may acquire "storage lesions," which may reduce the effectiveness of these cells to deliver oxygen to tissue. Moreover, freezing and thawing may damage cells and reduce their effectiveness. The blood may also acquire inflammatory factors, especially when white cells are allowed to remain. The blood may also contain infectious agents that may proliferate, especially when blood components are stored at room temperature as is the case for platelets. For these reasons, fresh blood is more effective and, in practice, is preferred over older blood. Regulatory agencies have set the time period for using red blood cells to 42 days after collection, and the time period for using platelets to five days (or 7 days provided special storage conditions are ensured), reflecting the risk of proliferation of bacteria as platelets are stored at room temperature. Expired blood components are no longer suitable for human use. In the United States of America, in 2006, approximately 400,000 units of 16.75 million units of red blood cells collected, and approximately 200,000 units of 1.810 million units of (single donor) platelets collected expire before use.

Another problem in supplying replacement blood is that the replacement blood is typically matched to the recipient's blood type only with respect to an abbreviated blood type such as A+, AB−, or O−, indicating the presence ("A", "B" or "AB") or absence ("O") of the antigens within the ABO blood group system and the presence ("+") or absence ("−") (often determined by traditional "agglutination" methods) of the D antigen, a constituent of the RH blood group system. However, blood cells express a multiplicity of antigens. For example, red blood cells comprise dozens of antigens within 30 blood group systems defined to date by the International Society of Blood Transfusion. Any of the antigens, which are associated with molecules on cell surfaces of replacement blood cells, may cause the recipient's immune system to treat the replacement blood as foreign if the recipient's own blood cells do not have the same antigens as the replacement blood antigens. This, in turn, may lead to immune reactions and adverse clinical events. Adverse events may be mild and have no significant effect on the patient or may be severe and life threatening. In 2006, 72,000 adverse transfusion-related events were reported.

Determining the identity of individual antigens, or that of an entire set comprising an antigen profile, for recipient and for (donors of) replacement blood may be prohibitively time consuming and expensive; in the USA, routine antigen testing prior to red blood cell transfusion currently is limited to the principal antigens, A, B and D while platelet transfusion routinely proceeds without any antigen testing.

One way to avoid an immune system reaction is to determine the recipient's and prospective donors' antigen profiles (for cells to be transfused) and to select replacement blood on the basis of its antigen profile such that it does not appear foreign to the recipient's immune system. However, finding suitable, or "compatible", antigen profiles may require determining the antigen profile of many donor blood samples. Additionally, current methods for determining blood cell antigen profiles, especially the traditional methods of directly probing antigens associated with proteins on cell surfaces are time consuming and expensive. Reagents that are needed to directly probe the antigens are scarce and expensive, and often unlicensed, and current procedures are time-consuming with only one antigen at a time being determined. Additionally, there may be many technical difficulties encountered especially when analyzing complex cases for patients who are in need of transfusion.

An alternative method of determining antigen profiles directly relies on the analysis of a genomic DNA ("gDNA") sample by determining specific sequences of nucleotides within genes known to encode blood group antigens. Alternate forms of related sequences of nucleotides, also referred to as alleles, may encode alternate forms of an antigen, as in the case of many blood group antigens. A variable site within the sequence of nucleotides, also referred to as polymorphic site or a polymorphism, may be referred to as a marker, and the composition at that site an allele or attribute of the DNA (that is: a genetic attribute); determining one or more alleles or attributes of DNA may be called determining an allele or attribute profile of the DNA. So, determining an attribute profile of the DNA may also be called determining an allele profile of the DNA, and more generally determining an attribute profile or allele profile for a nucleic acid, since DNA is a nucleic acid.

In current practice, it is common to determine allele profiles one sample at a time, and often one allele at a time, and given the requisite expenditure of time, frequently many hours, even with state-of-the-art methods of "multiplex" analysis providing the entire allele profile of an individual, making it impractical to conduct comprehensive allele profiling of large numbers of individuals, including recipients or donors of blood. These same problems relating to transfusion may be common to problems where alleles of a nucleic acid must be determined, especially when large numbers of samples are to be processed rapidly and cost-effectively.

SUMMARY

It is to be understood that both the foregoing general description and the following detailed description are exemplary and explanatory and are intended to provide further explanation of the invention as claimed.

A method of identifying alleles of a plurality of polymorphic sites for at least two nucleic acid samples in a plurality of nucleic acid samples is disclosed. The method includes step (a) for each of the alleles to be identified, determining a source tag sharing number "d" for the allele.

The method includes step (b) for each of the different determined source tag sharing numbers "d": (i) dividing the plurality of nucleic acid samples into nucleic acid sample subsets, each subset containing approximately the source tag sharing number "d" of nucleic acid samples so that each nucleic acid sample of the plurality of nucleic acid samples is included in at least one subset; (ii) for each of the nucleic acid sample subsets, placing a portion of each of the nucleic acid samples included in the nucleic acid sample subset into a pool, thereby providing a plurality of pools for the source tag sharing number "d", wherein each pool comprises a pooled subset of nucleic acid samples; and (iii) for each pool of the plurality of pools for the source tag sharing number "d", performing a reaction in the pool to produce reaction products comprising a source tag identifying said each pool, wherein said reaction products are produced using as templates said pooled subset of nucleic acid samples in said each pool.

The method includes step (c) for each of the different determined source tag sharing numbers "d", pooling in at least one pooled pool at least some of the said produced reaction products from at least two pools of the plurality of pools for the source tag sharing number "d", thereby providing a plurality of pooled pools comprising at least one pooled pool for each of the different determined source tag sharing numbers "d".

The method includes step (d) for each of the alleles to be identified, performing a second reaction using said reaction products comprising said source tag to produce allele-specific second reaction products comprising a marker tag and a derived source tag, wherein said derived source tag is at least one of: said source tag, a copy of said source tag, or a copy of the complement of the source tag, and wherein said marker tag identifies an allele at a polymorphic site, and wherein said second reaction is in a pooled pool of said at least one pooled pool for the source tag sharing number "d", the "d" corresponding to the source tag sharing number "d" determined for the allele in step (a).

The method includes step (e) identifying said allele-specific second reaction products by interrogating said allele-specific second reaction products comprising said derived source tag and said marker tag, and if the interrogating of said allele-specific second reaction products indicates unambiguous results, then identifying said alleles of the plurality of polymorphic sites, otherwise if the interrogating of said allele-specific second reaction products indicates ambiguous results, then disambiguating the ambiguous results.

Disambiguating the ambiguous results may include repeating the method of identifying alleles, wherein the alleles to be identified are each allele that was not identified because the interrogating of said allele-specific products indicates said ambiguous results, and the plurality of nucleic acid samples are nucleic acid samples that comprise alleles that were not identified, and step (a) may include determining a lower source tag sharing number "d" than the previously determined source tag sharing number "d" for each allele that cannot be identified because the interrogating of said allele-specific products indicates said ambiguous results.

The alleles to be identified may include other alleles not yet identified.

The source tag sharing number "d" for each allele may be determined based on a frequency of the allele.

In step (b) (iii) performing a reaction in a pool may include amplifying the nucleic acid samples in the pool with primers comprising a source tag, wherein said reaction products comprise amplicons.

Amplifying the nucleic acid samples may include amplifying the nucleic acid samples by performing a polymerase chain reaction (PCR).

In step (d) performing a second reaction may includes amplifying said reaction products with allele-specific primers using said reaction products as templates, wherein said allele-specific second reaction products comprise allele-specific amplicons.

Said allele-specific amplicons may indicate the identity of the allele of the allele-specific amplicon by a length of the allele-specific amplicon.

The method of claim 6, wherein said amplifying the nucleic acid samples comprises amplifying the nucleic acid samples by performing a polymerase chain reaction (PCR).

In step (e) disambiguating the ambiguous results may include performing a method of deconvolution for each allele that was not identified because the interrogating of said allele-specific products indicates said ambiguous results.

The marker tag of the second reaction products may include at least one of the following to identify an allele: an oligonucleotide tag or a fluorescent tag.

The marker tag may include an oligonucleotide tag which may include a first nucleotide sequence to identify an allele and a second nucleotide sequence to identify a polymorphic site.

Said oligonucleotide tag may include a nucleotide sequence to identify both a polymorphic site of the plurality of polymorphic sites and said allele.

Said marker tag of said second reaction products may include at least one of the following to identify a polymorphic site of the plurality of polymorphic sites: an oligonucleotide tag or a fluorescent tag.

In step (e) interrogating may include interrogating said derived source tag and said marker tag of said second reaction products by contacting said second reaction products with micro-particles. The micro-particles may include a first capture probe complementary to said derived source tag and may include an optical tag that identifies said micro-particle.

The micro-particles may include a second capture probe complementary to said marker tag, and the marker tag may be an oligonucleotide tag.

The marker tag may include an optical tag.

The optical tag may be a fluorescent tag.

In step (e) interrogating may include interrogating said derived source tag and said marker tag of said second reaction products by electrophoretic separation of said second reaction products.

The interrogating may include determining a length of the second reaction products by electrophoretic separation.

The marker tag may include an optical tag.

The source tag identifying said each pool may encode each pool by a length of the source tag.

The marker tag may encode an identity of a polymorphic site by a length of the marker tag.

The identity of a polymorphic site may be encoded by the total length of said second reaction products.

The second reaction products encode at least one of an allele or a polymorphic site.

The source tag may be an unique nucleotide sequence.

The marker tag may be an unique nucleotide sequence.

In step (e) identifying said alleles of the plurality of polymorphic sites may include if said interrogating of said allele-specific second reaction products indicates allele-specific second reaction products in the same pooled pool with different marker tags for said polymorphic site and if "d"=1, then a nucleic acid sample of the plurality of nucleic acid samples corresponding to a pool identified by said derived source tag is identified as heterozygous for the polymorphic site.

In step (e) identifying said alleles of the plurality of polymorphic sites may include if said interrogating of said allele-specific second reaction products indicates allele-specific second reaction products with marker tags that are the same in the same pooled pool for said polymorphic site and if "d">1, then each of the nucleic acids used to form the pool identified by "d" has the allele identified by the marker tag.

The method of identifying alleles may include prior to step (d): binning said alleles to be identified into one or more bins based on a frequency of said alleles; and may include wherein in step (d) the second reaction is performed in a same pooled pool of said at least one pooled pool for each of the alleles grouped into a same bin of the plurality of bins, wherein two alleles are binned into the same bin only if the two alleles have the same source tag sharing number "d".

The marker tag may uniquely identify an allele at a polymorphic site.

A method of identifying alleles of a plurality of polymorphic sites in a plurality of nucleic acid samples is disclosed. The method includes step (a) for each of the alleles to be identified, determining a source tag sharing number "d" for the allele.

The method includes step (b) for each of the different determined source tag sharing numbers "d": (i) dividing the plurality of nucleic acid samples into nucleic acid sample subsets, each subset containing approximately the source tag sharing number "d" of nucleic acid samples so that each nucleic acid sample of the plurality of nucleic acid samples is included in at least one subset; (ii) for each of the nucleic acid sample subsets, placing a portion of each of the nucleic acid samples included in the nucleic acid sample subset into a pool, thereby providing a plurality of pools for the source tag sharing number "d", wherein each pool comprises a pooled subset of nucleic acid samples; and (iii) if "d" is less than a maximum_pool_size, for each pool of the plurality of pools for the source tag sharing number "d", performing a reaction in the pool to produce reaction products comprising a source tag identifying said each pool, wherein said reaction products are produced using as templates said pooled subset of nucleic acid samples in said each pool.

The method includes step (c) for each of the different determined source tag sharing numbers "d", if "d" is less than a maximum_pool_size, pooling in at least one pooled pool at least some of the said produced reaction products from at least two pools of the plurality of pools for the source tag sharing number "d", thereby providing a plurality of pooled pools comprising at least one pooled pool for each of the different determined source tag sharing numbers "d", otherwise if "d" is equal to the maximum_pool_size then said each pool is the at least one pooled pool.

The method includes step (d) for each of the alleles to be identified, if "d" is less than a maximum_pool_size, performing a second reaction using said reaction products comprising said source tag to produce allele-specific second reaction products comprising a marker tag and a derived source tag, wherein said derived source tag is at least one of: said source tag, a copy of said source tag, or a copy of the complement of the source tag, and wherein said marker tag identifies an allele at a polymorphic site, and wherein said second reaction is in a pooled pool of said at least one pooled pool for the source tag sharing number "d", the "d" corresponding to the source tag sharing number "d" determined for the allele in step (a), otherwise if "d" is equal to a maximum_pool_size then performing a second reaction using said reaction products to produce allele-specific second reaction products comprising a marker tag, wherein said marker tag uniquely identifies an allele at a polymorphic site, and wherein said second reaction is in the pooled pool for "d", the "d" corresponding to the source tag sharing number "d" determined for the allele in step (a).

The method includes step (e) if "d" is less than the maximum_pool_size, identifying said allele-specific second reaction products by interrogating said allele-specific second reaction products comprising said derived source tag and said marker tag, and if the interrogating of said allele-specific second reaction products indicates unambiguous results, then identifying said alleles of the plurality of polymorphic sites, otherwise if the interrogating of said allele-specific second reaction products indicates ambiguous results, then disambiguating the ambiguous results, otherwise if "d" is equal to the maximum_pool_size then identifying said allele-specific second reaction products by interrogating said allele-specific second reaction products comprising said marker tag, and if the interrogating of said allele-specific second reaction products indicates unambiguous results, then identifying said alleles of the plurality of polymorphic sites, otherwise if the interrogating of said allele-specific second reaction products indicates ambiguous results, then disambiguating the ambiguous results.

The maximum_pool_size may be a number of nucleic acid samples, wherein the number is based on technical limitations of performing the steps of the method.

The method of identifying alleles may include prior to step (d): binning said alleles to be identified into one or more bins based on a frequency of said alleles.

In step (d) the second reaction may be performed in a same pooled pool of said at least one pooled pool for each of the alleles grouped into a same bin of the plurality of bins, wherein two alleles are binned into the same bin only if the two alleles have the same source tag sharing number "d".

According to another aspect, a microparticle is provided for binding to a target polynucleotide. In one embodiment, the microparticle comprises a first capture probe attached to the microparticle and extending from the microparticle. The first capture probe comprises a nucleotide sequence segment complementary to a first target nucleotide sequence of a target polynucleotide. The microparticle further comprises a second capture probe attached to the microparticle and extending from the microparticle. The second capture probe comprises a nucleotide sequence segment complementary to a second target nucleotide sequence of the target polynucleotide. The microparticle binds the target polynucleotide by hybridization of the first and second capture probes to said first and second complementary target nucleotide sequences on the target polynucleotide.

In one embodiment of the aforesaid microparticle, the nucleotide sequence segments of the first and second capture probes are respectively complementary to first and second target nucleotide sequences located at opposite ends of the target polynucleotide. In some embodiments, one of the capture probes extends from the microparticle in a 5'-3' orientation, and the other of the capture probes extends from the microparticle in a 3'-5' orientation. In other embodiments, both of the capture probes extend from the microparticle in a 5'-3' orientation, or both of the capture probes extend from the microparticle in a 3'-5' orientation.

In another embodiment, a microparticle is provide for binding to target polynucleotide, the microparticle comprising a capture probe attached to the microparticle and extending from the microparticle. The capture probe comprises a first nucleotide sequence segment complementary to a first target nucleotide sequence of a target polynucleotide, and a second nucleotide sequence segment complementary to a second target nucleotide sequence of the target polynucleotide. The microparticle binds the target polynucleotide by hybridization of the first and second nucleotide sequence segments of the capture probe to the first and second target nucleotide sequences on the target polynucleotide. In one embodiment of the microparticle, the first and second nucleotide sequence segments of the capture probe are respectively complementary to first and second target nucleotide sequences located at opposite ends of the target polynucleotide.

BRIEF DESCRIPTION OF THE DRAWING

The following detailed description can be read in connection with the accompanying drawings in which like numerals designate like elements and in which:

FIG. 6B depicts nucleotides 10-17 of SEQ ID NO. 1 (left image) and nucleotides 6-17 of SEQ ID No. 1 (right image);

FIG. 7 schematically illustrates a table of DNA polymorphisms that are relevant to red blood cell antigens;

FIGS. 8C and 8E depict $^{s-32}$amplicon$^{VL1}$ (SEQ ID No. 7);

FIGS. 12A and 12B schematically illustrates an example of determining the number "d" for a set of polymorphic sites with two sets of allele frequencies, one for an African American population (top), the other for a Caucasian population (bottom);

DETAILED DESCRIPTION

Figures 1A, 1B:
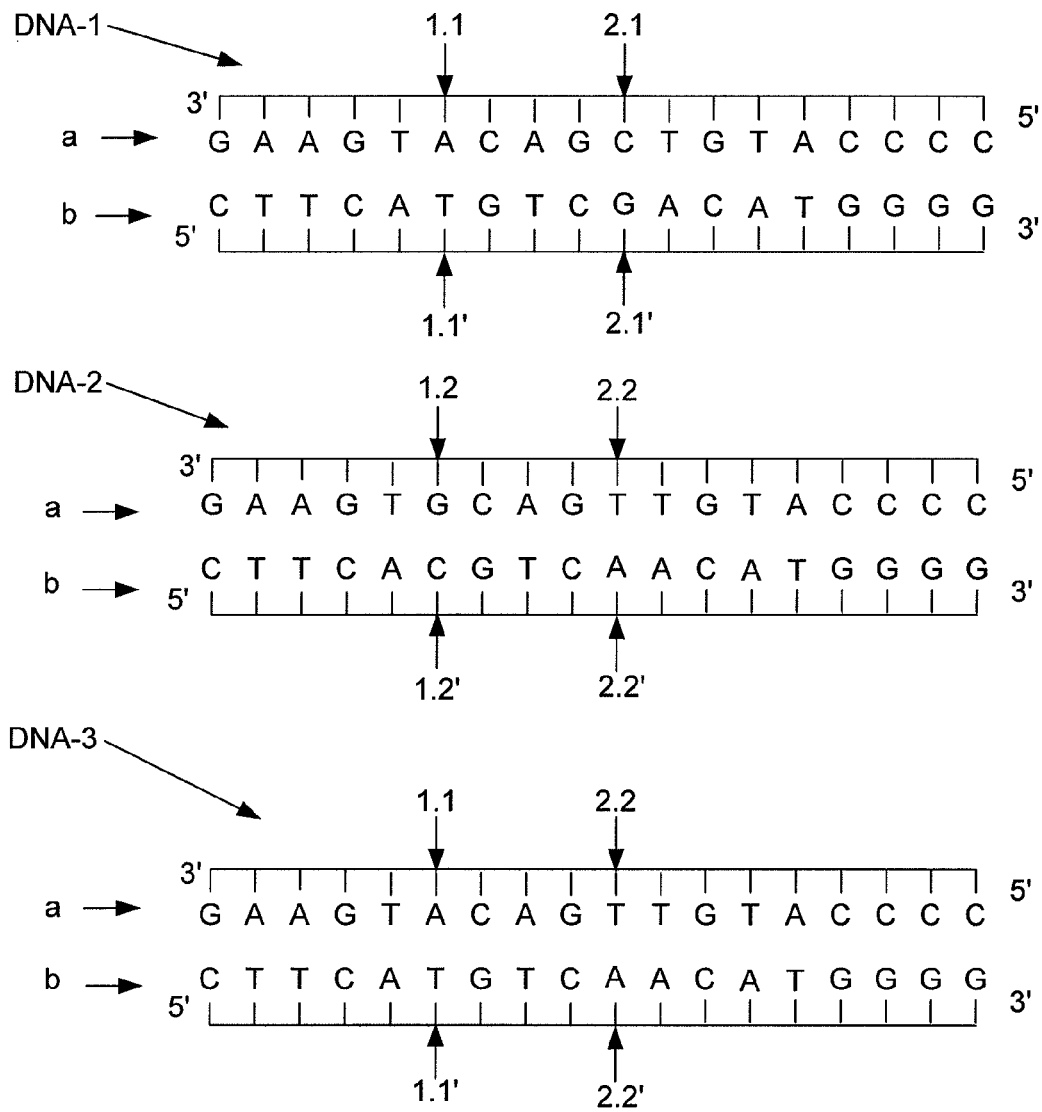
FIG. 1A schematically illustrates three portions of DNA molecules, DNA-1, DNA-2, and DNA-3 (DNA-1a: SEQ ID No.1; DNA-1b: SEQ ID No. 2; DNA-2a: SEQ ID No. 3; DNA-2b: SEQ ID No. 4; DNA-3a: SEQ ID No.5; DNA-3b: SEQ ID No. 6)
FIG. 1B schematically illustrates an allele profile for the three DNA-1, DNA-2, DNA-3 molecules illustrated in FIG. 1A.

Unless otherwise defined, all technical and scientific terms used herein have the same meaning as commonly understood by one of ordinary skill in the art to which this invention belongs. Still, certain elements are defined for the sake of clarity and ease of reference.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

An "attribute" is a characteristic of a sample. Non-limiting examples of attributes include a gene allele and an antigen. Attribute characterization can include identifying a specific gene allele, identifying the presence of one or more of a set of antigens (such as blood antigens), identifying the presence or absence of a specific antigen, and identifying the relative amount of an antigen.

An "allele" refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variants", "polymorphisms", or "mutations".

The phrase "identifying alleles of a plurality of polymorphic sites for at least two nucleic acid samples" as used herein refers to ascertaining alleles of a plurality of polymorphic sites for the at least two nucleic acid samples; for instance, identifying a first nucleic acid sample as having alleles encoding $Lu^a$, Scl and $Co^a$ and identifying a second nucleic acid sample as having alleles encoding $Lu^a$, Scl and $Go^a$. The phrase therefore encompasses both identifying the presence of a specific allele of polymorphic site, for instance, in a pool of nucleic acid samples, and identifying in which nucleic acid sample or samples have that specific allele. "To identify an allele of a nucleic acid sample" and "to determine an allele of a nucleic acid sample" are used interchangeably.

An "allele-specific probe" is a probe that binds preferentially to a target nucleotide sequence comprising a certain allele at a polymorphic site in comparison to other alleles of the same polymorphism.

An "allele-specific primer" is a primer that binds preferentially to a target nucleotide sequence comprising a certain allele at a polymorphic site and provides for amplification of the allele in comparison to other alleles of the same polymorphism; elongation of an allele-specific primer produces a product complementary to the template sequence so that, if template sequences differ, in positions other than that targeted by the primer, so will the sequences of the elongation products, and in such a case, an allele-specific primer also may be referred to as a group-specific primer, the group comprising all alleles sharing the allele of the polymorphic site to which the primer is directed.

"Amplicon" means the product of a polynucleotide amplification reaction. That is, amplicons are a population of polynucleotides, usually double stranded, that are replicated from one or more starting sequences. The one or more starting sequences may be one or more copies of the same sequence, or may be a mixture of different sequences. Amplicons may be produced by a variety of amplification reactions whose products are multiple replicates of one or more target nucleic acids, that serve as templates for the addition of nucleobases in accordance with Watson-Crick base pairing rules. In one aspect, template-mediated reactions are primer extensions, catalyzed by a nucleic acid polymerase or template-mediated poly- or oligonucleotide ligations catalyzed by a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: U.S. Pat. Nos. 4,683, 195; 4,965,188; 4,683,202; 4,800,159 (PCR); U.S. Pat. No. 5,210,015 (real-time PCR with "TAQMAN™" probes); U.S. Pat. No. 6,174,670; U.S. Pat. No. 5,399,491 ("NASBA"); U.S. Pat. No. 5,854,033 (rolling circle amplification). In one aspect, amplicons of the invention are produced by PCRs. As used herein, the term "amplifying" means performing (at least one cycle of—NOTE: a single primer "extension" or elongation pass without cycling of temperature may be sufficient in some embodiments) an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

An "allele-specific amplicon" means an amplicon that is the result of the template-mediated elongation of an allele-specific primer.

The term "complementary" refers to nucleic acid sequences comprising complementary base-pairs according to the standard Watson-Crick base-pairing, or that are capable of hybridizing to a particular nucleic acid segment under relatively stringent conditions.

The term "gene" refers to a nucleic acid (e.g., DNA) sequence that comprises coding sequences necessary for the production of a polypeptide, precursor, or RNA (e.g., rRNA, tRNA). The term "gene" encompasses both cDNA and genomic forms of a gene.

A "genome" is all the genetic material of an organism. In some instances, the term genome may refer to the chromosomal DNA. Genome may be multichromosomal such that the DNA is cellularly distributed among a plurality of individual chromosomes. For example, in human there are 22 pairs of chromosomes plus a gender associated XX or XY pair. DNA derived from the genetic material in the chromosomes of a particular organism is genomic DNA. The term genome may also refer to genetic materials from organisms that do not have chromosomal structure. In addition, the term genome may refer to mitochondria DNA.

The term "genotyping" refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be an A in some individuals and a C in other individuals. Those individuals who have an A at the position have the A allele and those who have a C have the C allele. A polymorphic location may have two or more possible alleles and oligonucleotide probes or primers may be designed to distinguish between all possible combinations.

The term "hybridization" refers to the process in which two single-stranded nucleic acids bind non-covalently to form a double-stranded nucleic acid; triple-stranded hybridization is also possible under certain conditions. Complementary sequences in the nucleic acids pair with each other to form a double helix. The resulting double-stranded nucleic acid is a "hybrid." Hybridization may be between, for example two complementary or partially complementary sequences. The hybrid may have double-stranded regions and single stranded regions. The hybrid may be, for example, DNA:DNA, RNA:DNA or DNA:RNA. Hybrids may also be formed between modified nucleic acids. One or both of the nucleic acids may be immobilized on a solid support. Hybridization techniques may be used to detect and isolate specific sequences, measure homology, or define other characteristics of one or both strands.

"Hybridization probes" are oligonucleotides capable of binding in a base-specific manner to a complementary strand of nucleic acid. Such probes include peptide nucleic acids, as described in Nielsen et al., 1991, Science 254, 1497-1500, and other nucleic acid analogs and nucleic acid mimetics. See U.S. Pat. No. 6,156,501.

"Ligation" means to form a covalent bond or linkage between the termini of two or more nucleic acids, e.g. oligonucleotides and/or polynucleotides, in a template-mediated reaction. The nature of the bond or linkage may vary widely and the ligation may be carried out enzymatically or chemically. A variety of template-mediated ligation reactions are described in the following references, which are incorporated by reference: U.S. Pat. No. 4,883,750; U.S. Pat. No. 5,476,930; U.S. Pat. No. 5,593,826; U.S. Pat. No. 5,426,180; U.S. Pat. No. 5,871,921.

A "label" is a composition detectable by spectroscopic, photochemical, biochemical, immunochemical, or chemical means. For example, useful labels include fluorescent dyes, electron-dense reagents, enzymes (e.g., as commonly used in an ELISA), biotin, digoxigenin, or haptens and proteins for which antisera or monoclonal antibodies are available. The label may be bound, either covalently or non-covalently, to a molecule. For example, a label may be bound to a tag and/or a ligand that binds a molecule or a tag, and more than one type of label can be bound to either or both of the tag and ligand. Thus, for example, an oligonucleotide tag can be covalently bound to a biotin group, where the oligonucleotide tag is then bound to a ligand that has a fluorescent label attached to the ligand.

As used herein, "nucleic acid" may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982), the entire disclosure of which is incorporated herein by reference.) Indeed, the invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

A single nucleotide polymorphism ("SNP") is a single position in a particular DNA sequence characterized by the presence in a population of two, three or four different nucleotides at that position. As is well known in the art, the position refers to a basepair. Therefore, the identity of a SNP allele can be accomplished by identifying the nucleotide on the sense strand or its base-paired complement on the antisense strand of a double-stranded DNA molecule.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide may be a peptide nucleic acid (PNA). (See U.S. Pat. No. 6,156,501 the entire disclosure of which is incorporated herein by reference.)

The term "polymorphism" refers to the occurrence of two or more genetically determined alternative sequences or alleles in a population. A polymorphic marker or site is the locus at which divergence occurs. A polymorphism may comprise one or more base changes, an insertion, a repeat, or a deletion. A polymorphic locus may be as small as one base pair. The first identified allelic form is arbitrarily designated as the reference form and other allelic forms are designated as alternative or variant alleles. The allelic form occurring most frequently in a selected population is sometimes referred to as the wildtype form. A di-allelic or bi-allelic polymorphism has two forms. A tri-allelic polymorphism has three forms.

As used herein, a "pool" refers to a physical mixture comprising a portion of two or more biological samples, such as two or more nucleic acid samples. A "pooled pool" refers to a physical mixture comprising a portion of each of two or more different pools.

A "maximum pool size" is a size that is approximately the maximum total number of biological samples that are or can be pooled together for reactions in the method. The "maximum pool size" may be determined by limitations arising from the steps of the method. For example, in some embodiments, two microparticles with different tags are added to a pool to identify alleles of a single nucleic acid sample. Thus, the number of nucleic acid samples that are pooled together is limited by the number of different microparticle tags that can be manufactured. The "maximum pool size" may be different for different reactions performed in the method, and the "maximum pool size" may be adjusted so that the method is efficient. In general, the "maximum pool size" is an indication of physical limits of the reactions that are performed in the method, but may be adjusted to more efficiently perform the method.

"Polynucleotide" and "oligonucleotide" are used interchangeably in this disclosure.

A "primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally-occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers may be labeled with, e.g., detectable moieties, such as chromogenic, radioactive or fluorescent moieties, or moieties for isolation, e.g., biotin. In some embodiments, complementarity of the primer's 3' terminal base and the template is a necessary condition for primer extension or elongation.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

As used herein a "probe" or "capture probe" is defined as a nucleic acid capable of binding to a target nucleic acid of complementary sequence by one or more types of chemical interactions, usually complementary base pairing mediated by hydrogen bond formation. As used herein, a probe may include natural (i.e., A, G, U, C, or T) or modified bases (7-deazaguanosine, inosine, etc.) forming an oligomer by way of phosphodiester or other bonds that do not interfere with hybridization. Thus, probes may be peptide nucleic acids in which the constituent bases are joined by peptide bonds rather than phosphodiester linkages.

"Sample" or "biological sample" as used herein means a biological material isolated from an individual. The biological sample may contain any biological material suitable for detection, and may comprise cellular and/or non-cellular material obtained from the individual. A "nucleic acid sample" is a sample comprising nucleic acid, in any degree of purity.

The term "tag" refers to a molecule or portion thereof with a recognizable feature that allows it to be distinguished from other tag molecules, e.g., a distinguishable nucleotide or amino acid sequence, nucleotide or amino acid sequence length, shape, size, mass, color, optical density, differential absorbance or emission of light, chemical reactivity, magnetic or electronic properties and the like. Preferred examples of tags include tags comprising oligonucleotides (oligonucleotide tags) and fluorescers. A specific oligonucleotide tag may serve as to identify a sample or sequence, in the manner of a "barcode". A "tag" may include a florescent label so that the tag may be identified.

A "source tag" is a tag that is attached to or comprises a polynucleotide or oligonucleotide and identifies the source of the polynucleotide or oligonucleotide or nucleic acid under study. In some embodiments, a source tag is an "oligonucleotide tag". Oligonucleotide tags may be identified by their nucleotide sequences. In some embodiments the oligonucleotide tag is a sequence of nucleotides selected such that the sequence does not duplicate a naturally occurring sequence in the genome of the organism under study; such an oligonucleotide tag also is referred to as a "barcode"

A "marker tag", as used herein, is a tag that uniquely identifies a polymorphic site and/or allele. In some embodiments, the marker tag is the length of the "second" reaction products, which are defined below. In some embodiments, a marker tag is a tag that is attached to or comprises a polynucleotide or oligonucleotide and identifies an allele and/or polymorphic site under study. In some embodiments, a marker tag is an "oligonucleotide tag". Oligonucleotide tags may be identified by their unique nucleotide sequences and are "barcodes". In some embodiments, the marker tag may identify an allele and/or polymorphic site under study by the length of the oligonucleotide tag. In some embodiments, the marker tag may identify an allele and/or polymorphic site by a fluorescent label.

The term "target" as used herein refers to a molecule that has an affinity for a given probe, or a segment of a particular molecule that has affinity for a probe. Targets may be naturally-occurring or man-made molecules. Examples of targets which can be employed by this invention include, but are not restricted to oligonucleotides and nucleic acids. A "target sequence" is a specific sequence of nucleotides of a target which is bound by a probe.

"Target nucleic acid" or "template nucleic acid sequence" or "target nucleotide sequence" refers to a region of a nucleic acid that is to be either replicated, amplified, and/or detected, generally including the flanking sequences to which primers may be directed By "reaction product" produced from a nucleic acid template is meant an amplification product, a transcription product, a reverse-transcription product, or any other nucleic acid product resulting from template-mediated nucleic acid synthesis.

The term "interrogating" as used herein refers to performing a process on reaction products that can be used to identify said reaction products in order to produce results that may be used to identify one or more alleles at one or more polymorphic site for one or more nucleic acid samples. "Identifying reaction products" refers to identifying the marker tags, and, if present, the source tags of the reaction products.

The term "unambiguous results" as used herein refers to results that can be used to determine an allele at a polymorphic site for a nucleic acid. The term "result" as used herein refers to an outcome of interrogating reaction products.

The term "ambiguous results" as used herein refers to results that require additional steps in order to determine an allele at a polymorphic site for a nucleic acid; in some embodiments two or more possible alleles, of two or more samples within a reaction, may have produced the same results.

As envisioned in the present invention with respect to the disclosed methods and compositions of matter, in one aspect the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

The invention contemplates sample preparation methods in certain embodiments. Prior to or concurrently with the methods of genetic analysis described herein, the information comprising a nucleotide sequence in a sample for analysis may be amplified using a variety of mechanisms, some of which may employ polymerase chain reaction (PCR). See, for example, PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675, each of which is incorporated herein by reference in their entireties for all purposes.

Other suitable amplification methods include the ligase chain reaction (LCR) (for example, Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed PCR (CP-PCR) (U.S. Pat. No. 4,437,975), arbitrarily primed PCR (AP-PCR) (U.S. Pat. Nos. 5,413,909, 5,861,245), degenerate oligonucleotide primed PCR (DOP-PCR) (Wells et al., 1999, Nuc Acids Res 27:1214-1218) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494, 810, 4,988,617 and in U.S. Ser. No. 09/854,317, each of which is incorporated herein by reference.

In certain aspects of the invention, nucleic acids are detected by detecting one or more tags (also referred to as labels) attached to a sample nucleic acids or to molecules that bind to nucleic acids. The tag or label may be incorporated by any of a number of means well known to those of skill in the art. In one embodiment, the tag is simultaneously incorporated during the amplification step in the preparation of the sample nucleic acids. Thus, for example, PCR with labeled primers or labeled nucleotides will provide a labeled amplification product. In another embodiment, transcription amplification, as described above, using a labeled nucleotide (e.g. fluorescein-labeled UTP and/or CTP) incorporates a label into the transcribed nucleic acids.

Alternatively, a tag may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example, nick translation or end-labeling (e.g. with a labeled RNA) by kinasing the nucleic acid and subsequent attachment (ligation) of a nucleic acid linker joining the sample nucleic acid to a label (e.g., a fluorophore).

Detectable tags suitable for use in the invention include any composition detectable by spectroscopic, photochemical, biochemical, immunochemical, electrical, optical or chemical means. Useful tags in the invention include, but are not limited to: biotin for staining with labeled streptavidin conjugate; anti-biotin antibodies, magnetic beads (e.g., Dynabeads™); fluorescent dyes (e.g., fluorescein, texas red, rhodamine, green fluorescent protein, and the like); radiolabels (e.g., $^{3}H$, $^{125}I$, $^{35}S$, $^{4}C$, or $^{32}P$); phosphorescent labels; enzymes (e.g., horse radish peroxidase, alkaline phosphatase and others commonly used in an ELISA); and colorimetric labels such as colloidal gold or colored glass or plastic (e.g., polystyrene, polypropylene, latex, etc.) beads. Patents teaching the use of such labels include U.S. Pat. Nos. 3,817,837, 3,850,752, 3,939, 350, 3,996,345, 4,277,437, 4,275,149 and 4,366,241, each of which is hereby incorporated by reference in its entirety for all purposes.

Means of detecting such labels are well known to those of skill in the art. Thus, for example, radiolabels may be detected using photographic film or scintillation counters; fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

In one embodiment, the label comprises a microparticle that may be color-encoded, such as described in U.S. Pat. No. 7,083,914, the entire disclosure of which is incorporated herein by reference. Color codes are assigned for the purpose of uniquely labeling members of a group of microparticles and preserve their chemical identity thus the identity of microparticle-coupled nucleic acid. Color codes are based on a set of encoding fluorophores of distinguishable wavelengths, excited-state lifetimes and levels of intensity, the latter controlled by adjusting the abundances of dyes. The codes are interrogated to identify the bound nucleic acid.

In certain embodiments of the invention, polynucleotide hybridization assays are conducted. Hybridization assay procedures and conditions will vary depending on the application and are selected in accordance with the general binding methods known including those referred to in: Maniatis et al. Molecular Cloning: A Laboratory Manual (2.sup.nd Ed. Cold Spring Harbor, N.Y, 1989); Berger and Kimmel, Methods in Enzymology, Vol. 152, Guide to Molecular Cloning Techniques (Academic Press, Inc., San Diego, Calif., 1987); Young and Davism, Proc. Natl. Acad. Sci USA, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

The invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, in PCT Application PCT/US99/06097 (published as WO99/47964), each of which also is hereby incorporated by reference in its entirety for all purposes.

In some embodiments of the invention, the source tags utilized in the practice of the invention comprise oligonucleotide tags. Usually, an oligonucleotide tag is attached to the 3'- or 5'-end of the a polynucleotide, or is incorporated into a reaction product, e.g. polymerase reaction product, which uses the polynucleotide as a template. Oligonucleotide tags may vary widely in size and compositions; the following references provide guidance for selecting sets of oligonucleotide tags appropriate for particular embodiments. See U.S. Pat. No. 5,635,400; Brenner et al., Proc. Natl. Acad. Sci., 97: 1665-1670 (2000); European patent publication 0 303 459; Shoemaker et al., Nature Genetics, 14: 450-456 (1996); European patent publication 0799897A1; and U.S. Pat. No. 5,981,179; the entire disclosures of which are incorporated herein by reference. In one aspect, oligonucleotide tags can each have a length within a range of from 2 to 36 nucleotides, or from 4 to 30 nucleotides, or from 8 to 20 nucleotides, respectively. A set of oligonucleotide tags may have a size in the range of from several tens to many thousands, or even millions. Preferably, the nucleotide sequence of the oligonucleotide tag is a sequence selected such that it is distinguishable from human genomic sequences, i.e., the oligonucleotide tags comprise barcodes.

As will be appreciated by those in the art, the attachment, or joining, of an oligonucleotide tag to a polynucleotide can be done in a variety of ways. In a preferred embodiment, the sequence of the oligonucleotide tag is incorporated into the nucleotide sequence of primers of the reaction (extension primers, amplification primers, readout probes, genotyping primers, Rolling Circle primers, etc.) during the chemical synthesis of the primers. The tag then is incorporated in the reaction product formed in a primer-extension reaction, i.e., polymerase chain reaction, to form reaction product that now contains the tag sequence. Alternatively, the tag sequences can be added enzymatically. Furthermore, the tag can be attached to the target after synthesis; this post-synthesis attachment can be either covalent or non-covalent.

An oligonucleotide tag may be joined to a polynucleotide by a ligation method, i.e., formation a covalent bond or linkage between the termini of the oligonucleotide tag and polynucleotide in a template-driven reaction. The nature of the bond or linkage may vary widely and the ligation may be carried out enzymatically or chemically. A variety of template-driven ligation reactions are described in the following, which are incorporated by reference: Whitely et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al., Methods in Enzymology, 68: 50-71 (1979); Engler et al., The Enzymes, 15: 3-29 (1982); and Namsaraev, U.S. patent publication 2004/0110213.

In one embodiment of the invention, electrophoretic tags, or "e-tags" are used as source tags or marker tags, that are incorporated into nucleic acid molecules, such as described in U.S. Pat. No. 7,312,034, the entire disclosure of which is incorporated by reference. In practicing the method, target sequences are mixed with (i) a set of forward universal e-tag primers, each containing (i) a target sequence that is complementary to one of the known selected target sequences, and an extension sequence which is unique to the target sequence of that member, (ii) one or more reverse universal e-tag primers that are complementary to said target sequences, and (iii) enzyme and nucleotide components of a primer extension reaction, to form a target-sequence reaction mixture. The mixture is first reacted under primer extension reaction conditions, to form extended, preferably amplified target sequences. The extended target sequences are then reacted under hybridization conditions with a set of electrophoretic tag (e-tag) probes, each having (i) an oligonucleotide target-binding portion or moiety that is complementary to one of the extension sequences, (ii) an electrophoretic probe having separation characteristics, e.g., electrophoretic mobility, that is unique to a given extension sequence, and (iii) a linker joining the oligonucleotide portion and the electrophoretic probe, where the linker is cleavable under selected conditions when the oligonucleotide portion of the probe is bound to a complementary target extension sequence. The target sequences with bound probes are treated under the selected conditions, to release an e-tag reporter from each e-tag probe bound to a target sequence, the released reporters are separated, e.g., electrophoretically, and the separated reporters are detected, to identify target sequences that hybridized to the probes.

In some embodiments, tags and/or labels may be attached to solid phase supports, e.g., microparticles. Molecules such as oligonucleotides, proteins, aptamers and small organic molecules may be coupled to microparticles in accordance with any of the known coupling reactions in the art. See e.g., G. T. Hermanson, Bioconjugate Techniques (Academic Press, 1996) and Ilium et al., Methods in Enzymology 112:67-84 (1985), the entire disclosures of which are incorporated herein by reference.

In some embodiments, allele-specific second reaction products are interrogated by differential melting curve analysis. This approach includes a fluorescent DNA dye, such as LCGreen® (Idaho Technology, Inc, Salt Lake City, Utah) designed to detect heteroduplexes, in a PCR amplification process to produce allele-specific second reaction products comprising the dye. The second reaction products are then subjected to melting analysis, preferably high resolution melting analysis, which involves generating a melting curve by measuring fluorescence from the DNA dye as the mixture is heated. Analysis of the melting curve identifies the alleles present based on melting temperature and melting curve shape. See, e.g., Wittwer et al., U.S. Pat. No. 7,387,887 and Dujols, U.S. Pat. No. 7,456,281, the entire disclosures of which are incorporated herein by reference. High resolution melting of small amplicons is also described in Liew et al., Clinical Chemistry 50:7 (2004), the entire disclosure of which is incorporated herein by reference. In these embodiments, the source tag, when present, may be identified by its contribution to at least the melting temperature $T_m$ of an amplicon.

In some embodiments, interrogation of reaction products may include both differential melting curve analysis and fragment size analysis.

FIG. 1A illustrates three portions of DNA molecules, designated DNA-1, DNA-2, and DNA-3. The DNA molecule consists of two long polymers, or polynucleotides, often called "strands" composed of simple units called nucleotides comprising one of four types of bases guanine ("G"), cytosine ("C"), adenine ("A"), and thymine ("T"). The strands of DNA are schematically represented in FIG. 1A as DNA-1a, 2a, 3a with complementary strands DNA-1b, 2b, 3b, respectively. Here, the "a" strand is the sense strand and the "b" strand is the anti-sense strand. Alternating sugars and phosphates form a "backbone" of the strands of DNA and are illustrated in the figures as a straight line joining the nucleotides "G", "A", "T", and "C". Each of the ends of the strands of the DNA, DNA 1-a, 2a, 3a, DNA 1-b, 2-b, 3-b, are labeled with a 3' or a 5'. The 3' and 5', by convention, indicate the orientation of the DNA strands with respect to the sugar-phosphate backbone. As discussed below, enzyme-catalyzed strand elongation proceeds in the 5'→3' direction along a DNA strand. The pairing of the complementary strands of DNA, that is strands DNA-1a with DNA-1b, DNA-2a with DNA-2b, and DNA-3a with DNA-3b is mediated by hydrogen bonding between the pairs of nucleotides, A-T and G-C, such that strands have opposite orientation. The nucleotide sequence of DNA-1b, reading from the 5' terminus, is "CTTCA ... GGGG". As illustrated, strands DNA-1a, 1b, DNA-2a, 2b, and DNA-3a, 3b have only eighteen nucleotides, however, actual human genomic strands of DNA ("gDNA") have hundreds of millions of nucleotides. The two nucleotides that are bonded together on the complementary strands are called a base pair. For example, nucleotide "G" at the 3' end of strand DNA-1a and nucleotide "C" at the 5' end of strand DNA-1b are a base pair.

FIG. 1B illustrates an allele profile 100 for the three DNA molecules, DNA-1, DNA-2, DNA-3, illustrated in FIG. 1A. An allele profile 100 is an indication of which alleles are present in the DNA molecule, DNA-1, DNA-2, DNA-3, at each of a number of polymorphisms, 1.1, 1.2, 2.1, 2.2. In the FIG. 1, there are two single polynucleotide polymorphisms (SNPs), each with two different alleles. The notation "1.2" means polymorphism "1" with allele "2" and refers to the nucleotide present on the sense strand (i.e., "a" strand). The notation "1.2" means polymorphism "1" with allele "2" and refers to the nucleotide on the anti-sense strand (i.e., "b" strand). So, the allele profile for each of the DNA molecules, DNA-1, DNA-2, DNA-3, includes which nucleotide is present for each of the two polymorphisms. For example, referring to FIGS. 1A and 1B, DNA-2, has nucleotide "G" for polymorphism 1 (see 1.2 in FIG. 1A and table 100 in FIG. 1B) and nucleotide "T" for polymorphism 2 (see 2.2 in FIG. 1A and table 100 in FIG. 1B). Another name for an "allele profile" 100 is an "attribute profile" 100 of a nucleic acid molecule, since an allelic variation is an attribute of a nucleic acid molecule.

Figure 1C:
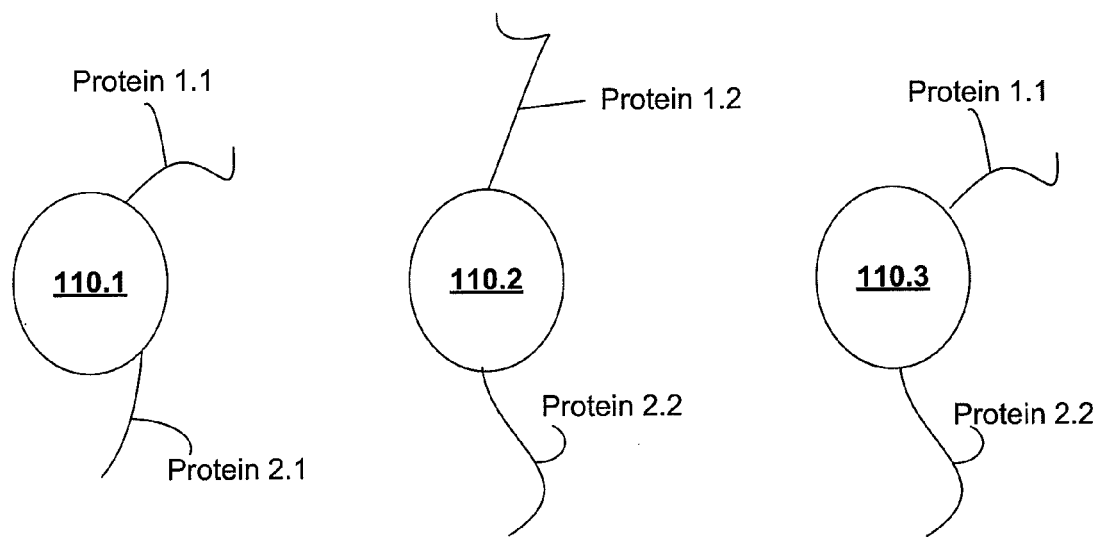
FIG. 1C schematically illustrates blood cells with proteins attached.

FIG. 1C illustrates blood cells with proteins attached on the blood cell surfaces, where the proteins are encoded by the DNA molecules of FIG. 1A. As discussed above, the proteins may be an antigen. The sequences of nucleotides G, A, T, and C of the DNA strands, DNA-1a, b, DNA-2a, b, DNA-3a, b, are used by the organism to synthesize the proteins 1.1, 1.2, 2.1, 2.2. Three nucleotides (G, A, T, and C) encode an amino acid, and the amino acids are bonded together to form the proteins 1.1, 1.2, 2.1, 2.2. For example, the portion of DNA-1 labeled 1.1 is part of the sequence of nucleotides that directs the synthesis of the protein 1.1, which is attached to blood cell 110.1. And, the portion of DNA-2 labeled 1.2 directs the synthesis of protein 1.2, which is attached to blood cell 110.2, and is different than the protein 1.1. So, determining the allele or nucleotide at polymorphism 1 can be used to infer which protein 1.1 or 1.2 will be attached to a blood cell 110 produced by the organism.

The case of a single nucleotide (G, A, T, and C) difference at a polymorphism 1, 2 of the DNA molecule has been illustrated with only two different nucleotides possible at each polymorphism. This case is called a di-allelic or bi-allelic polymorphism. Note that blood cells were illustrated in FIG. 1C, but that determining alleles may also be used to infer the antigens of other cells such as red cells, platelets and leukocytes.

As discussed above, one use of allele profiling is to determine the identity of antigens associated with proteins, such as protein 1.1, protein 2.1, protein 1.2, protein 2.2, on surfaces of blood cells 110, which are synthesized from the corresponding DNA-1, DNA-2 or DNA-3. In particular, the comparison of allele profiles of candidate blood donors with the allele profile of a recipient of blood may be used to determine whether or not the proteins 1.1, 1.2, 2.1, 2.2 on the blood cells 110 of a donor will cause an immune reaction if transfused to the recipient. For example, if the allele profile of a donor indicated the donor's blood contained blood cell 110.3 and the allele profile of a recipient indicated the recipient's blood to contain blood cell 110.1, then since proteins 1.1 match, no immune reaction would be caused by (the antigen associated with) protein 1.1, but since the donor's blood cell 110.3 has an antigen associated with protein 2.2 (encoded by DNA-3 polymorphism 2), and the recipient's blood cell has an antigen associated with protein 2.1 (encoded by DNA-1 polymorphism 2), an immune reaction may occur in the recipient. Were cell 110.3 to lack the antigen associated with protein 2.2, then donor cells 110.3 would be acceptable for transfusion to the recipient. This example illustrates that the allele profile of DNA may be used to determine whether or not the blood of a donor may cause an immune reaction in a recipient.

Figure 2:
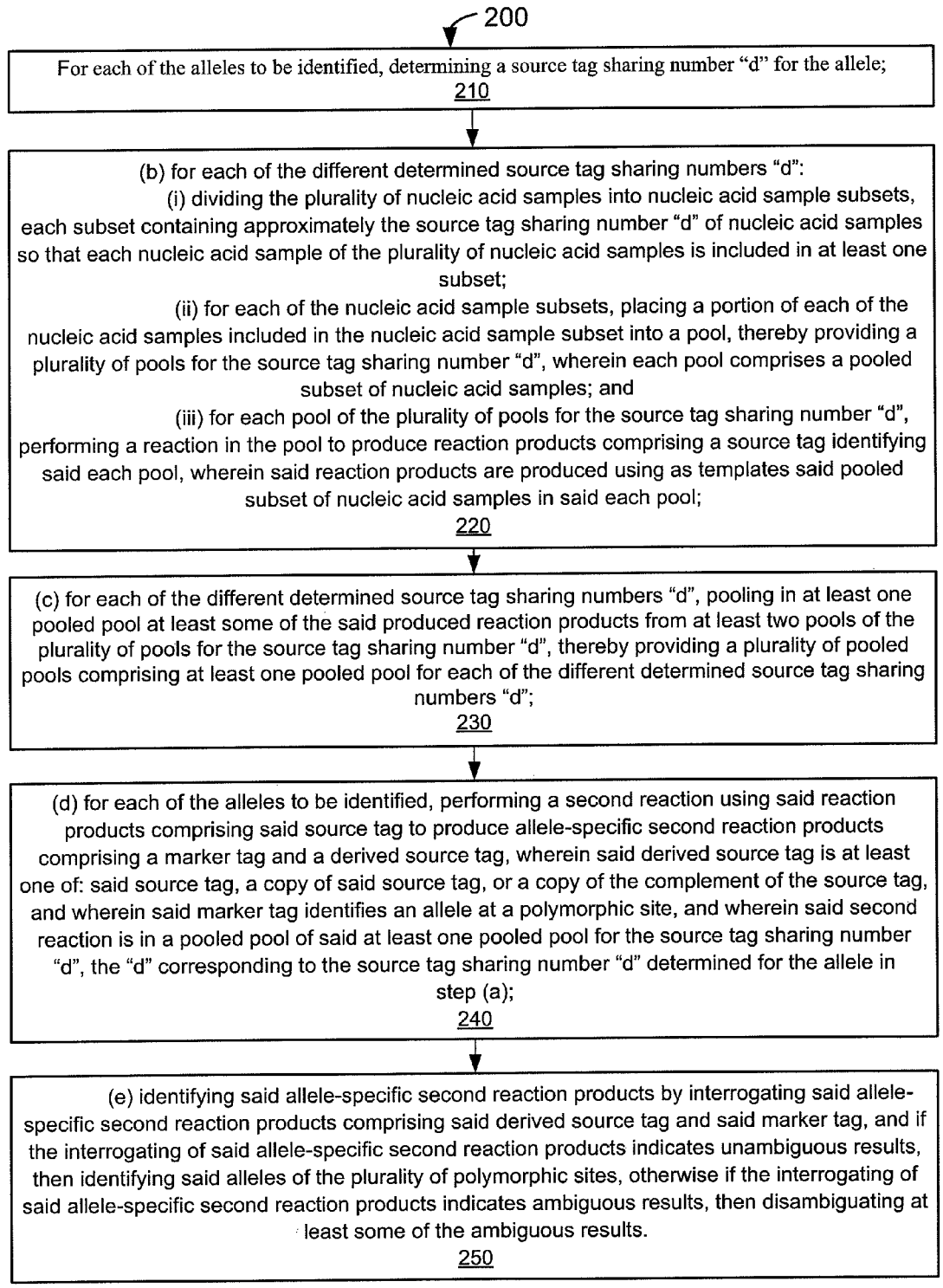
FIG. 2 schematically illustrates an embodiment of a method of determining an attribute profile for a plurality of DNA samples.

FIG. 2 illustrates an embodiment of a method of identifying alleles of a plurality of polymorphisms in a plurality of nucleic acid samples. The samples of the plurality may be sourced from different individuals.

Figure 3:
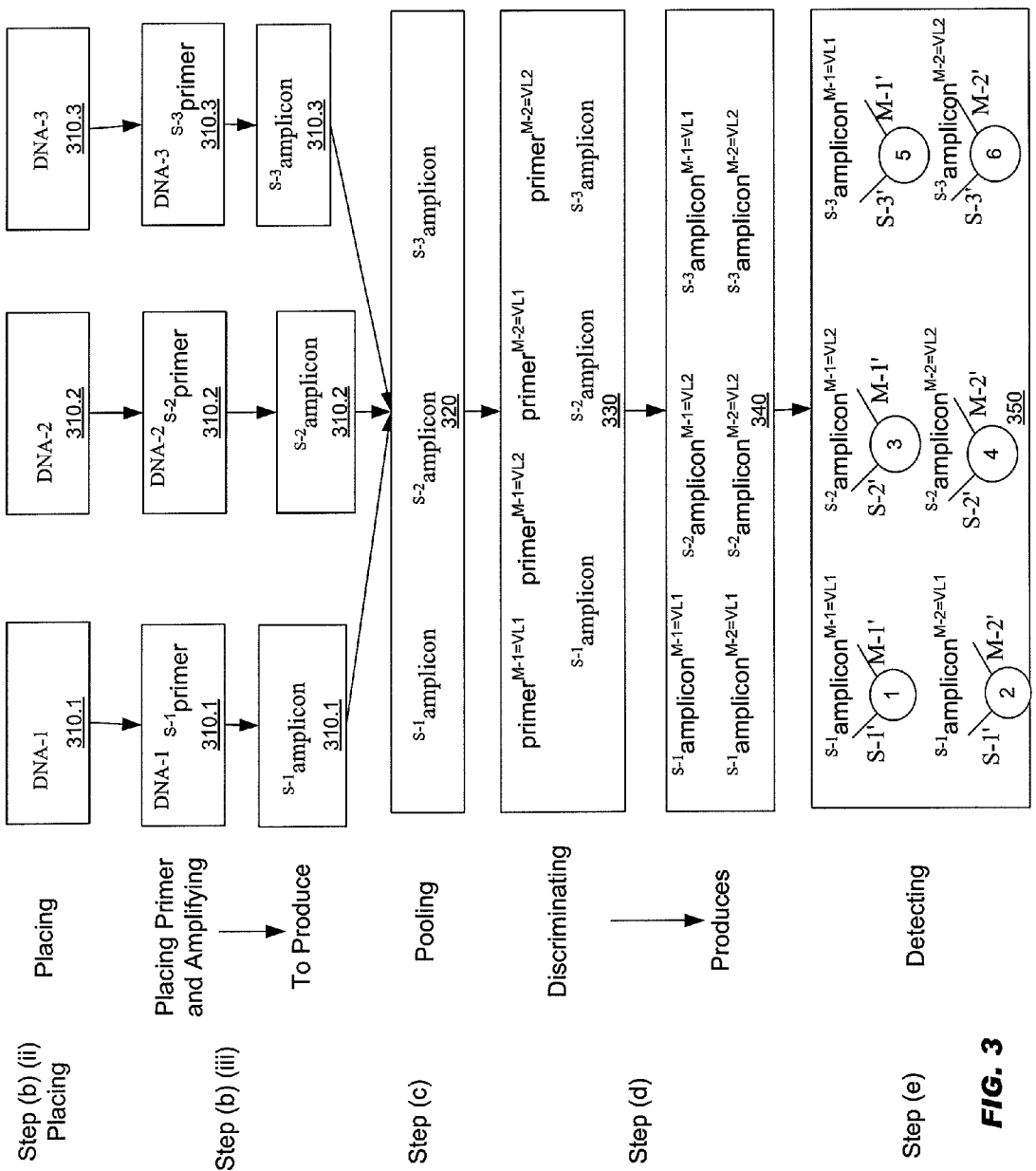
FIG. 3 schematically illustrates the operation of an embodiment of the method illustrated in FIG. 2 for the case where the alleles for only one polymorphism are being determined.

The method 200 of FIG. 2 will be explained with several examples. The first example will determine polymorphism 1 and polymorphism 2 of FIG. 1B for the nucleic acids of DNA-1, DNA-2, and DNA-3 of FIG. 1A. In this context, "determine" means to identify the particular allele of the polymorphism possessed by a nucleic acid sample. DNA-1, DNA-2, and DNA-3 represent nucleic acid samples from three individuals. The first example will illustrate how allele profile 100 of the table illustrated in FIG. 1B can be determined. In this example, the plurality of polymorphisms is "two" and the plurality of nucleic acid samples is "three," i.e. the nucleic acid samples, DNA-1, DNA-2, and DNA-3. An overview of the steps of the first example is illustrated in FIG. 3. FIGS. 2-6 illustrate additional details of the first example illustrated in FIG. 3.

The method 200 of FIG. 2 begins with step (a) For each of the alleles to be identified, determining a source tag sharing number "d" for the allele. In particular, a source tag sharing number, "d", is determined for an allele: "d" represents an approximate number of nucleic acid samples from different sources that may share a source tag in the process for determining the allele: this process, source tags, the selection of source tag sharing numbers "d", and binning are described in greater detail below. For purposes of illustration, a source tag sharing number of "d"=1 will be used for all the alleles for the following example. Other examples, described in detail below, illustrate the case d>1, that is source tag sharing numbers exceeding 1. For the first example of method 200 which is illustrated in FIGS. 2-6, the source tag sharing number "d"=1 for polymorphism 1 and "d"=1 for polymorphism 2. The source tag sharing numbers may not necessarily be determined explicitly, but implicitly by the number of nucleic acid source samples sharing source tags in the steps of method 200.

The method 200 of FIG. 2 continues with step 220 (b) for each of the different determined source tag sharing numbers "d": (i) dividing the plurality of nucleic acid samples into nucleic acid sample subsets, each subset containing approximately the source tag sharing number "d" of nucleic acid samples so that each nucleic acid sample of the plurality of nucleic acid samples is included in at least one subset. Here, as discussed above, for this example of the method 200 the source tag sharing number "d"=1 is used for both polymorphism 1 and polymorphism 2. So, the three nucleic acid samples, DNA-1, DNA-2, and DNA-3 each comprise a subset of one (1) DNA sample.

Step 220 (b) continues with (ii) for each of the nucleic acid sample subsets, placing a portion of each of the nucleic acid samples included in the nucleic acid sample subset into a pool, thereby providing a plurality of pools for the source tag sharing number "d", wherein each pool comprises a pooled subset of nucleic acid samples. Here, there are three nucleic acid sample subsets, DNA-1, DNA-2, and DNA-3. As illustrated in FIG. 3, DNA-1 is placed in pool 310.1, DNA-2 is placed in pool 310.2, and DNA-3 is placed in pool 310.3. The plurality of sample containers for source tag sharing number "d"=1 is thus represented by the group comprising 310.1, 310.2, and 310.3.

Step 220 (b) continues with (iii) for each pool of the plurality of pools for the source tag sharing number "d", performing a reaction in the pool to produce reaction products comprising a source tag identifying said each pool, wherein said reaction products are produced using as templates said pooled subset of nucleic acid samples in said each pool.

In some embodiments, step (b) (iii) may be for each pool of the plurality of pools for the source tag sharing number "d", amplifying the nucleic acid samples in the pool with primers comprising a source tag to produce amplicons comprising said source tag identifying said each pool, wherein said amplicons are produced using as templates said pooled subset of nucleic acid samples in said each pool.

Amplification may be performed by conventional methods of nucleic acid amplification, e.g. polymerase chain reaction (PCR).

The amplification is now described in greater detail. Referring to FIG. 3, 310.1, 310.2, and 310.3 represent the plurality of pools. Primers comprising a source tag identifying each pool, 310.1, 310.2, 310.3, are placed in each of the pools with the primers identifying the pools. In some embodiments, the source tags comprise so-called oligonucleotide "bar codes" as discussed below. As illustrated, the primers $^{S-1}$primer, $^{S-2}$primer, and $^{S-3}$primer are placed in respectively the pools 310.1, 310.2, 310.3. The primers, $^{S-1}$primer, $^{S-2}$primer, $^{S-3}$primer, include source tags discussed below. The notation "$^{S-1}$primer", means a primer with source tag s-1 attached to the primer.

Nucleic acid samples of the pools 310.1, 310.2, and 310.3 are then amplified to produce respectively $^{S-1}$amplicon, $^{S-2}$amplicon, and $^{S-3}$amplicon. Amplification may comprise, for example, PCR. The entire DNA molecule, DNA-1, DNA-2, does not need to be amplified, but only selected portions of the DNA molecule that include the polymorphic sites whose alleles are going to be determined. As such $^{S-1}$primer, $^{S-2}$primer, $^{S-3}$primer may each attach to the DNA molecule sequence at a selected section of the DNA molecule so that parts of the DNA molecule that contain the polymorphic sites whose alleles are going to be determined will be replicated. So, although illustrated as a single primer, $^{S-1}$primer, $^{S-2}$primer, $^{S-3}$primer, each of the primers may include a primer for each of the selected sections of the DNA molecule needed to determine the polymorphism.

The primers, $^{S-1}$primer, $^{S-2}$primer, $^{S-3}$primer, include source tags, s-1, s-2, and s-3. The source tags may be used to identify, in a later step of the method, the pool 310.1, 310.2, 310.3 of origin of the nucleic acid samples, DNA-1, DNA-2, DNA-3. So, for example, source tag s-1, which is part of $^{S-1}$primer, indicates the sample container 310.1 is the source. The source tags, s-1, s-2, s-3 may each comprise a sequence of nucleotides that are different from sequences of the DNA, DNA-1, DNA-2, DNA-3. The sequence for the source tags may be selected from a set of unique non-naturally occurring coding sequences, which may be referred to as "barcodes." The barcodes may be replicated in a later step along with the sequence of nucleotides of the DNA. See "Address/capture tags for flow-cytometry based mini-sequencing", "Kind Code A1", White, et al. (U.S. Pat. Pub. 20050147998, Jul. 7, 2005), the entire disclosure of which is incorporated herein by reference; and see, "Oligonucleotide tags for sorting and identification", Brenner, et al. (U.S. Pat. No. 6,352,828, 2004), the entire disclosure of which is incorporated herein by reference. In some embodiments, the source tag may identify the pool according to length of the source tag as is described below with electrophoresis.

In the embodiment illustrated in FIG. 3, the source tag sharing number "d"=1 is illustrated, so that only one nucleic acid sample, i.e. DNA-1, DNA-2, or DNA-3, resides in pool 310.1, 310.2, or 310.3. As discussed below, for source tag sharing numbers greater than 1, more than one nucleic acid sample, may be placed in each pool. Each of the nucleic acid samples, DNA-1, DNA-2, and DNA-3, may be from a different person or different organism. In the embodiment illustrated in FIG. 3, the nucleic acid samples, DNA-1, DNA-2, DNA-3, comprise native donor DNA from different individual nucleic acid samples, DNA-1, DNA-2, and DNA-3. The entire genome of the individual donor DNA may not be present. Alternatively, DNA-1, DNA-2, and DNA-3 may comprise a manufactured product of DNA comprising a portion of the donor holder's total DNA. Moreover, the nucleic acid samples for analysis may comprise other nucleic acid other than DNA, e.g. RNA.

Continuing with an embodiment of step 220 (b) (iii) of method 200, the nucleic acid DNA samples, (DNA-1, DNA-2, DNA-3), in the pools 310.1, 310.2, and 310.3 are then amplified using primers, $^{S-1}$primer, $^{S-2}$primer, $^{S-3}$primer, respectively, to produce amplicons, $^{S-1}$amplicon, $^{S-2}$amplicon, and $^{S-3}$amplicon, which comprise copies of at least a portion of the original DNA-1, DNA-2, and DNA-3 nucleic acid samples and further comprise source tags, s-1, s-2, s-3 respectively, wherein the source tag of an amplicon indicates the pool in which the amplicon was prepared. The notation "$^{S-1}$amplicon" means an amplicon with source tag s-1 attached. As discussed above, the notation s-1 identifies that the amplicon, $^{S-1}$amplicon, originates from pool 310.1, this source tag will be used later in the method to identify the pool. In some embodiments, any number of PCR cycles may be used for amplification generation. In some embodiments, a small number of cycles (8-10 or fewer cycles) of PCR may be used.

In general, different methods may be used to produce amplicons, $^{S-1}$amplicon, $^{S-2}$amplicon, and $^{S-3}$amplicon, in pools 310.1, 310.2, and 310.3, from the source samples of nucleic acids, which are DNA-1, DNA-2, and DNA-3, as illustrated in FIG. 3.

Alternatively, source tags may be introduced by a cut-and-paste transportation method. See e.g., U.S. Pat. No. 5,965,443, the entire disclosure of which is incorporated herein by reference. And, see Nextera™ technology product use catalogs, the entire disclosure of which is incorporated herein by reference.

Figure 4A:
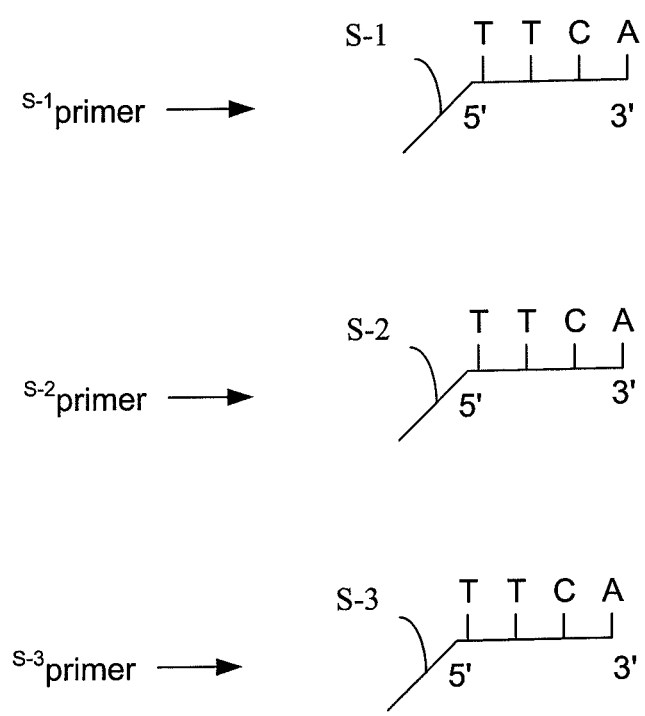
FIG. 4A schematically illustrates source tag primers.
Figure 4B:
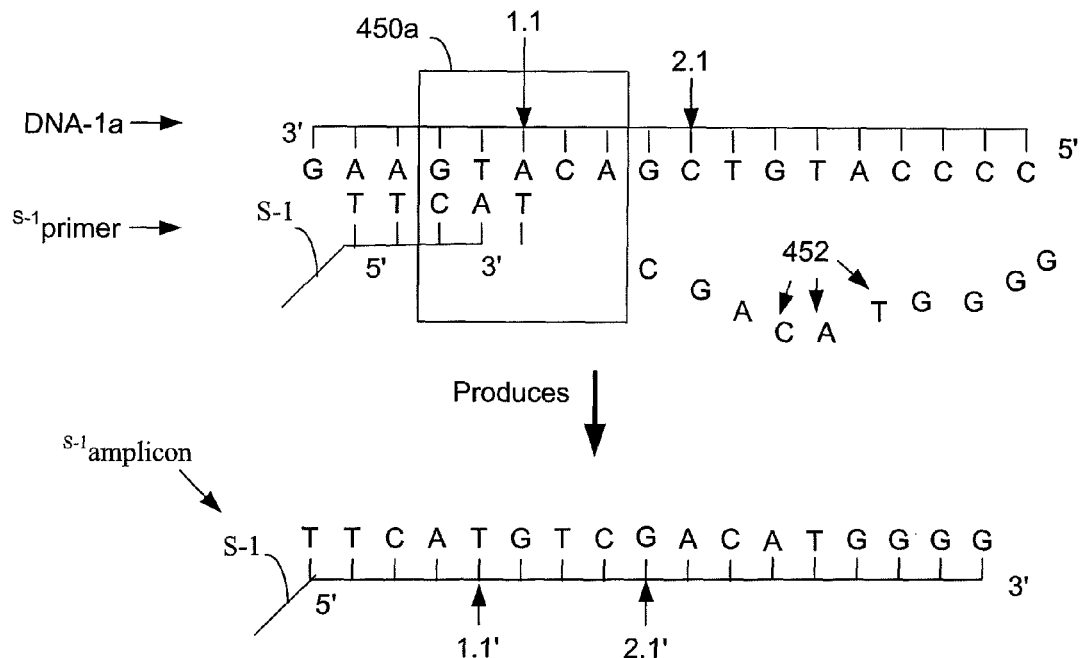
FIGS. 4B, 4C, and 4D schematically illustrate amplification by polymerase chain reaction ("PCR") where the primers $^{S-1}$primer, $^{S-2}$primer, and $^{S-3}$primer attach to the DNA strands DNA-1a (SEQ ID No. 1), DNA-2a (SEQ ID No. 3), and DNA-3a (SEQ ID No. 5), and the polymerases 450a, 450b, and 450c extend the primers $^{S-1}$primer, $^{S-2}$primer, and $^{S-3}$primer using the DNA strands as templates to produce source-tagged amplicons $^{S-1}$amplicon (nucleotides 2-18 of SEQ ID No. 2), $^{S-2}$amplicon (nucleotides 2-18 of SEQ ID No.4) and $^{S-3}$amplicon (nucleotides 2-18 of SEQ ID No. 6)

FIGS. 4A, 4B, 4C, and 4D illustrate in more detail step 220 of the method illustrated in FIG. 2 and discussed above, where PCR is used and the primers, $^{S-1}$primer, $^{S-2}$primer, and $^{S-3}$primer, attach to the DNA strands, DNA-1a, DNA-2a, and DNA-3a, and the polymerases 450a, 450b, and 450c extend the primers, $^{S-1}$primer, $^{2}$primer, and $^{S-3}$primer, using the DNA strands, DNA-1a, DNA-2a, and DNA-3a, as templates. The amplification of DNA strands DNA-1b, DNA-2b, and DNA-3b, are not illustrated in the examples. The DNA strands DNA-1a, b; DNA-2a, b; and, DNA-3a, b may be separated from their complementary strand by heating the wells 310. The primers, $^{S-1}$primer, $^{S-2}$primer, and $^{S-3}$primer (discussed above and illustrated in FIG. 4A), attach to the DNA strands, DNA-1a, DNA-2a, and DNA-3a, respectively. FIG. 4B illustrates $^{S-1}$primer attached to DNA-1a at "3'-AAGT-5" (second nucleotide from the left of the 3' end of DNA-1a). The $^{S-1}$primer attaches to complementary nucleotides with G-C and A-T being complements. Because $^{S-1}$primer comprises nucleotides "5'-TTCA-3" (the complement being "3'-AAGT-5" on DNA-1a), $^{S-1}$ primer attaches to DNA-1a at "3'-AAGT-5", which is the only place $^{S-1}$primer could attach to DNA-1a.

The polymerase 450a attaches nucleotides 452 to the 3' end of the $^{S-1}$primer and, using strand DNA-1a as a template, the polymerase 450a extends $^{S-1}$primer. Illustrated in FIG. 4B is nucleotide "T" being added to the $^{S-1}$primer by polymerase 450a. The "T" is the complement of "A". The polymerase 450a continues extending (or replicating or elongating) DNA-1a and produces the $^{S-1}$amplicon.

Only one $^{S-1}$primer is illustrated in FIG. 4B and in the well 310.1 of FIG. 3, but many primers are actually used so that many thousands of $^{S-1}$amplicons may be produced by the PCR reaction. Additionally, PCR comprises a number of cycles which may be performed a number of times to produce many $^{S-1}$amplicons. The cycles include heating and cooling which separate and join the DNA strands, DNA-1a, b. Each cycle may take several minutes.

Moreover, PCR may not replicate the entire DNA strand, but can be used to replicate only the portion of the DNA strand that includes the polymorphic sites 1 and 2. Note that $^{S-1}$amplicon (FIG. 4B) includes both of the polymorphisms 1 and 2 of DNA-1 that are being profiled, but, in general, a primer may only replicate the portion of the DNA-1 strand needed to identify a single polymorphism, so different primers may need to be used for each polymorphism. Note that $^{S-1}$amplicon is the complement of DNA strand DNA-1a and that $^{S-1}$amplicon does not include the nucleotide "C" which is the complement of the first nucleotide "G" next to the 5' end of the DNA strand DNA-1a. $^{S-1}$amplicon does not include the "C" nucleotide because the polymerase 450a only builds $^{S-1}$primer from the 3' end of $^{S-1}$primer, and the $^{S-1}$primer attaches after the "C" nucleotide. The amplicon $^{S-1}$amplicon does not need the "C" nucleotide since it is not part of either of the polymorphisms 1.1, 2.1.

Figure 4C:
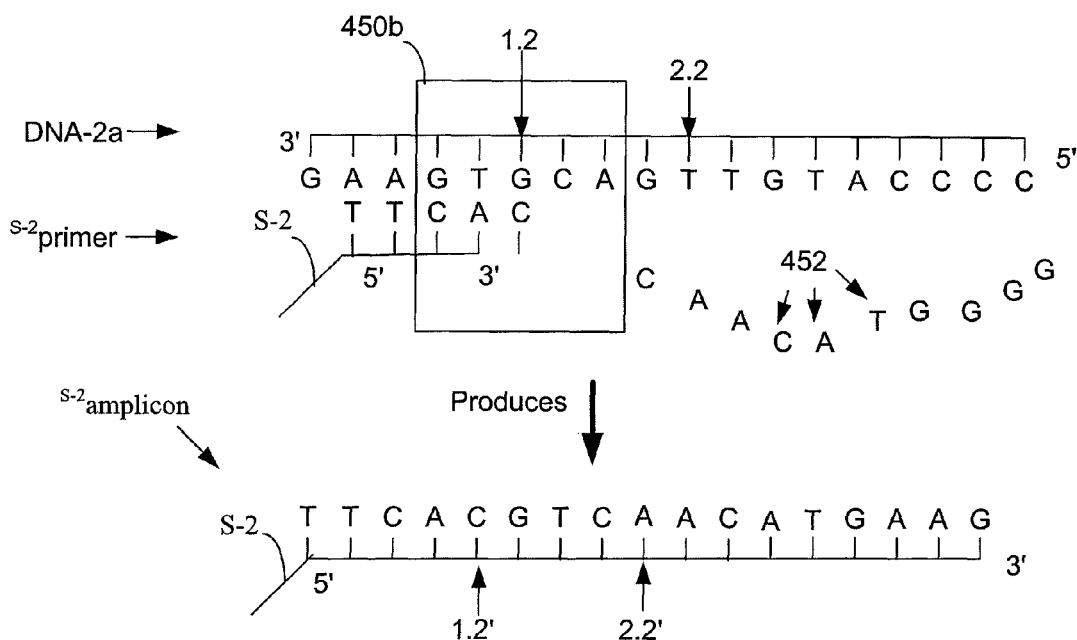
Figure 4D:
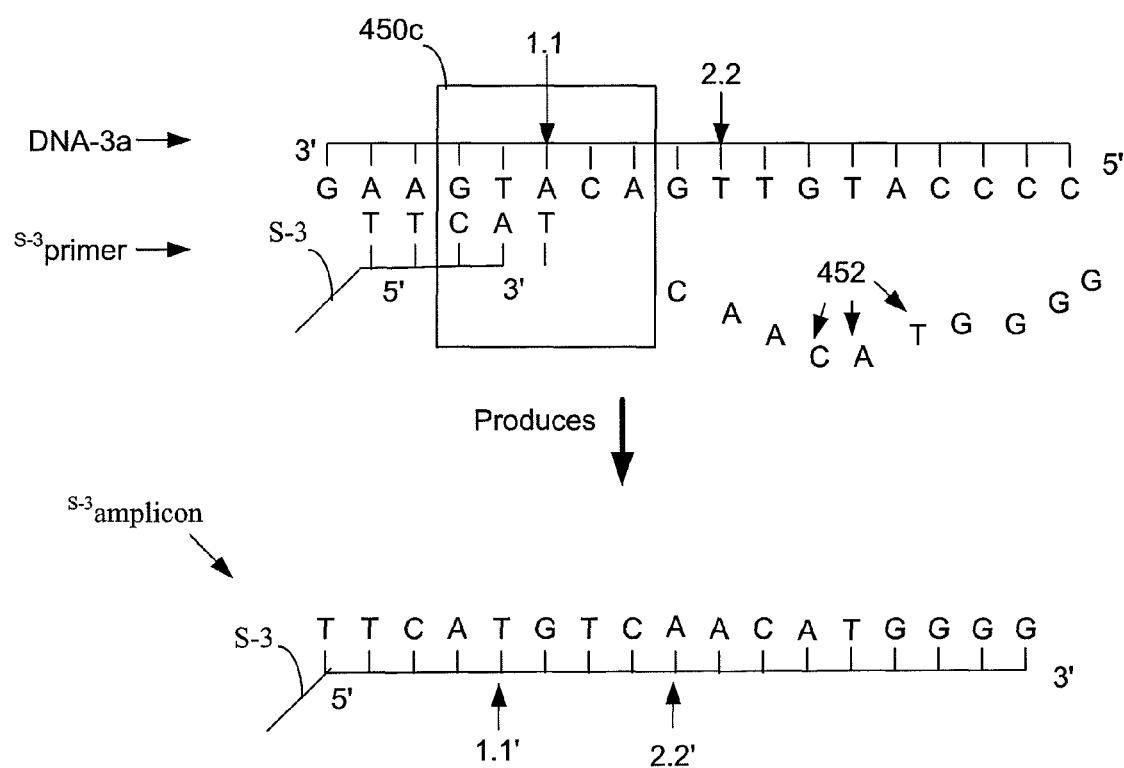

FIGS. 4C and 4D illustrate how $^{S-2}$amplicons and $^{S-3}$amplicons are produced, which is the same method as for producing the $^{S-1}$amplicons illustrated in FIG. 4B.

The method 200 of FIG. 2 continues with step 230 (c) for each of the different determined source tag sharing numbers "d" pool in at least one pooled pool at least some of the said produced reaction products from at least two pools of the plurality of pools for the source tag sharing number "d". This then provides a plurality of pooled pools comprising at least one pooled pool for each of the different determined source tag sharing numbers "d".

In the current example, there is only one source tag sharing number "d" and it is equal to 1. As illustrated in FIG. 3, a portion of each of 310.1, 310.2, and 310.3, respectively, $^{S-1}$amplicon, $^{S-2}$amplicon, and $^{S-3}$amplicon is pooled in pooled pool 320 thereby providing a pooled pool for "d"=1. The amplicons may be pooled by physically combining aliquots of the source samples in the pools 310.1, 310.2, and 310.3 into pooled pool 320.

The method 200 of FIG. 2 continues with step 240 (d) for each of the alleles to be identified, performing a second reaction using said reaction products comprising said source tag to produce allele-specific second reaction products comprising an marker tag and a derived source tag. The derived source tag may be at least one of: said source tag, a copy of said source tag, or a copy of the complement of the source tag. The marker tag indicates a specific attribute. Thus, the marker tag uniquely identifies an allele at a polymorphic site. The second reaction may be in said pooled pool for the source tag sharing number "d" with the "d" corresponding to the source tag sharing number "d" determined for the allele in step (a).

In the current example, the source tag sharing number "d" is equal to 1. In some embodiments, step 240 (d) comprises amplifying amplicons in the pooled pool for the source tag sharing number "d" with allele-specific primers the allele-specific primers comprising a marker tag with the reaction products in the pooled pool serving as templates for forming allele-specific amplification products. The allele-specific amplification products comprise said marker tag and said source tag.

Figure 5A:
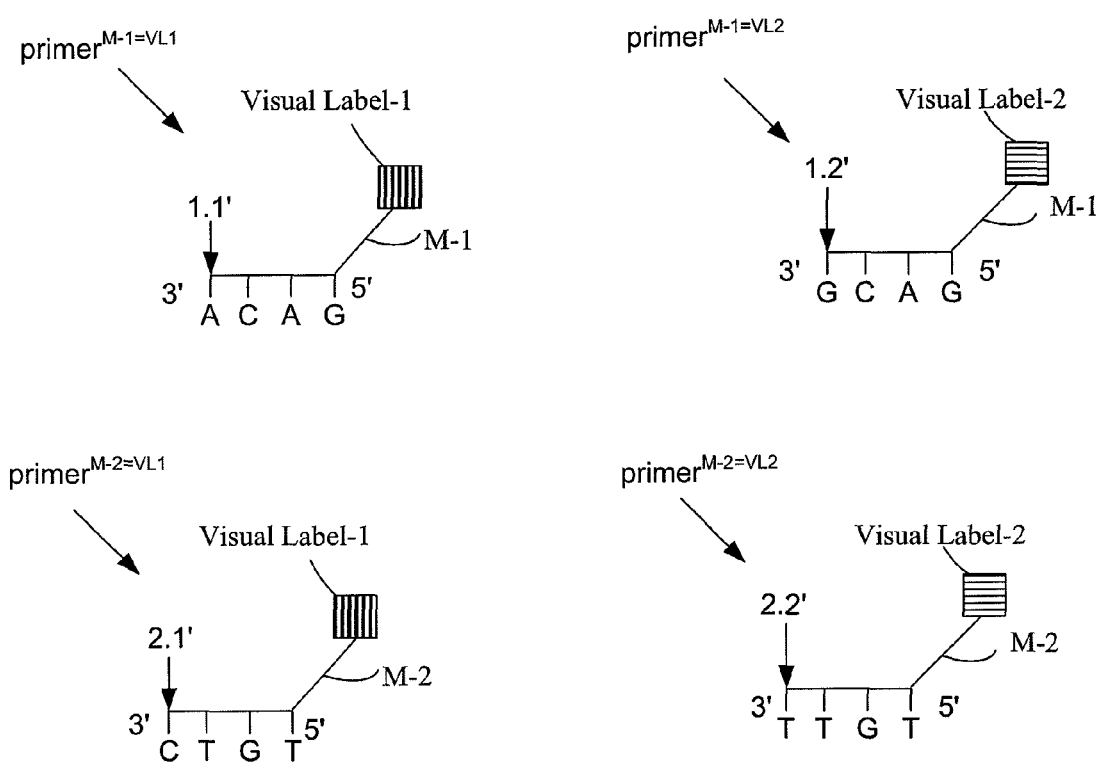
FIG. 5A schematically illustrates allele-specific primers with visual labels for use in an embodiment of method 200.

In some embodiments, for discriminating the alleles in the pooled plurality of source samples, as illustrated in FIG. 3, allele specific primers primer$^{M-1=VL1}$, primer$^{M-1=VL2}$, primer$^{M-2=VL1}$, and primer$^{M-2=VL2}$ are added to the pooling container 330. Alternatively, the allele specific primers, primer$^{M-1=VL1}$, primer$^{M-1=VL2}$, primer$^{M-2=VL1}$, and primer$^{M-2=VL2}$, can be added to containers, 310.1, 310.2, and 310.3, prior to step 240. FIG. 5A illustrates visual label-bearing allele-specific primers for use in an embodiment of step 240 (d) of method 200. Alleles are discriminated in that different alleles produce different amplicons with different visual labels.

The allele specific primers are primers that may be used to produce copies of at least part of amplicons, $^{S-1}$amplicon, $^{S-2}$amplicon, and $^{S-3}$amplicon, if the amplicons comprise the specific allele that the allele specific primer, (primer$^{M-1=VL1}$, primer$^{M-1=VL2}$, primer$^{M-2=VL1}$, and primer$^{M-2=VL2}$), was designed to detect as discussed below.

FIG. 5A illustrates the allele specific primers primer$^{M-1=VL1}$, primer$^{M-1=VL2}$, primer$^{M-2=VL1}$, and primer$^{M-2=VL2}$. FIGS. 5B-5G and 6 illustrate how the allele specific primers may be used to determine an allele profile of a portion of a DNA molecule or a portion of an amplicon of the DNA molecule. Allele specific primers, primer$^{M-1=VL1}$, primer$^{M-1=VL2}$, primer$^{M-2=VL1}$, and primer$^{M-2=VL2}$ include marker tags M-1 or M-2 and visual label 1 (VL1) or visual label 2 (VL2). The combination of marker tag and visual label identifies a specific allele. The marker tags M-1 or M-2 may be used to identify the polymorphic site to which a primer is directed, for example polymorphic sites 1 or 2. Barcodes may be used for the marker tags M-1 or M-2 just as barcodes were used for the source tags as discussed above. The visual label-1 and visual label-2 may be used to determine the nucleotide at the polymorphic site, for example, for polymorphism 1, 1.1 ("A") or 1.2 ("G") (as in Table 100), and thus to identify the allele at that site. In embodiments, 1.1 ("A") may be designated as "Normal" and 1.2 ("G") may be designated as "Variant." The visual label-1 and visual label-2 may be fluorescent dyes such as Cy5, Cy7, or ALEXA or other dyes. The visual label-1 and visual label-2 may be optically distinguishable. For example, visual label-1 may be green (illustrated with vertical lines in FIG. 5A) and visual label-2 may be red (illustrated with horizontal lines in FIG. 5A).

A combination of marker tag and visual label uniquely identifies an allele at a specific polymorphic site. For example, the allele-specific primer$^{M-1=VL1}$ may be directed to allele "T" at polymorphic site 1: primer$^{M-1=VL1}$ is made with nucleotide sequence "3-ACAG-5" so that primer$^{M-1=VL1}$ will only bind to a portion of the DNA strand at polymorphic site 1 and will be elongated only if its 3' terminal nucleotide ("A") is complementary to the nucleotide ("T") at the polymorphic or variable site.

Figure 5B:
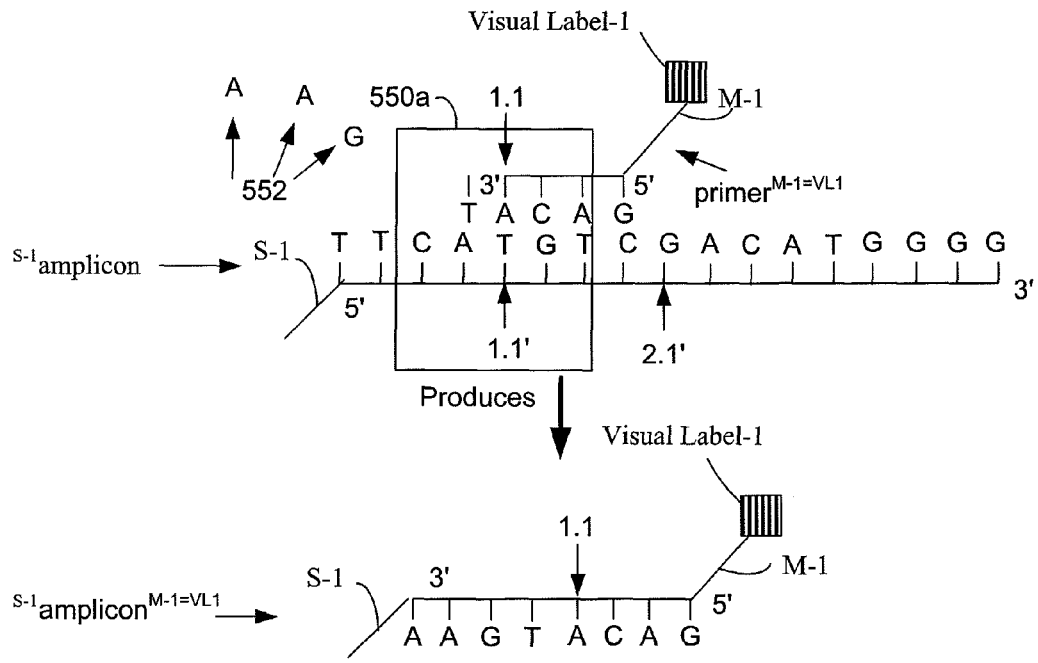
FIG. 5B schematically illustrates primer$^{M-1=VL1}$ attaching to $^{S-1}$amplicon (nucleotides 2-18 of SEQ ID No. 2) and a polymerase extending primer$^{M-1=VL1}$ using the $^{S-1}$amplicon as a template to produce $^{S-1}$amplicon$^{M-1-VL1}$ (nucleotides 10-17 of SEQ ID No. 1)

So, for example, illustrated in FIG. 5B is primer$^{M-1=VL1}$ attaching to $^{S-1}$amplicon because $^{S-1}$amplicon has an "T" at the polymorphic site 1 of DNA-1b (see FIG. 1 and FIG. 4B where DNA-1b was amplified into $^{S-1}$amplicon). The M-1 tag of primer$^{M-1=VL1}$ can then be used to determine that the amplicon includes polymorphism 1, and the visual-label-1 can be used to determine that nucleotide "T" is at polymorphic site 1.

Figure 5C:
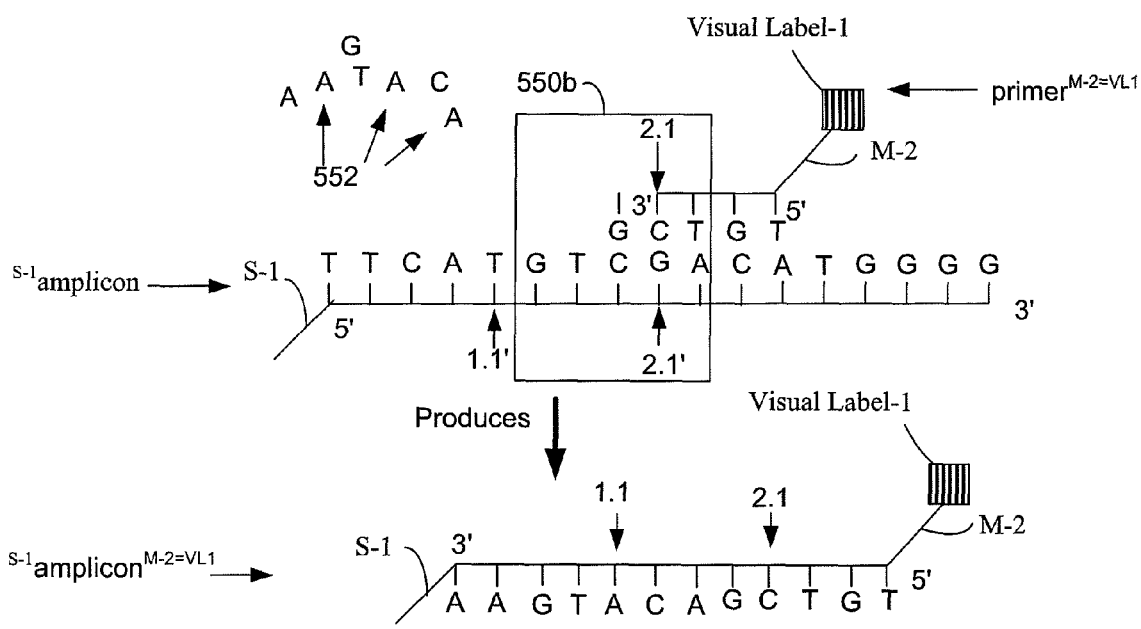
FIGS. 5C-G similarly illustrate attribute specific primers attaching to source-tag amplicons (nucleotides 2-18 of SEQ ID No. 2 in FIG. 5C; nucleotides 2-18 of SEQ ID No.4 in FIGS. 5D and 5E; and nucleotides 2-18 of SEQ ID No. 6 in FIGS. 5F and 5G) and polymerases extending the attribute specific primer using the source-tag amplicon as a primer to produce amplicons (nucleotides 6-17 of SEQ ID No. 1 in FIG. 5C; nucleotides 10-17 of SEQ ID No. 3 in FIG. 5D; nucleotides 6-17 of SEQ ID No. 3 in FIG. 5E; nucleotides 10-17 of SEQ ID No. 5 in FIG. 5F; and nucleotides 6-17 of SEQ ID No. 5 in FIG. 5G)
Figure 5D:
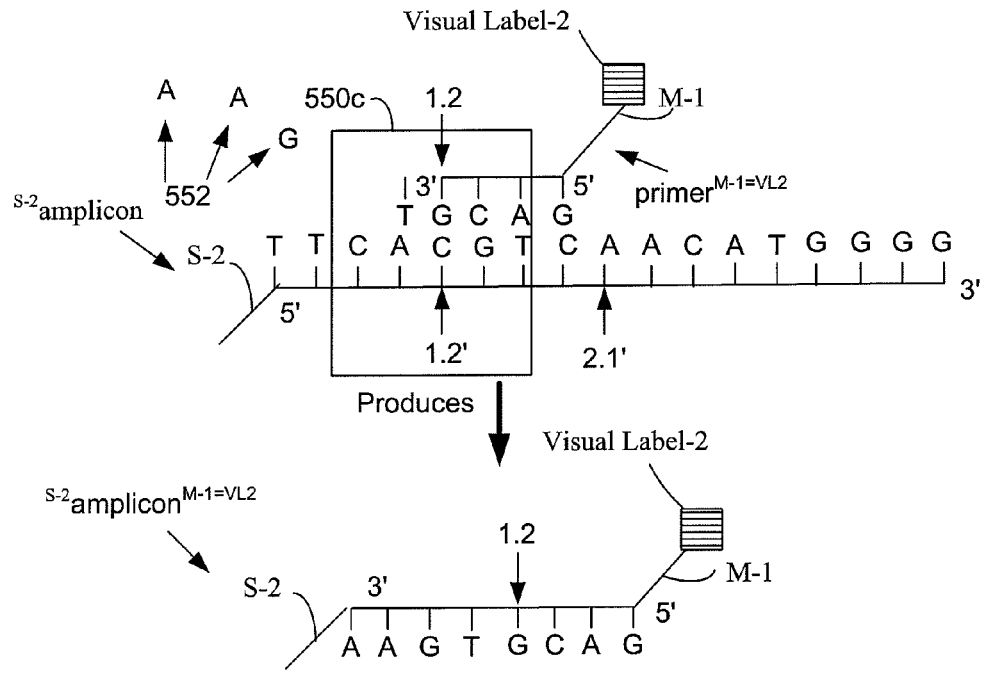
Figure 5E:
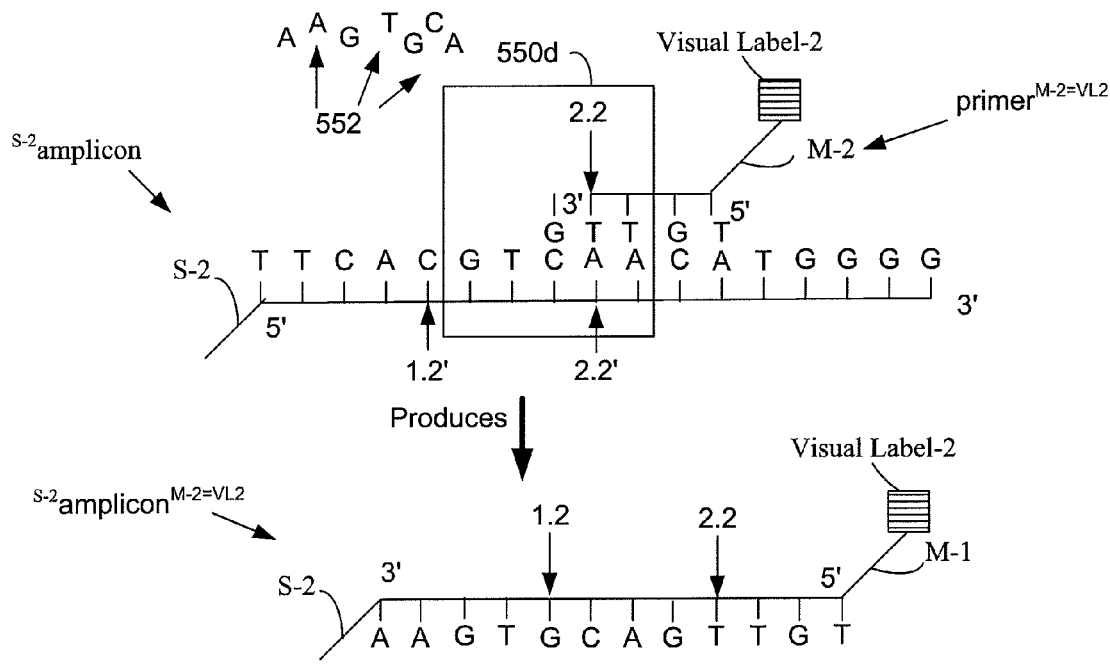

Similarly, as illustrated in FIG. 5D, primer$^{M-1=VL2}$ has a nucleotide sequence of "3'-GCAG-5'" for attaching to a DNA strand or amplicon at polymorphism 1 if it has value "C" at polymorphism 1. Similarly, as illustrated in FIG. 5C, primer$^{M-2=VL1}$ nucleotide sequence of "3'-CTGT-5'" for attaching to a DNA strand or amplicon at polymorphism 2 if it has a value of "G". Similarly, as illustrated in FIG. 5E, primer$^{M-2=VL2}$ has nucleotide sequence of "3'-TTGT-5'" for attaching to a DNA strand or amplicon at polymorphism 2 if it has a value of "A".

By pooling all four primers primer$^{M-1=VL1}$, primer$^{M-1=VL2}$, primer$^{M-2=VL1}$, and primer$^{M-2=VL2}$ in pooling container 330, amplicons will be produced that indicate the allele at polymorphic sites 1 and 2 for each of DNA-1, DNA-2, and DNA-3.

FIG. 5B illustrates primer$^{M-1=VL1}$ attaching to $^{S-1}$amplicon and polymerase 550a extending primer $^{M-1=VL1}$ using the $^{S-1}$amplicon as a template. As discussed above, primer$^{M-1=VL1}$ was designed to only attach to amplicons that have allele "T" at the polymorphic site 1. Illustrated in FIG. 5B is nucleotide "T" being added to the primer$^{M-1=VL1}$. The polymerase 550a continues replicating (or extending) $^{S-1}$amplicon using nucleotides 552 and produces the $^{S-1}$amplicon$^{M=VL1}$. $^{S-1}$amplicon$^{M-1=VL1}$ can then be used to determine that DNA-1 has nucleotide "t" for polymorphic site 1 as will be discussed below. Note that $^{S-1}$amplicon$^{M-1=VL1}$ comprises source tag s-1 because source tag s-1 which is a sequence of nucleotides so the polymerase 550a copies source tag s-1. Note that primer$^{M-1=VL1}$, primer$^{M-1=VL2}$, primer$^{M-2=VL1}$, and primer$^{M-2=VL2}$ are all present in amplicon in pooling container 330 (of FIG. 3), but that only primer$^{M-1=VL1}$ and primer$^{M-2=VL1}$ can attach to $^{S-1}$amplicon.

Figure 5F:
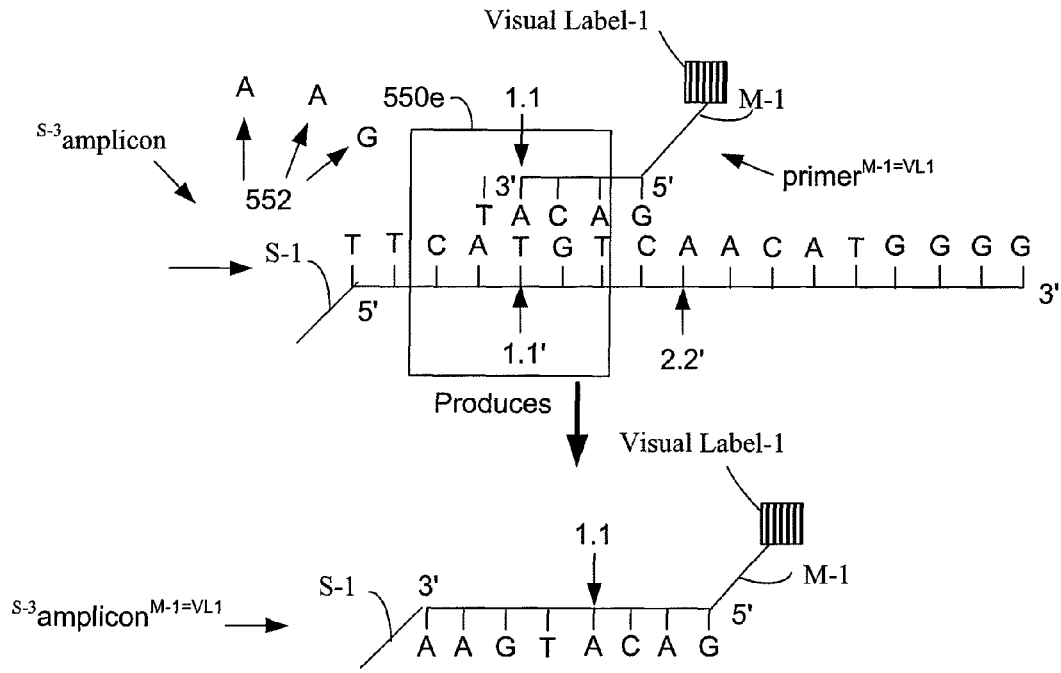
Figure 5G:
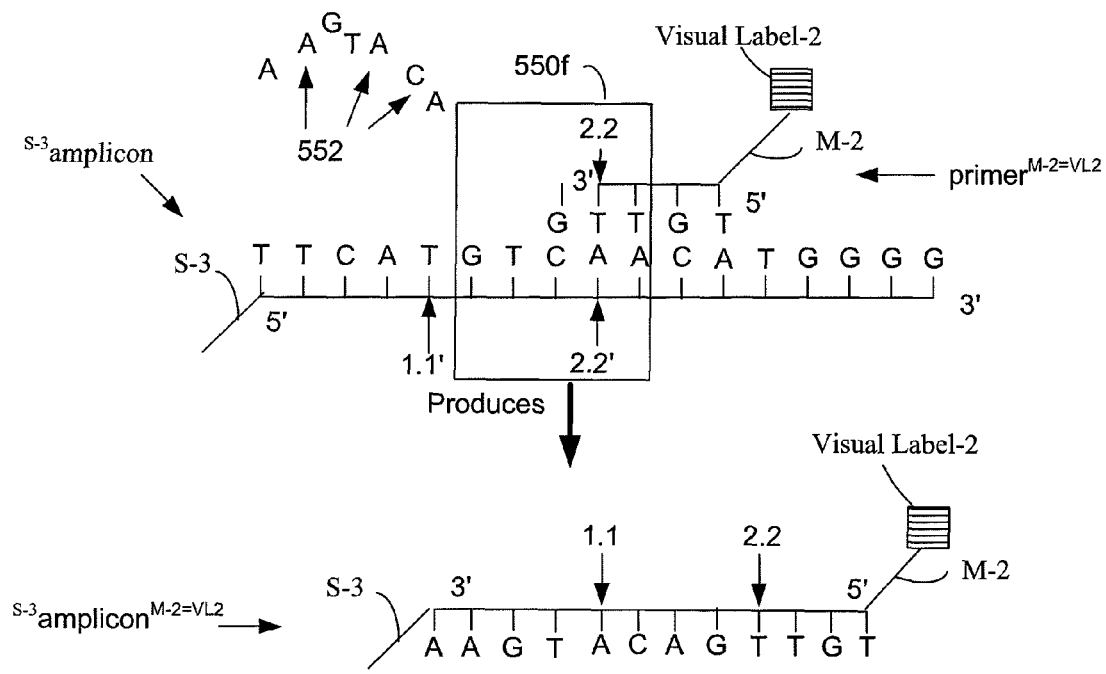

FIG. 5C similarly illustrates primer$^{M-2=V''}$ attaching to $^{S-1}$amplicon and PCR being used to produce $^{S-1}$amplicon$^{M-2=VL1}$FIG. 5D similarly illustrates primer$^{M-1=VL2}$ attaching to $^{S-2}$amplicon and PCR being used to produce $^{S-2}$amplicon$^{M-1=VL2}$. FIG. 5E similarly illustrates primer$^{M-2=VL2}$ attaching to $^{S-2}$amplicon and PCR being used to produce $^{S-2}$amplicon$^{M-2=VL2}$. FIG. 5F similarly illustrates primer$^{M-1=VL2}$ attaching to $^{S-3}$amplicon and PCR being used to produce $^{S-3}$amplicon$^{M-1=VL2}$. FIG. 5G similarly illustrates prirrler$^{M-2=VL1}$ attaching to $^{S-3}$amplicon and PCR being used to produce $^{S-3}$Amplicon$^{M-2=VL1}$. Notice that in pooling container 340 (FIG. 3) amplicons were only produced if a DNA sample has a polymorphism. For example, for DNA-1, $^{S-1}$amplicon$^{M-1=VL1}$ and a $^{S-1}$amplicon$^{M-2=VL1}$ were produced corresponding to polymorphism "A" 1.1 (FIG. 1A) and polymorphism "C" 2.1, respectively.

The method 200 of FIG. 2 continues with step 250 (e) identifying said allele-specific second reaction products by interrogating said derived source tag and said marker tag of said products, and if the interrogating of the derived source tag and the marker tag indicate unambiguous results, then identifying said alleles of the plurality of polymorphic sites, otherwise if the interrogating of the derived source tag and the marker tag indicate ambiguous results, then disambiguating the ambiguous results.

FIG. 3 illustrates how some embodiments identify allele specific amplification products, which are amplicons comprising source and marker tags. The alleles are identified, using microparticles 1, 2, 3, 4, 5, 6, also referred to as "beads" or "microbeads", typically 1 um or several urn in diameter, in container 350. The microparticles comprise attached oligonucleotides probes, hereinafter referred to as "capture probes." A capture probe comprises at least one nucleotide sequence, with each nucleotide sequence being complementary to the nucleic acid sequence of a source tag and/or a marker tag. The microparticles also comprise a fluorescent label, or mixture of such labels differing in color, that identifies the capture probes attached to the microparticle. The fluorescent label may comprise an encoded fluorescence such as described in U.S. Pat. No. 7,498,054, entitled "METHOD FOR CONTROLLING SOLUTE LOADING OF POLYMER MICROPARTICLES", the entire disclosure of which is incorporated herein by reference or U.S. Pat. No. 7,083,914, entitled "Color-Encoding AND IN-SITU INTERROGATION OF MATRIX-COUPLED CHEMICAL COMPOUNDS", the entire disclosure of which is incorporated herein by reference. The amplification products may be identified because they anneal to complementary capture probes on the microparticles 1, 2, 3, 4, 5, 6, and the marker tags on the amplification products also comprise fluorescent labels. The microparticle fluorescent tag can be used to identify the polymorphism and the fluorescent tag on the amplification product can be used to identify the allele. The following explains microparticle-mediated allele identification in more detail.

Figure 6A:
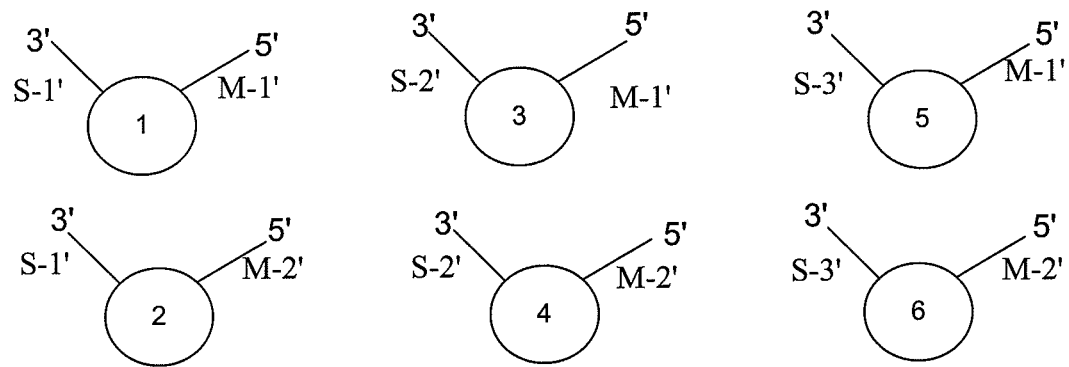
FIG. 6A schematically illustrates microparticles used to determine alleles.
Figure 6B:
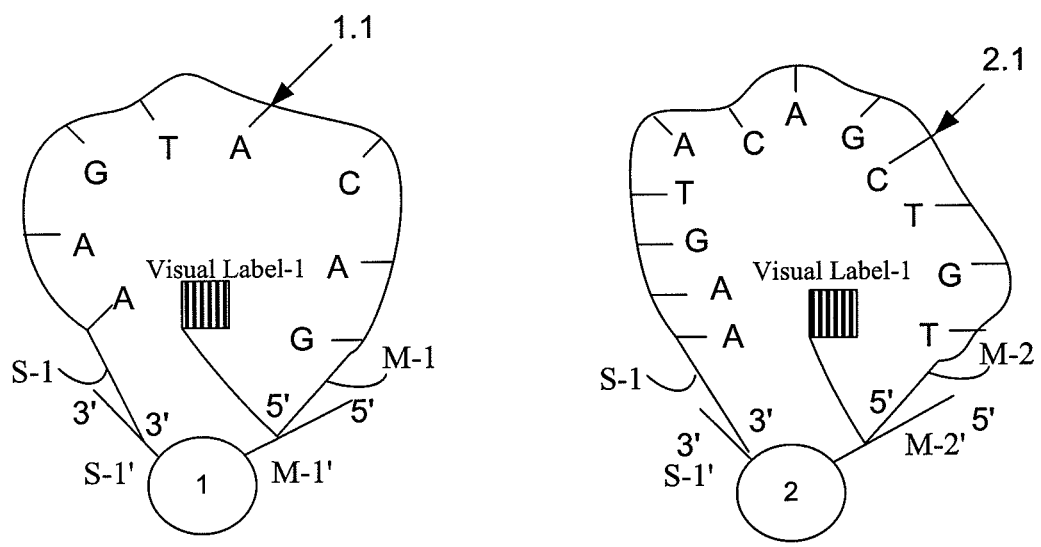
FIGS. 6B, 6C, 6D, and 6E schematically illustrate microparticle designs.

FIG. 6A illustrates microparticles 1, 2, 3, 4, 5, 6, comprising a tag such as encoded fluorescent tags so that individual microparticles can be distinguished from one another. The microparticles 1, 2, 3, 4, 5, 6 also comprise capture probes S-1' and M-1'. Each capture probe comprises at least one nucleotide sequence complementary to a nucleotide sequence present in either a source tag and/or a marker tag so that the corresponding amplicon will attach to the microparticle, by annealing to the capture probe on the microparticle. The produced amplicons, $^{S-1}$amplicon$^{M-1=VL1}$, $^{S-1}$amplicon$^{M-2=VL1}$, $^{S-2}$amplicon$^{M-1=VL2}$, $^{S-2}$amplicon$^{M-2=VL2}$, $^{S-3}$amplicon$^{M-1=VL2}$, $^{S-3}$amplicon$^{M-2=VL1}$, anneal to the respective microparticles 1, 2, 3, 4, 5, 6 comprising the correct capture probe or capture probes. The microparticle tag and the visual label of the amplicon is read to determine the "allele" at each of the polymorphic sites 1 and 2. For example, illustrated in FIG. 6B is $^{S-1}$amplicon$^{M-1=VL1}$ attached (or annealed) to microparticle 1. Microparticle 1 comprises a s-1' capture probe which is the complement of source tag s-1. Microparticle 1 also comprises capture probe M-1' which is the complement of marker tag M-1. Microparticle 1 will capture the amplicon comprising source tag S-1 and marker tag M-1 ($^{S-1}$amplicon$^{M-1=VL1}$). The allele at polymorphic site 1 can be determined based on the value of the visual label, which in this case is visual-label 1. The allele at polymorphic site 1 is 1 (or "A") for DNA-1, which agrees with table 100. This is determined as follows. The site is determined as polymorphic site 1 because the marker tag on the amplicon is marker tag "M-1." It is determined that the $^{S-1}$amplicon$^{M-1=VL1}$ was produced from DNA-1 because the $^{S-1}$amplicon$^{M-1=VL1}$ comprises source tag "S-1", which indicates that the $^{S-1}$amplicon$^{M-1=VL1}$ originated from sample container 310.1, where DNA-1 was placed. Additionally, illustrated in FIG. 6B is $^{S-1}$amplicon$^{M-2=VL1}$ attached (or annealed) to microparticle 2. Microparticle 2 comprises a capture probe s-1' which is the complement of source tag s-1. Microparticle 2 also comprises capture probe M-2' which is the complement of marker tag M-2. Microparticle 2 will capture the amplicon comprising source tag S-1 and marker tag M-1 ($^{S-1}$amplicon$^{M-2=VL1}$). The allele at polymorphic site 2 can be determined based on the value of the visual label, which in this case is visual-label 1. The allele at polymorphic site 2 is 1 (or "C") for DNA-1, which agrees with table 100. This is determined as follows. The site is determined as polymorphic site 1 because the marker tag on the amplicon is marker tag "M-2." It is determined that the $^{S-1}$ampliconm$^{M-2=VL1}$ was produced from DNA-1 because the $^{S-1}$amplicon$^{M-2=VL1}$ comprises source tag "S-1", which indicates that the $^{S-1}$amplicon$^{M-2=VL1}$ originated from sample container 310.1, where DNA-1 was placed.

An advantage of the microparticle having an attached capture probe complementary to a selected source tag and another capture probe complementary to a selected marker tag is that amplicons comprising both the selected source and marker tag will bind to the microparticle via the microparticle's capture probes with high affinity. The amplicons comprising both a source tag and marker tag will display higher affinity for the capture probes on a microparticle (hence "crowd out") residual primers (and/or amplicons) which comprise only a source tag, or residual allele-specific primers comprising only a marker tag.

Thus, in the embodiment illustrated above, the attribute profile of DNA-1, DNA-2, and DNA-3 can be determined for polymorphism 1 and polymorphism 2.

In embodiments, the source-coded and marker-coded amplicons lacking a visual marker may anneal to a microparticle. The product of the amplicon annealing to the microparticle can be detected, which may be used to determine an allele of the nucleic acid sample. For example, in the example above, an allele-specific amplicon is constructed comprising a marker tag M-1-1 that specifically indicates the presence of allele 1 at polymorphic site 1, $^{S-1}$amplicon$^{M-1-1}$. A microparticle could then be produced comprising capture probes S-1' and M-1-1', which are the complements of source tag s-1 and marker tag M-1-1, respectfully. The microparticle with capture probes S-1' and M-1-1' will capture the amplicon comprising source tag S-1 and marker tag M-1-1 ($^{S-1}$amplicon$^{M-1-1}$). The presence of the microparticle with capture probes S-1' and M-1-1' attached to $^{S-1}$amplicon$^{M-1-1}$ can be detected. And, since $^{S-1}$amplicon$^{M-1-1}$ would only have been produced if DNA-1 had allele 1 at polymorphism 1, it can be determined that DNA-1 has allele 1 at polymorphism 1. Thus by encoding both the polymorphic site and the allele in the marker tag, it is possible to determine alleles without the use of fluorescence tags.

Additionally, if only a single polymorphic site is being determined in a pool then the marker tag, for example M-1, need only encode the allele at the polymorphic site. For example, in the example above, an allele-specific amplicon is constructed comprising a marker tag M-1-1 that specifically indicates the presence of allele 1 in a pool where only polymorphic site 1 is being tested, $^{S-1}$amplicon$^{M-1}$. A microparticle can then be produced comprising capture probes S-1" and M-1", which are the complements of source tag S-1 and marker tag M-, respectfully. The microparticle with capture probes S-1' and M-1' will capture the amplicon comprising source tag S-1 and marker tag M-1. The presence of the microparticle with capture probes S-1' and M-1' attached to $^{S-1}$amplicon$^{M-1}$ can be detected. And, since $^{S-1}$amplicon$^{M-1}$ would only have been produced if DNA-1 had allele 1 at polymorphism 1, it can be determined that DNA-1 has allele 1 at polymorphism 1.

In some embodiments, microparticles are not used, but rather the produced amplicons comprise source tags and marker tags that confer differential electrophoretic mobility. The amplicons are detected in an electrophoretic mobility assay as discussed further below.

In some embodiments, molecular beacons designed to detect designated source tag and marker tag combinations on amplicons may be used. The beacons may be color-coded to distinguish individual species beacon.

In some embodiments, capture probes complementary to source tags and/or marker tags are provided on separate spectrally distinguishable nanoparticles so that two nanoparticles will attach to the produced amplicons containing the target source tag and maker tag. Because of the specific combination of source tag and marker tag, there will be a specific dual-color signature that may be used to identify the source tag and marker tag (see manufacturing instructions for use of Qdot™ Nanocrystals, Invitrogen, Carlsbad, Calif.).

In some embodiments, gDNA may be extracted from samples prior to step 210. The gDNA may be extracted separately for each sample. In some embodiments, the individual samples may be pooled and the gDNA extracted from the pooled samples, when it is intended that pooled gDNA will receive source-tags comprising the same barcode.

Figure 6C:
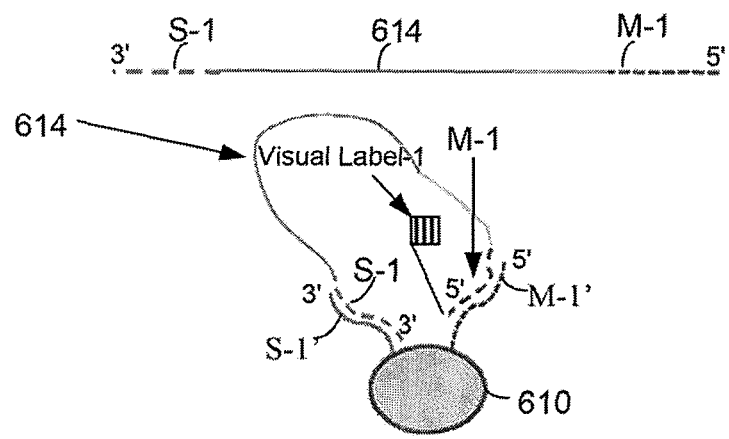
Figure 6D:
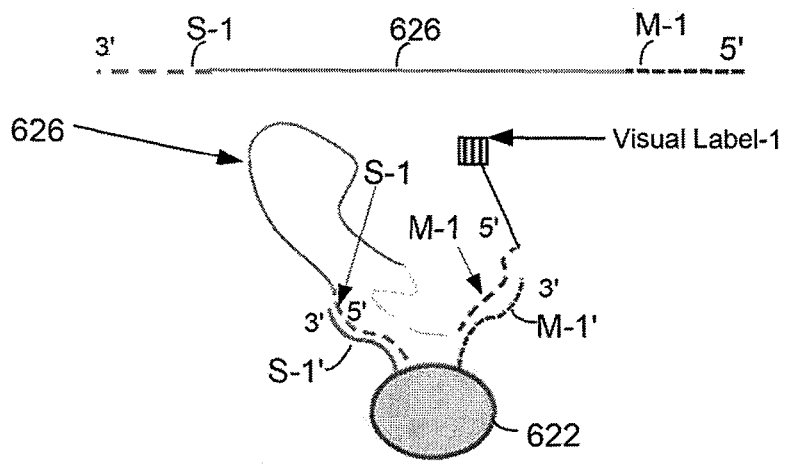
Figure 6E:
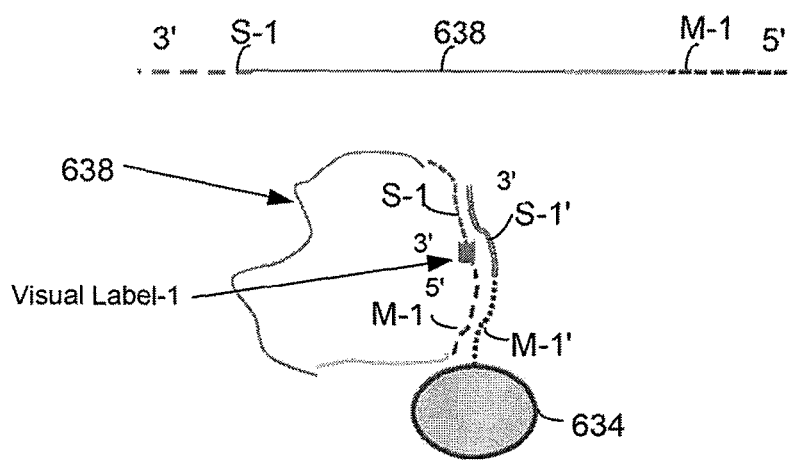

FIGS. 6C, 6D, and 6E illustrate microparticle designs that may be used to identify the amplicons produced in step 230 (FIG. 2). The allele-specific amplification or hybridization product comprising an marker tag and/or source tag anneal to the capture probes on the microparticles which enables identifying those products.

FIG. 6C illustrates a design for the microparticles in FIG. 6B. The amplicon 614, here represented as a line rather than illustrating all the nucleotides, includes source-tag S-1 and marker tag M-1. The microparticle 610 includes capture probe S-1' which is the complement of source tag S-1, and includes capture probe M-1' which is the complement of marker tag M-1. When microparticle 610 is added to well 350 (see FIG. 3), S-1 anneals to S-1', and M-1 anneals to M-1', so that amplicon 614 attaches to microparticle 610. The amplicon 614 bends into a "U" type of shape where the amplicon 614 may crowd out amplicons and/or primers that do not include both source tag S-1 and marker tag M-1. The amplicon 614 may include Visual Label-1 that can be used to identify the allele.

FIG. 6D illustrates another design for the microparticles in FIG. 6B. The amplicon 626 includes source tag S-1 and marker tag M-1. The microparticle 622 includes capture probe S-1' which is the complement of source tag S-1, and includes capture probe M-1' which is the complement of marker tag M-1. However, in FIG. 6D the 3' end of the capture probe M-1 is oriented distal from the surface of microparticle 622, which is opposite to orientation of capture probe M-1' in FIG. 6C. In FIG. 6D, the amplicon 626 bends into an "S" shape instead of the "U" shape of FIG. 6C as a result of how marker tag M-1 anneals to its complementary capture probe M-1', due to the switching of the orientation of capture probe M-1'. The amplicon 626 may include Visual Label-1 that can be used to identify the allele.

It may be appreciated that the capture probes S-1' and M-1' in the embodiments of FIGS. 6C and 6D must be positioned in sufficient proximity to each other on the microparticles such that both probes may anneal to the same target polynucleotide to create, upon hybridization to the polynucleotide, the loop structure shown in FIGS. 6C and 6D. The length of the polynucleotide to be captured by the particle is therefore considered in selecting density of the capture probes on the microparticle surface.

FIG. 6E illustrates another design for the microparticles in FIG. 6B. The amplicon 638 includes source tag S-1 and marker tag M-1. The microparticle 634 includes capture probe S-1' which is the complement of source tag S-1, and includes capture probe M-1' which is the complement of marker tag M-1. In this design, the nucleotide sequences forming the capture probes S-1 and M-1 reside on the same oligonucleotide. In FIG. 6E, the amplicon 626 bends into an "O" shape which is different than the "U" shape of FIG. 6C and the "S" shape of FIG. 6D, as a result of how marker tag M-1 anneals to capture probe M-1' and how source tag S-1 anneals to capture probe S-1'. The amplicon 638 may include Visual Label-1 that can be used to identify the allele.

In some embodiments, as discussed above, the Visual Label-1 may be omitted. In such cases, the marker tag M-1 may include a barcode that encodes for the presence of both the allele and the polymorphism site. In some embodiments, the length of the marker tag M-1 may encode for the presence of both the allele and the polymorphic site and then electrophoresis may be used to identify the marker tag M-1.

In some embodiments, a molecular beacon may comprise the complement of the marker tag on one end and the complement of the source tag on the other end.

FIG. 7 illustrates a table of twenty-four DNA polymorphisms that are relevant to red blood cell antigens. The International Society of Blood Transfusion (ISBT) currently recognizes 30 major blood group systems (including the ABO and Rh systems). Many of the blood group systems were named after the patients in whom the corresponding antibodies were initially encountered. The ISBT definition of a blood group system is where one or more antigens are controlled at a single gene locus or by two or more very closely linked homologous genes with little or no observable recombination between them. The column entitled Polymorphism, 720, contains the designations of the specific selected single nucleotide polymorphisms of interest, each of these having two alleles, as shown in Number of alleles, 730. The column entitled Antigens, 740, contains the names of the corresponding antigens, many of these occurring in antithetical pairs, as illustrated for M and N. The antigen 740 is produced from the variation of the nucleotide sequence. The antigens may be (associated with) proteins on the surface of red blood cell, as described above with reference to FIG. 1C.

Note that "Hemoglobin S" 750 is not a blood group, but rather the polymorphism associated with sickle cell disease. The invention may also be used for the identification of such mutations.

FIG. 8 illustrates the operation of an embodiment of method 200 illustrated in FIG. 2 of identifying alleles of a plurality of polymorphic sites (24 as listed in table 700) in a plurality of nucleic acid samples (32 are used in this example). The difference between the embodiment illustrated in FIG. 8 and the previous example illustrated in FIGS. 2-6 is that in FIG. 8 only one polymorphism is determined per pool.

The method 200 of FIG. 2 (as now applied to identification of alleles of a plurality of polymorphic sites) begins with step (a): for each of the alleles to be identified, determining a source tag sharing number "d" for the allele. All the polymorphisms are determined to have a source tag sharing number "d"=1. The application of the method of allele determination with source tag sharing numbers other than 1 is discussed in the next example.

The method 200 of FIG. 2 continues with step 220 (b) for each of the different determined source tag sharing numbers "d": (i) dividing the plurality of nucleic acid samples into nucleic acid sample subsets. With each subset containing approximately the source tag sharing number "d" of nucleic acid samples so that each nucleic acid sample of the plurality of nucleic acid samples is included in at least one subset. Here, as discussed above, for this example of the method 200 the source tag sharing number "d" is equal to 1 is used for all 24 polymorphic sites illustrated in table 700.

Step 220 (b) continues with (ii) for each of the nucleic acid sample subsets, placing a portion of each of the nucleic acid samples included in the nucleic acid sample subset into a pool. This thereby provides a plurality of pools for the source tag sharing number "d" with each pool comprising a pooled subset of nucleic acid samples.

The following is an example of the performance of step 220 (b) (i) and (ii). Plate 810 (or microtiter plate) is a general purpose laboratory consumable that often contains ninety-six (96) (8 rows by 12 columns) wells 810 and may be used to perform experiments with samples that comprise nucleic acid samples. Note that, for convenience, only thirty-two (32) of the ninety-six (96) wells are illustrated as plate 810. For step 220 (b) (I) there is one DNA sample per subset.

And, for step 220 (b) (ii) each of the thirty-two (32) DNA samples (or blood samples or nucleic acid samples derived from DNA-containing samples) is placed in one of the wells (pools according to the term used in the method) of columns 810.1, 810.2, 810.3, 810.4, . . . , 810.32 of plate 810.

The step 220 (b) continues with (iii) for each pool of the plurality of pools for the source tag sharing number "d", performing a reaction (in this example amplification) in the pool (in this example wells) to produce reaction products (in this example amplicons) comprising a source tag identifying said each pool (in this example source tags with barcodes). The reaction products are produced using as templates said pooled subset of nucleic acid samples in said each pool (in this example there is only one nucleic acid sample per well).

The following is an example of how step 220 (b) (iii) may be performed. Primers are added to each well. Each primer comprises a source tag for identifying the well into which it has been placed, 810.1, . . . , 810.32. The thirty-two source tags comprise barcodes.

The thirty-two DNA samples in the wells are amplified with the primers comprising source tags. In each well, 810.1, . . . , 810.32, an amplicon from the respective DNA sample is produced with a source tag identifying the well containing the DNA sample. This produces in the first well 830.1 $^{S-1}$amplicons, in the second well 830.2 $^{S-1}$amplicons, . . . , and in the thirty-second (32) well 830.32 a set of $^{S-32}$amplicons. The notation $^{S-1}$amplicons was discussed above as meaning an amplicon comprising s-1 which is a source tag.

The method 200 of FIG. 2 continues with step 230 (c) for each of the different determined source tag sharing numbers "d", pooling in at least one pooled pool at least some of the said produced reaction products from at least two pools of the plurality of pools for the source tag sharing number "d". This thereby provides a plurality of pooled pools comprising at least one pooled pool for each of the different determined source tag sharing numbers "d". In the present example "d"=1. So, the nucleic acid samples each have their own source tag which can be used to identify not only the pool from which they came but also the nucleic acid sample.

The following is an example of performing step 230 (c) of FIG. 2. Aliquots from all of the thirty-two (32) wells 810.1, . . . , 810.32 are placed into well 845 of new plate 820. Note that as illustrated, separate plates 810, 820 are used, but the same plate could be used. Aliquots are then taken from well 845 and placed into twenty-four (24) new wells, 840.1 through 840.24 so that each of wells 850.1 through 850.24 contains amplicons, $^{S-1}$amplicons, $^{S-32}$amplicons, that is amplicons from each of the thirty-two (32) DNA samples. Notice that only three columns, 850.1, 850.2, and 850.3, are needed to accommodate these 24 new pools (as 8×3=24), which is the number of polymorphic sites to be determined.

The method 200 of FIG. 2 continues with step 240 (d) for each of the alleles to be identified, performing a second reaction (in this example amplification) using said reaction products (in this example amplicons) comprising said source tag (in this example barcodes) to produce allele-specific second reaction products (in this example amplicons) comprising a marker tag (in this example a visual label indicating which allele is present at the polymorphic site) and a derived source tag, and wherein said marker tag uniquely identifies an allele at a polymorphic site, and wherein said second reaction is in said pooled pool for the source tag sharing number "d". The "d" corresponds to the source tag sharing number "d" determined for the allele in step (a)

In this example, the source tag sharing number "d" is 1 for all the alleles. The following is an example of step (d). The allele at only one polymorphic site is determined per well 850. Two types of allele specific primers, primer$^{VL1}$ and primer$^{VL2}$, are added to each well 840.

Two primers are particularly designed for each well 840.1, . . . , 840.24. The two primers are denoted "Primer$^{VL1}$" and "Primer$^{VL2}$". Primer$^{VL1}$ is designed to only amplify amplicons in the well 840 that have the first allele for the polymorphic site that is being test in the well. Primer$^{VL2}$ is designed to only amplify amplicons in the well 840 that have the second allele for the polymorphic site that is being determined in the well. For example, in well 850.21, the allele for polymorphism Colton 760 (see Table 7) is determined. Primer$^{VL1}$ (to be placed in well 850.21) is designed to hybridize to amplicons $^{S-1}$amplicon, . . . , $^{S-32}$amplicon, in well 850.21 that have the allele Co$^a$ (designated the first allele). Primer$^{VL2}$ (to be placed in well 850.21) is designed to hybridize to amplicons $^{S-1}$amplicon, . . . , $^{S-32}$amplicon, in well 850.21 that have the allele Co$^b$ (designated the second allele). The notation "VL1" and "VL2" indicates that the primers primer$^{VL1}$ and primer$^{VL2}$, comprise visual label-1 and visual label-2, respectively. In this example, visual label-1 is a fluorescent green, and visual label-2 is a fluorescent red.

For the 24 wells that are illustrated in FIG. 8, 24 different versions of the primer primer$^{VL1}$ are designed and 24 different versions of the primer primer$^{VL2}$ are designed.

Figure 8A:
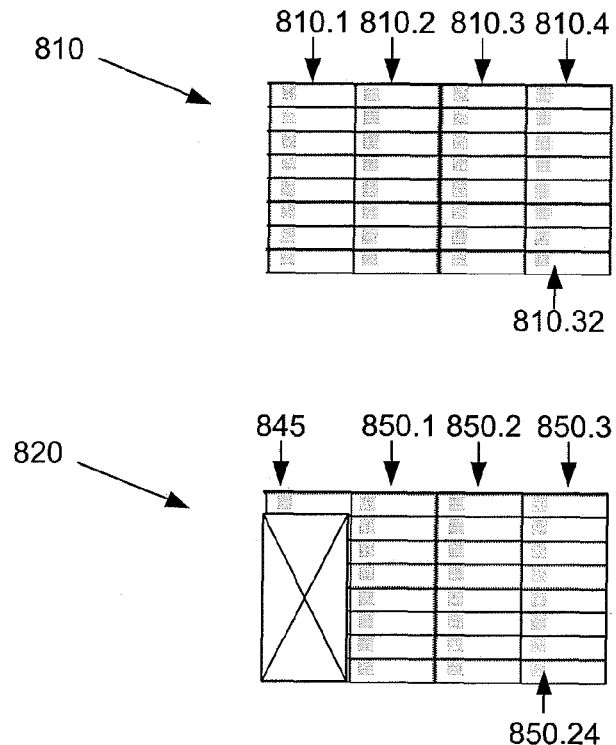
FIGS. 8A-8E schematically illustrate an embodiment of the method of FIG. 2 that determines the attribute profile for the twenty-four (24) polymorphisms listed in table 700 for thirty-two (32) blood samples, where in this example the alleles for only one polymorphism are determined at a time.
Figure 8B:
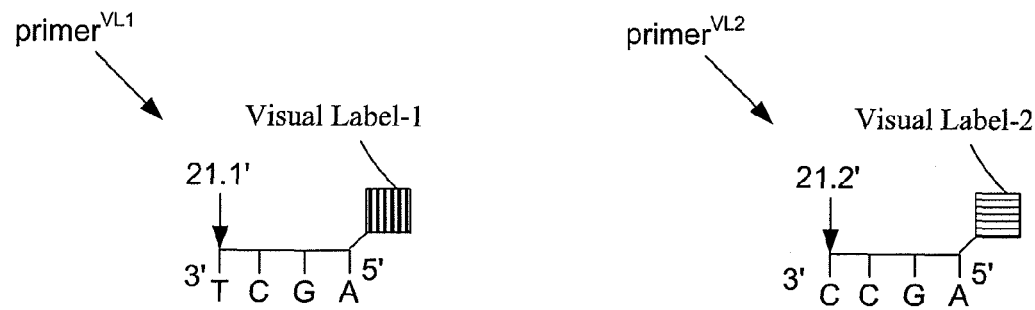

Primers primer$^{VL1}$ and primer$^{VL2}$ for well 850.21 (where allele for Colton is determined) are schematically illustrated in FIG. 8B. Element 21.1' is the complementary nucleotide that determines the allele Co$^a$ and 21.2' is the complementary nucleotide that determines Co$^b$.

The primers primer$^{VL1}$ and primer$^{VL2}$, which are particularly designed for each well, are added to the respective wells, 850.1, . . . , 850.24. PCR is performed on the amplicons in the wells 850.1, . . . , 850.24, with the different primers primer$^{VL}$ and primer$^{VL2}$ in each well. In each well, because of the design of primer$^{VL1}$, amplicons from primer$^{VL1}$ will be produced if an amplicon $^{S-1}$amplicon, . . . , $^{S-32}$amplicon, in the well comprises the first allele of the polymorphic site that is being interrogated in the well. The produced amplicon will be of the form, $^{S-N}$amplicons$^{VL-1}$, where N here indicates that amplicon $^{S-N}$amplicon comprises the first allele. And, because of the design of primer$^{VL2}$, amplicons from primer$^{VL2}$ amplicons, be produced if an amplicon, $^{S-1}$amplicons, . . . , $^{S-32}$amplicons, in the well comprises the second allele of the polymorphic site that is being interrogated in the well. The produced amplicons will be of the form, $^{S-N}$amplicons$^{VL-1}$, where N here indicates that amplicon $^{S-N}$amplicon comprises the second allele.

Figure 8C:
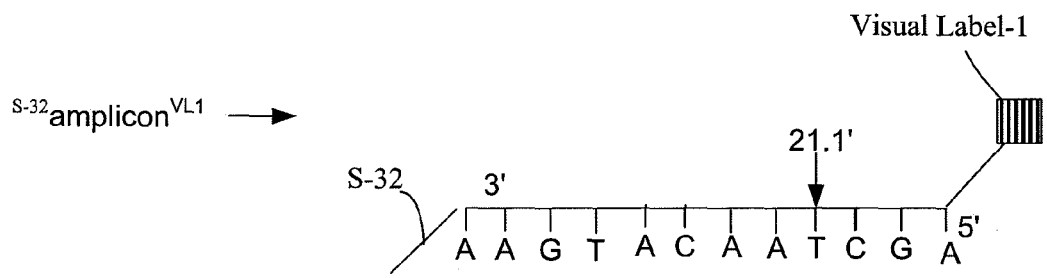

Illustrated in FIG. 8C is an example of a primer$^{VL1}$ that annealed to an $^{S-32}$amplicon and elongated during PCR in well 850.21. DNA sample thirty-two has the allele Co$^a$ for Colton 760 (see FIG. 7), since the amplicon $^{S-32}$amplicon$^{VL-1}$ was produced in well 850.21.

Alternative methods may have been used where the allele can be encoded by the length of the marker tag rather than using a visual label as the marker tag. Alternatively, beacons may be used to indicate the allele at the polymorphic site, where in some embodiments, the marker tag would encode the allele at the polymorphic site.

The method 200 of FIG. 2 continues with step 250 (*e*) identifying said allele-specific second reaction products by interrogating said derived source tag and said marker tag of said products, and if the interrogating of the derived source tag and the marker tag indicate unambiguous results, then identifying said alleles of the plurality of polymorphic sites, otherwise if the interrogating of the derived source tag and the marker tag indicate ambiguous results, then disambiguating the ambiguous results.

The following is an example of performing step 250 (*e*). Thirty-two microparticles are prepared comprising capture probes complementary to the thirty-two source tags on the amplicons $^{S-1}$amplicons, . . . , $^{S-32}$amplicons and with visual identifiers that can be decoded to determine the identity of the microparticle. The microparticle capture probe determines which of the DNA samples may anneal to the microparticle. In one embodiment, the visual code comprises six different fluorescent entities (such as "nanoparticles") to encode the identity of a microparticle (and the capture probe attached to it).

Figure 8D:
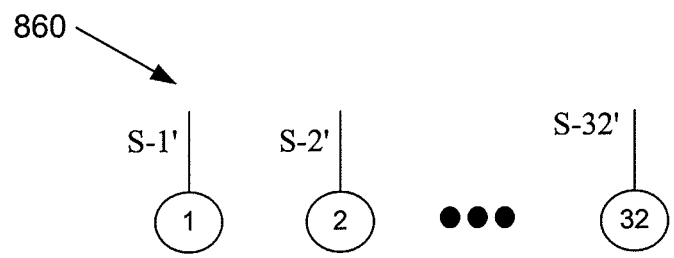

The microparticles 860 are numbered in FIG. 8D from 1 to 32, and are encoded with a binary tag arising from the six different fluorescent colors.

The thirty-two microparticles 860 are added to each of the wells 850.1 to 850.24. Thus, each of the wells 850.1 to 850.24 contain microparticles (860) 1 to 32.

Figure 8E:
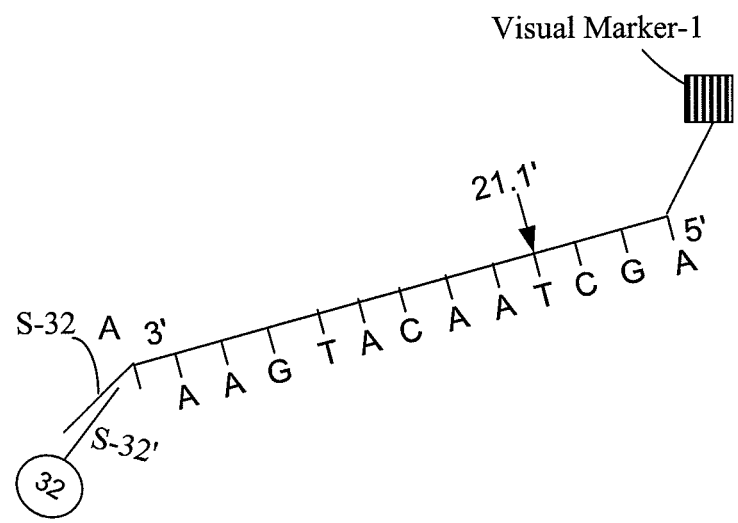

The wells 850.1 to 850.24 are then examined to determine the allele profile of each of the DNA samples. For example, as shown in FIG. 8E, in well 850.21, the amplicon $^{S-32}$amplicon$^{VL-1}$ was produced. The amplicon $^{S-32}$amplicon$^{VL-1}$ anneals to the capture probe of the microparticle 860 having the label 32, since the capture probe S-32' on the microparticle 860 labeled "32" is the complement of source tag S-32. The allele for polymorphism 21 (Colton) can then be determined by decoding the binary code on microparticle 860 labeled "32" and by noting that visual marker 1, which is green, is proximate to the microparticle 860 labeled "32" in well 850.21. If DNA sample 32 had been heterozygous for polymorphism 21, then well 850.21 would contain both $^{S-32}$amplicons$^{VL-1}$ and $^{S-32}$amplicons$^{VL-2}$, so that both red and green would be proximate to microparticles with label "32."

Similarly, the alleles for the other 23 polymorphic sites are determined for DNA sample 32. Similarly, the alleles for the other DNA samples, 1 to 31, are determined.

In some embodiments, an aliquot from each well, 850.1, . . . , and 850.24, may be placed in contact with a pre-assembled array or with a suspension of encoded microparticles 860.

In some embodiments, method 200 described above, starts with amplicons of genomic DNA. Prior to the first step of the method, genomic DNA is extracted from the biological sample, e.g. blood samples. Practical considerations limit the number of samples that can be pooled in step (c) of method 200. Signal detection of fluorescence sensitivity of current technology may place the practical limit near 32 samples in a single well for the embodiment described above.

The example above illustrates a number of advantages of embodiments of the invention over existing methods for allele determination. In some existing methods, an allele profile is determined for one sample at a time. In one such prior method, amplicons from one nucleic acid source sample without a source label are placed in a well with allele-specific primers which include polymorphic site codes for determining the alleles for two or more polymorphic sites. Amplification is then performed one or more times to determine the allele profile of the one sample. Applying this existing method may take five to six hours for a complete allele determination of the twenty-four polymorphic sites in Table 700 for ninety-six samples, which would be 2*24*96=4608 allele determinations. The method described with reference to FIG. 8 has the advantage of a higher rate of producing allele determinations than the existing method of analyzing a single sample. For example, a single ninety-six well plate 810 will accommodate four sets of twenty-four wells, and thus will produce 4*32=128 complete allele profiles for thirty-two samples per well in a conventional "multiplex" method. The "pool and split" step of the method of the invention adds only modest additional processing time. For example, as described, aliquots from each of the thirty-two samples are taken after source-tagging, and combined in a single container in three transfer steps of 10 seconds per step using a standard 8-channel pipette. Aliquots of the new pool are then placed into each of twenty-four new wells (one well per polymorphism), with a single pipette at a rate of five seconds per step, which is approximately (30+24*5) seconds, or 2½ minutes. However, time and expense is saved by the current method in the discriminating and identifying steps: for every three-hundred-and-eighty-four (384) samples (the equivalent of four (4) 96-well plates), the pool and split format saves the processing time (and reagents) for an entire plate, as three-hundred-and-eighty-four (384) samples will be accommodated in 384/128=3 plates. Additionally, the method described in FIG. 8 may require only one multiplex PCR reaction, namely to produce all source-tag coded amplicons for single samples, as in the current method, but the introduction of source-tagging enables omitting multiplex discrimination, as is used by the traditional method. Often, assay development time is increased by the requirement that multiple polymorphisms be determined in a single well, because of the heterogeneous configurations (and different optimal reaction conditions) associated with determining these multiple polymorphisms.

In some embodiments, the allele-specific primers may not comprise visual labels. The marker tag may encode both the polymorphic site and the allele present at the polymorphic site. For example, two different barcodes for the marker tag can be used, one identifying the "Normal", the other identifying the "Variant" allele. The combination of polymorphic site and allele code then may be detected by, for example, using microparticles comprising a source-tag capture probe and a polymorphic site and allele capture probe. In the example above, sixty-four (32*2) microparticles could be added to each well with two microparticles per nucleic acid sample, where each microparticle comprises a capture probe that is the complement of the source tag and a capture probe that is the complement of the marker tag that encodes both the polymorphic site code and allele code. Since there is a microparticle for each of the alleles, the alleles can be determined by identifying the microparticles (by way of their fluorescence code) with annealed amplicons, as produced in the previous example.

In embodiments, some wells may be used to determine more than one polymorphism. In this case, the allele-specific primers are designed with a marker tag that can be used to identify the polymorphic site for which the allele is being determined. This marker tag may be designed in a number of ways as the following three examples illustrate.

In a first embodiment, the visual labels comprise four different colors in the case of two polymorphisms of two alleles each being determined in a single well. Thirty-two microparticles per well can be added to determine the alleles.

In a second embodiment, a marker tag may be used with a visual label. To determine in each well the alleles at two bi-allelic polymorphic sites, two different marker tags would be used with two different visual labels each. The microparticles for this method would comprise a source tag and a marker tag. The allele of the polymorphic site would be determined by the visual label. And, the polymorphic site and the nucleic acid sample would be determined by the microparticle. Sixty-four microparticles can be added to each well to determine the alleles at two bi-allelic polymorphic sites for thirty-two nucleic acid samples.

In a third embodiment, four different marker tags can be used each, each marker tag indicating a polymorphism and an allele for the polymorphism. One-hundred-and-twenty-eight (128) microparticles would then be used to determine the alleles for the thirty-two DNA samples in each well.

In still other embodiments, the length of the source tag and/or marker tag may be used to identify the allele-specific reaction second products. Encoding schemes were discussed above and will be discussed in more detail below.

Figure 9:
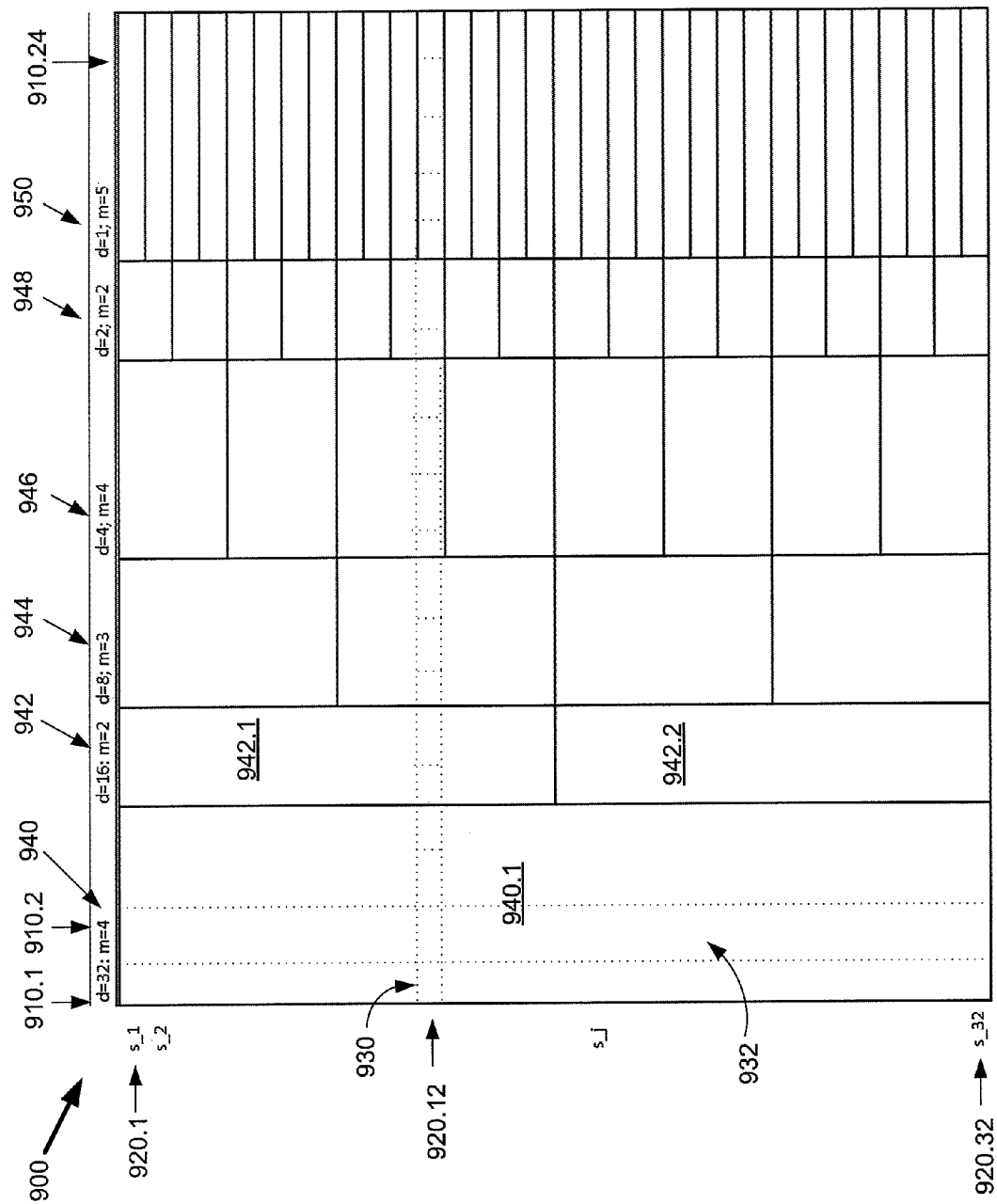
FIG. 9 schematically illustrates the difference between the traditional method of determining an allele profile for thirty-two (32) nucleic acid samples and embodiments of the invention.

FIG. 9 schematically illustrates the difference between some embodiments of the invention and a traditional method of determining an allele profile for thirty-two nucleic acid samples and twenty polymorphic sites. Polymorphic sites are listed along the columns in table 900, from column 910.1 to column 910.24. Nucleic acid samples are listed as "s_1" 920.1 to "s_32" 920.32 along the rows.

The traditional method determines the identity of the allele at a polymorphic site one nucleic acid sample at a time. For example, one nucleic acid sample s_12 (element 920.12) will be selected for analysis and then the identity of the allele at each of the twenty-four polymorphic sites may be determined for the one nucleic acid sample s_12 (element 920.12). The traditional method is schematically illustrated as row 920.12 with the dotted lines. The box 930 indicates that the identity of the allele at polymorphic site 910.1 is determined for only the nucleic acid sample 920.12.

In contrast, in some embodiments of the invention, the identity of the allele at a single polymorphic site (column 910) is determined for more than one nucleic acid sample 920 at the same time. For example, in the well 850.1 of FIG. 8A, the identity of the allele at a single polymorphic site is determined for all thirty-two nucleic acid samples in a single reaction. The box 932 formed by dotted lines indicates that the identity of the allele at polymorphic site 910.2 is determined for all 32 nucleic acid samples at the same time.

Returning to FIG. 9, the identity of the allele at more than one polymorphic site is determined for more than one nucleic acid sample in the same pool. For example, the bin 940.1, which is columns 910.1 through 910.4, with notation "d=32, m=4" indicates that "d"=32 nucleic acid samples s_1 to s_32 are pooled and the identify of alleles at "m"=4 polymorphic sites is determined for each of the 32 nucleic acid samples. Similarly, the bins 942.1 and 942.2, which include columns 910.5 and 910.6, with notation "d=16, m=2" indicates that 16 nucleic acid samples will share a source tag, so the nucleic acid samples are split into two groups: nucleic acid samples s_1 to s_16, which share a source tag, and nucleic acid samples s_17 to s_32, which share a source tag. The nucleic acid samples included in bin 942.1 may be one pool and the nucleic acids included in bin 942.2 may be a second pool. The (reaction products formed in) two pools of the bins 942.1 and 942.2 may then be pooled and the identify of 2 alleles at 2 polymorphic sites may then be determined for all 32 nucleic acid samples.

The example illustrated with FIG. 8 only dealt with the source tag sharing number "d"=1. The value of "d" will determine the number of nucleic acid samples that share a source tag. Source tag sharing numbers "d">1 can be advantageous when the frequency of an allele is low. For example, the Colton 760 blood group system illustrated in table 700 of FIG. 7 has a polymorphic site with two alleles: one of the alleles occurs with over 99% probability (probabilities not illustrated in table 700) and the other allele occurs with less than 1% probability (in Caucasians). By using the same source tag for more than one nucleic acid sample, the number of operations in determining allele profiles for a given number of nucleic acid samples may be reduced (compared with the conventional "one-sample-at-a-time" method). However, if all of the alleles are not the same for a polymorphic site, then the methods disclosed above may not unambiguously identify the alleles in step (e) of the method 200 without additional disambiguation as described below.

Figure 10:
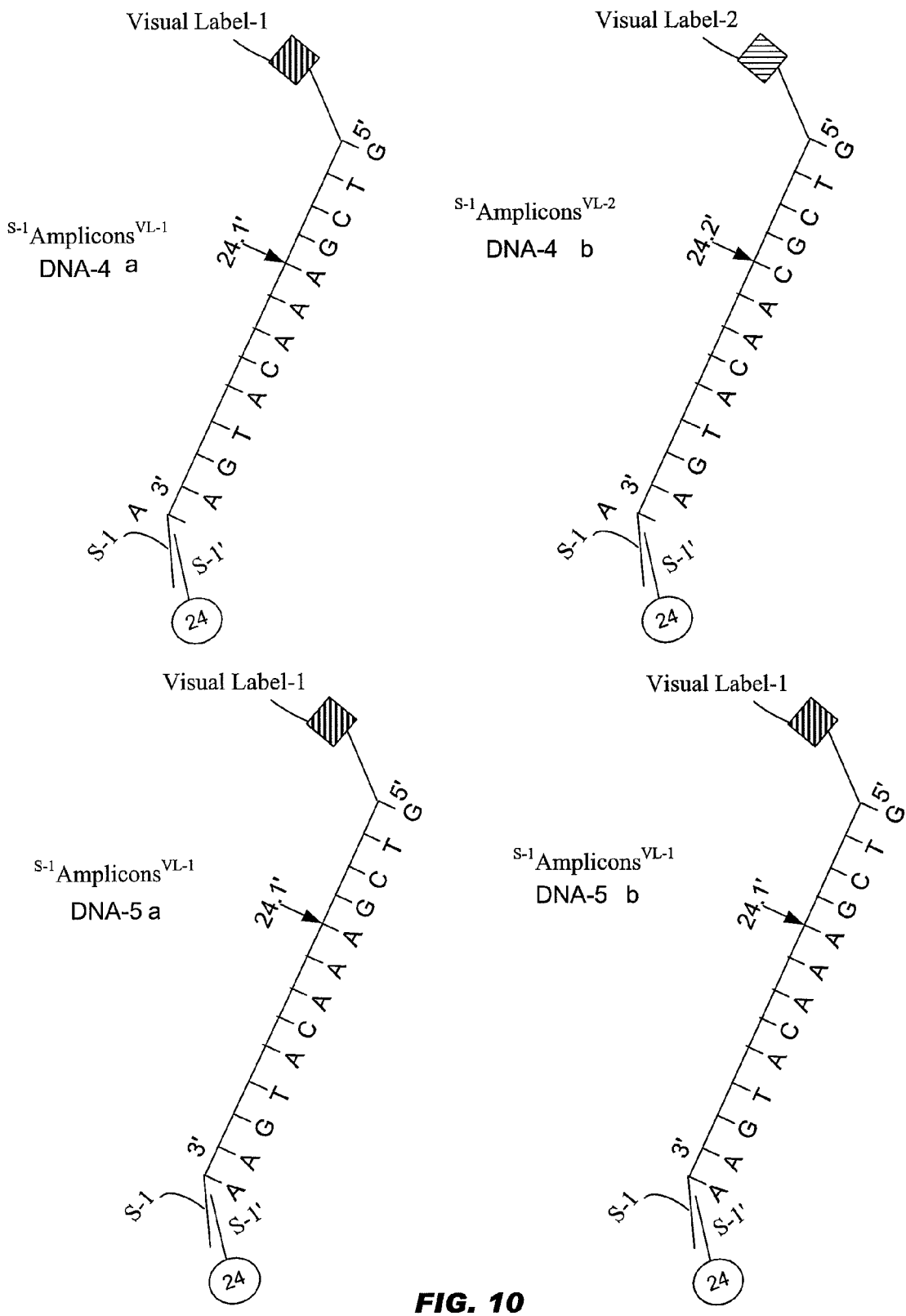
FIG. 10 schematically illustrates how an ambiguity may arise from sharing source tags in the event of heterozygosity illustrated here by DNA-4a (SEQ ID No. 8) vs DNA-4b (SEQ ID NO. 9), wherein DNA-4a contains the sequence of an allele present in one chromosome and DNA-4b contains the sequence of the allele present in the other chromosome of the chromosome pair; DNA-5a and DNA-5b (SEQ ID NO. 8)

FIG. 10 illustrates how an ambiguity may arise when nucleic acid samples share source tags. Illustrated in FIG. 10 are $^{S\text{-}1}$amplicons$^{VL\text{-}1}$ and $^{S\text{-}1}$amplicons$^{VL\text{-}2}$ which are produced from DNA-4 and DNA-5. Here, "a" and "b" refer to alleles present on the two chromosomes of a chromosome pair. It is assumed for the sake of illustration that the amplicons are produced as follows. As shown in FIG. 10, DNA-4 is heterozygous at polymorphism site 24. Thus, for instance, DNA-4a comprising the allele sequence from one chromosome has an "A" at polymorphic site 24, designated by "24.1," and DNA-4b comprising the allele from the other chromosome of the chromosome pair has a "C" at polymorphic site 24, designated by "24.2." DNA-5 is homozygous at site 24. DNA-4 and DNA-5 may have been pooled, and primers the source-tag S-1 added to the pool. Assume for the sake of illustration that PCR was performed to produce amplicons from DNA-4 and DNA-5 having the source-tag S-1, and that allele specific primers for polymorphic site 24 were added to the produced amplicons to produce $^{S\text{-}1}$amplicons$^{VL\text{-}1}$ and $^{S\text{-}1}$amplicons$^{VL\text{-}2}$.

The amplicons, $^{S\text{-}1}$amplicons$^{VL\text{-}1}$ and $^{S\text{-}1}$amplicons$^{VL\text{-}2}$, were produced from the heterozygous DNA-4, reflecting the presence of both alleles, 24.1 and 24.2, respectively labeled a and b. (Only one strand is shown here for each double stranded allele.) In contrast, only $^{S\text{-}1}$amplicons$^{VL\text{-}1}$ produced from the homozygous DNA-5, reflect the presence of only one allele, 24.1, at polymorphic site 24.

As shown in FIG. 10, the signal that is recorded from a microparticle 24 having a capture probe that anneals to source tag S-1 would indicate the presence of both visual label VL-1 and visual label VL-2 in the amplicons from DNA-4. If source tag S-1 was contained only in amplicons produced from DNA-4, then the presence of both visual label VL-1 and visual label VL-2 would unambiguously signal that DNA-4 is heterozygous. But since both DNA-4 and DNA-5 share source tag S-1, the result of probing their amplicons with microparticle 24 is ambiguous because there are other possible combinations that would give the same result of both a visual marker 1 and visual marker 2. For example, DNA-4 could be homozygous for 24.1 (that is, have allele 1 only) and DNA-5 could be homozygous for 24.2 (that is, have allele 2, only); alternatively, DNA-4 could be homozygous for 24.2, and DNA-5 heterozygous; and so on.

Figure 11:
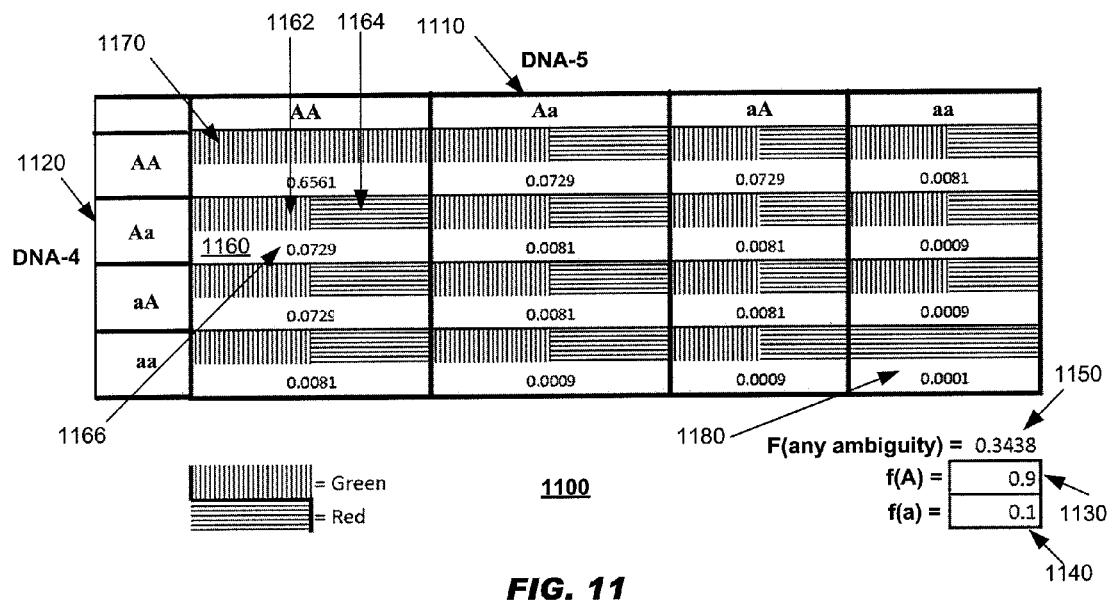
FIG. 11 schematically illustrates the probabilities for an ambiguity when a source tag is shared between amplicons of two DNA samples.

FIG. 11 illustrates the probabilities for an ambiguity when a source tag is shared between amplicons of two different DNA samples. Along one axis are bi-allelic configurations for DNA-4 and along the other axis are bi-allelic configurations for DNA-5. For purposes of illustration, only a single polymorphic site is considered. The notation "Aa" (1120) means that DNA-4 is heterozygous, having both allele "A" and allele "a" (indicating that, say, allele "A" was inherited from the mother, and "a" from the father, "aA" denoting the other possibility); similarly, notation "Aa" (1110) means that DNA-5 is heterozygous; while notation "AA" indicates homozygosity for allele "A" and notation "aa" indicates homozygosity for allele "a". FIG. 10 illustrates the situation where DNA-4 is heterozygous, with configuration "Aa" (or "aA") and DNA-5 is homozygous, with configuration "AA". The notation "f(A)=0.9" (1130) in FIG. 11 means that the probability or frequency of the "A" allele is set to 90 percent. The notation "f(a)=0.1" (1140) means that the probability or frequency of allele "a" is set to 10 percent. The entry (1160) represents the state of the visual labels (1162 and 1164) and the value of the probability (1166) that DNA-4 and DNA-5 have the indicated allele configuration, "Aa" for DNA-4 and "AA" for DNA-5. In entry (1160) one visual marker is green (1162) and the other visual marker is red (1164). The probability of this configuration is 0.0729 (1166). The only entries in the table of FIG. 11 that do not have both a red visual marker and a green visual marker are entries (1170) and (1180). Entry (1170) corresponds to the allele configuration "AA" for both DNA-4 and DNA-5. Both visual markers are therefore green. The probability of this configuration is 0.6561 or almost ⅔ of the time, corresponding to the presence of four copies of the "A" allele (observed with probability 0.9). Hence the probability of an ambiguity is 0.9*0.9*0.9*0.9=0.6561. The other entry in Table 11 where there is no ambiguity is entry (1180), where both visual markers are red, corresponding to allele configuration "aa" for both DNA-4 and DNA-5. The probability of this configuration is only 0.0001, corresponding to the presence of four copies of the "a" allele (observed with probability 0.1). Hence the probability of no ambiguity for this allele configuration is 0.1*0.1*0.1*0.1=0.0001.

Often the allele that has the highest probability of occurring at a polymorphic site is referred to as the normal (N) allele and the allele that has the lower probability of occurring is referred to as the variant (V) allele. The variant allele also may be referred to as "mutant" and the normal allele as "wild-type", especially for alleles known to be associated with disease.

For two nucleic acid samples sharing a source tag, the probability of an ambiguity occurring is given by $$\text{Probability(ambiguity)}=1-f(N)^4-f(V)^4. \quad \text{Equation 1}$$

In the example of FIG. 11, Prob(ambiguity)=1−(0.9)⁴−(0.1)⁴=1−0.6561−0.0001=0.3438 (the value at 1150). Similarly, the binominal theorem can be used to determine the probability of an ambiguity, for four nucleic acid samples sharing the same source tag. Let "d" be equal to the number of nucleic acid samples sharing the same source tag. In this case, d=4. For a bi-allelic marker: Prob(ambiguity)=1−f(n)$^{d*2}$−f(v)$^{d*2}$, or 1−f(N)⁸−f(V)⁸. The greater the number, "d", of nucleic acid samples sharing the same source tag, the greater the chance of an ambiguity. The less frequent the variant allele, the lower the probability of an ambiguity for a given value of source tag sharing number "d". In general, the probability of an ambiguity for a polymorphic site with m alleles is given by:

$$\text{Probability(ambiguity)}=1-f(N)^{m*d}-f(V)^{m*d}. \quad \text{Equation 2}$$

Where as above, f(N) is the frequency of a normal allele, f(V) is the frequency of a variant allele, and d is the number of samples sharing the same source tag.

Equation 2 can be used to determine a source tag sharing number, d, to use to determine an allele at a polymorphic site. If the "Probability (ambiguity)" is set to a particular value, then all the terms in equation 2 are known except the value of "d" which can be solved for.

The "Probability (ambiguity)" may be set to the highest acceptable probability of an ambiguity occurring in a set of "d" nucleic acid samples sharing the same source tag, and may be denoted "C". Given a value of "C", a value of "d" may be determined from Equation 2.

"C" may be determined prior to determining the source tag sharing numbers, or source tag sharing numbers may be determined for different values of "C" to determine a set of source tag sharing numbers that will produce more efficient allele determination. Some alleles may be determined in the same pools as other alleles. In this case, the alleles may be said to be binned in that the alleles will be determined with the same source tag sharing number. In some embodiments, alleles may be binned and different source tag sharing numbers may be used to determine the different alleles.

The value of "d" may be set to the largest integer of the form 2^n (some of the more common numbers used for this method of 2^n are n=1, 2^1=2; n=2, 2^2=4; n=3, 2^3=8; n=4, 2^4=16; n=5, 2^5=32; n=6, 2^6=64; and, n=7, 2^7=128) so that the value of Equation 2, "Probability (ambiguity)" is less than "C." The value of "d" may also be limited by a preset maximum pool size (e.g. 32), which may be related to technical reasons that limit the pool size.

In the method 200, the value "C" represents the probability that the allele determination for a plurality of nucleic acid samples is ambiguous—because at least one constituent sample has both alleles—and thus that additional steps are needed to resolve the ambiguity. The source tag sharing number, "d", of method 200 may be determined from equation 2 for the largest "d" so that Probability (ambiguity) is less than C. So, the following equation can be used to determine the maximum number of "d" given C and the frequency of the variant allele, f(V):

$$d=0.5*\log(1-C)/\log(1-f(V));\qquad \text{Equation 3}$$

preferably, as in FIGS. 12A and 12B, "d" is set to the largest integer of the form 2^n that is less than or equal to the value "d" produced by equation (3) for a preset "C".

Figure 13:
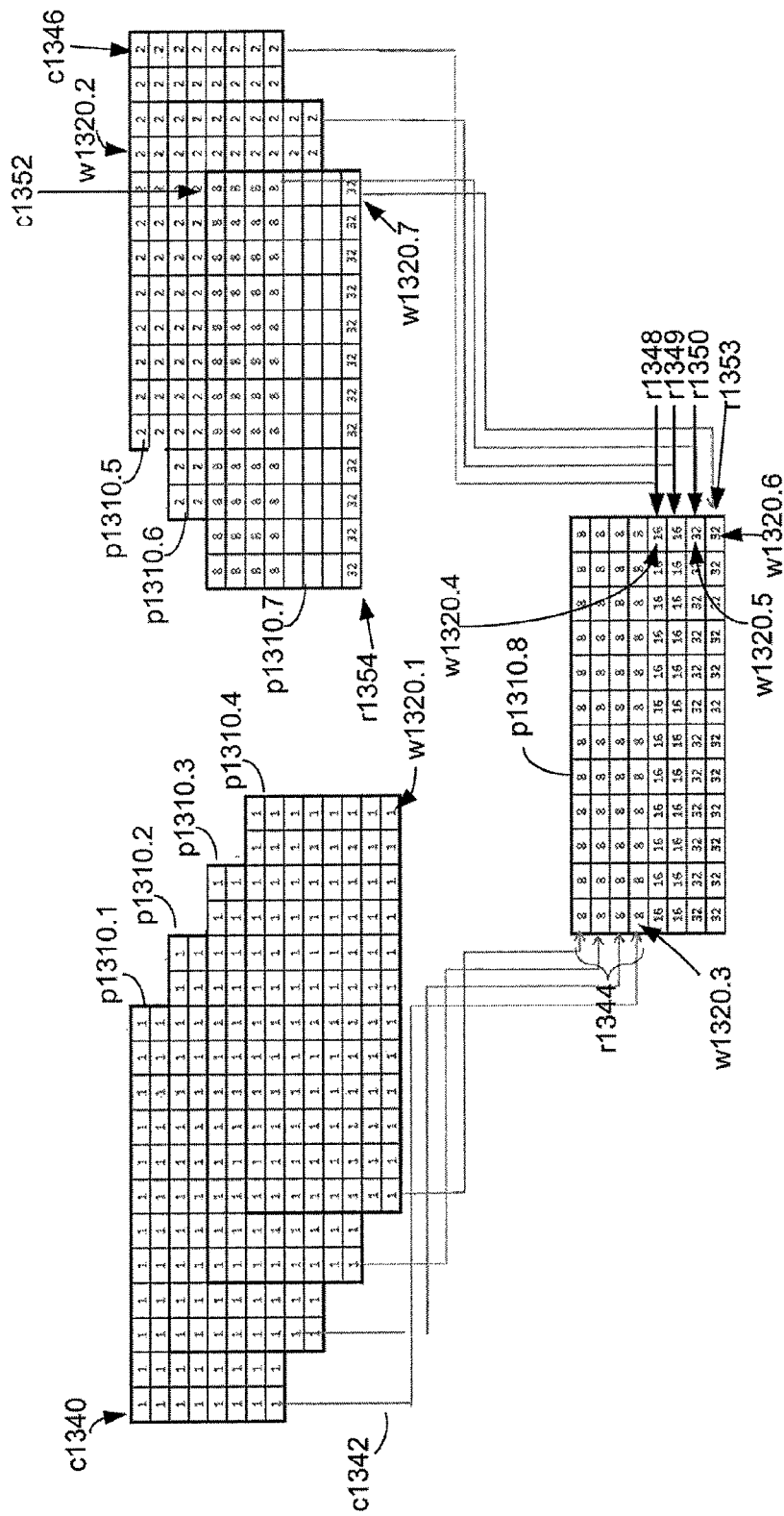
FIG. 13 schematically illustrates an example of determining the attribute profile of three-hundred-and-eighty-four 384 (4 times 96) blood samples for the sixteen polymorphic sites illustrated in FIG. 12A with the "d" values illustrated for the African American population in FIG. 12A.

FIGS. 12 and 13 illustrate another example of the method 200 of identifying alleles of a plurality of polymorphisms in a plurality of nucleic acid samples. In this example source tag sharing numbers "d" are determined for more than just the case where "d"=1 as in the previous examples of the method 200.

FIGS. 12A and 12B illustrate an example of step (a) of method 200 of that is for each of the alleles to be identified, determining a source tag sharing number "d" for the allele.

FIG. 12A is an illustration of an allele frequency for African Americans and FIG. 12B is an allele frequency for Caucasians.

Table 1210 illustrates an arrangement of blood group system alleles 1250 and their frequencies observed in African Americans. The features of table 1210 include ISBT designation (element 1252); polymorphic site name (element 1254); the frequency of allele A (element 1256); and, the frequency of allele B (element 1258). The frequencies of the alleles are sometimes approximated with a "1" or "0". Two values are set prior to determining the source tag sharing number "d". These values are "C" (element 1270), which, as discussed above, is the highest acceptable probability of an ambiguity occurring in a plurality of d nucleic samples. Additionally, the maximum pool size, "Max PoolSz" (element 1272) is set prior to determining the source tag sharing numbers "d". The "Max PoolSz" (element 1272) may be determined by limitations arising from the steps of the method. For example, in some embodiments, two microparticles with different tags are added to a pool to identify alleles of a single nucleic acid sample. Thus, the number of nucleic acid samples that are pooled together is limited by the number of different microparticle tags that can be manufactured.

The minimum frequency of the allele with the lowest frequency is represented as "f" (element 1260). A "d(S)" (element 1262) is calculated using Equation 3 with C=0.1800 (element 1270) (which is 18%). The logarithm to the base 2 (element 1264) is calculated for each of the "d(S)" values (element 1262) and rounded down to the nearest whole integer. The number "2" is then raised to the logarithm to the base 2 (element 1264) which yields the number of samples "d" to use for the source tag sharing number of method 200 (element 1266) where "d" is of the form 2^n for n an integer such that equation 2 "Probability (ambiguity)" is less than C (18%) 1270. The value in column (element 1266) is reduced to the max pool size (element 1272) which is 32 in the present example. For example, the calculated "N" (element 1262) for allele "CO" (element 1254) is 99.1758, and the closest power of 2 less than 99.1758 is 64. But since 64 is greater the "Max PoolSz" (element 1272), the "Max PoolSz", which is 32 is used for the source tag sharing number "d" of method 200.

Table 1220 illustrates the alleles from table 1210 binned into the source tag sharing "d" number, which is the number of source samples that may share the same source tag. For example, "SC" (element 1254) is placed into a bin with a source tag sharing number "d"=32 because its value for "d", shown, in column (element 1266) is 32. The number of bins illustrated in table 1220 is 6, for "d" of 1, 2, 4, 8, 16, and 32, which is all the bins that are possible for powers of 2 that do not exceed 32. The total number of alleles (element 1276) is listed for each of the bins. Alleles that have the same source tag sharing number "d" may be identified in the same pool. Alleles that are identified in the same pool may said to be binned together.

Similarly, tables 1230 and 1240 illustrate the source tag sharing numbers "d" and allele binning for Caucasians. Note the difference in the frequencies at the polymorphic sites (1350) between the two groups. For example, the variant form of allele SC (1254) has a frequency of 0.006 in Caucasians and only 0.002 in African Americans, which results in SC being in the 32 bin for African Americans, but in the 16 bin for Caucasians.

The method 200 of FIG. 2 continues with step 220 (b) for each of the different determined source tag sharing numbers "d": (i) dividing the plurality of nucleic acid samples into nucleic acid sample subsets, each subset containing approximately the source tag sharing number "d" of nucleic acid samples so that each nucleic acid sample of the plurality of nucleic acid samples is included in at least one subset. (ii) for each of the nucleic acid sample subsets, placing a portion of each of the nucleic acid samples included in the nucleic acid sample subset into a pool, thereby providing a plurality of pools for the source tag sharing number "d", wherein each pool comprises a pooled subset of nucleic acid samples; and (iii) for each pool of the plurality of pools for the source tag sharing number "d", performing a reaction in the pool to produce reaction products comprising a source tag identifying said each pool, wherein said reaction products are produced using as templates said pooled subset of nucleic acid samples in said each pool.

In alternative embodiments step (b) (iii) comprises: (iii) if "d" is less than a maximum_pool_size, for each pool of the plurality of pools for the source tag sharing number "d", performing a reaction in the pool to produce reaction products comprising a source tag identifying said each pool, wherein said reaction products are produced using as templates said pooled subset of nucleic acid samples in said each pool. Note that "maximum_pool_size" may be referred to as "max poolsz".

FIG. 13 illustrates an example of determining the attribute profile of 384 blood samples for the 16 polymorphic sites illustrated in FIG. 12A with the "d" values illustrated in Table 1220 of FIG. 12A. Elements in FIG. 13 are identified with a "p" when the element illustrates a plate, an "r" when the element illustrates a row of plate, a "c" when the element illustrates a column of a plate, and a "w" when the element illustrates a well of a plate.

gDNA is extracted from each of the 384 blood samples to produce 384 gDNA samples.

Plates p1310 are illustrated with 8×12 or 96 wells (element w1320) per plate p1310. Plates p1310.1, p1310.2, p1310.3, p1310.4, p1310.5, p1310.6, and p1310.7 illustrate amplifying "d" DNA samples with source-tags identifying the well 1320.

Four different values of "d", 1, 2, 8, and 16, are determined for the sixteen polymorphic sites of FIG. 12A for African Americans as illustrated in table 1220.

For source tag sharing number "d"=1, for each of the 384 gDNA samples, a pipette is used to place an aliquot of the gDNA sample in one of the wells of each of the plates p1310.1, p1310.2, p1310.3, and p1310.4. After performing this procedure, there will be one gDNA sample per well w1320.1 in each of the plates p1310.1, p1310.2, p1310.3, and p1310.4. Primers comprising unique source-tags are added to each of the wells of the plates p1310.1, p1310.2, p1310.3, and p1310.4. Amplicons are produced with the source tags. The source tags can be used to identify the well (but since in this example there is only one sample per well, the source-tag unambiguously identifies the sample). As shown in FIG. 13, there are four plates p1310.1, p1310.4 with 96 wells w1320.1 per plate p1310. Thus, each of the 384 samples is amplified in a well w1320.1 with a unique source-tag. Codes for the source tags are generated as discussed above. Thus, for the method 200 of FIG. 2 steps (b) (i), (ii), and (iii) is performed for "d"=1.

For source tag sharing number "d"=2, for each of the 384 gDNA samples, a pipette is used to place aliquots of gDNA samples in one of the wells of plates p1310.5 and p1310.6 so that each of these wells w1320.2 receives two DNA samples. Primers with source-tags to identify the well are added to each of the 2×96=192 wells of the 2 plates p1310.5 and p1310.6. A total of 2×192=384 amplicons will be produced with source-tags that can be used to identify the well. Codes for the source tags are generated as discussed above. Thus, for the method 200 of FIG. 2 steps (b) (i), (ii), and (iii) is performed for "d"=2.

For the source tag sharing number "d"=8, for each of the 384 gDNA samples, a pipette is used to place aliquots of gDNA samples in one of the wells in 4 rows of plate p1310.7 so that each well of the 4 rows of plate p1310.7 receives eight samples. Primers comprising source tags to identify the well (the source tags are unique compared to other source tags that are pooled together in the same pool so that the source tag can be used to identify the wells of p1310.7) are added to each of the 4×12=48 wells of the 4 rows of plate p1310.7. A total of 8×48=384 amplicons is produced with source tags that can be used to identify the well. The codes for the source tags are generated as discussed above. Thus, for the method 200 of FIG. 2 steps (b) (i), (ii), and (iii) is performed for "d"=8.

For source tag sharing number "d"=32, for each of the 384 gDNA samples, a pipette is used to place aliquots of gDNA samples in the one of the wells in one row of plate p1310.7 so that each well of the one row of plate p1310.7 receives 32 samples. Primers comprising unique source-tags are added to each of the 8 wells of the one row r1354 of plate p1310.7, and each of the 384 samples is amplified in a well with 31 (thirty-one) other samples. A total of (32*8) amplicons will be produced with source-tags that can be used to identify the pool. There is one row r1354 with 12 wells (12×32=384) and amplicons comprising a source-tag that can be used in a later step to identify the well. The codes for the source tags are generated as discussed above. Thus, for the method 200 of FIG. 2 steps (b) (i), (ii), and (iii) is performed for "d"=32.

In alternative embodiments, since "d"=32 and the maximum_pool_size is "32", no reaction is performed in the wells so that no primers with source tags are added. In alternative embodiments, since "d" is the same as the maximum_pool_size the source tags are not needed to identify the gDNA samples.

Thus, in plates p1310.1 through p1310.7 of FIG. 13, pools are formed by combining one or more gDNA samples in wells, in accordance with each of the "d" values for each of the 384 samples, for determining the allele profile comprising 16 polymorphisms of FIG. 12A, table 1210.

The method 200 of FIG. 2 continues with (c) for each of the different determined source tag sharing numbers "d", pooling in at least one pooled pool at least some of the said produced reaction products from at least two pools of the plurality of pools for the source tag sharing number "d". Thereby a plurality of pooled pools comprising at least one pooled pool for each of the different determined source tag sharing numbers "d" is provided.

In alternative embodiments step (c) comprises: (c) for each of the different determined source tag sharing numbers "d", if "d" is less than a maximum_pool_size, pooling in at least one pooled pool at least some of the said produced reaction products from at least two pools of the plurality of pools for the source tag sharing number "d", thereby providing a plurality of pooled pools comprising at least one pooled pool for each of the different determined source tag sharing numbers "d", otherwise if "d" is equal to or greater than the maximum_pool_size then said each pool is the at least one pooled pool.

For source tag sharing number "d"=1, eight wells are pooled. The eight wells of column (element c1340) of plate p1310.1 are pooled in well w1320.3 of plate p1310.8. Therefore, in well w1320.3 there are eight samples each comprising its own source-tag for identification. The seven polymorphic sites of table 1220 (see FIG. 12A, for polymorphic sites "FY, GYPBS, DO-793, GYPA, JK, HbS173") with a "d" value of 1 are determined in well w1320.3, as discussed below. The alleles of the seven polymorphic sites listed above may be said to be "binned" together. Similarly, the wells of each of the columns c1342 of plates p1310.1, p1310.2, p1310.3, p1310.4 are pooled in one of the wells of plate 1310.8, so that the wells of the top four rows r1344 of plate 1310.8 are used for the pooled pools. The rows used for pooling the wells of the columns c1340 of plates p1310.1, p1310.2, p1310.3, and p1310.4 are labeled "8" in plate p1310.8. Note that the maximum pool size for this example was set to 32 nucleic acid samples, so that wells of up to four columns in FIG. 13 could be pooled, yielding a total of thirty-two samples. But a lower number of nucleic acid samples are pooled because multiple polymorphic sites are determined in each pool. Thus, for the method 200 of FIG. 2 step (c) is performed for "d"=1.

For source tag sharing number "d"=2, the contents of the wells of each column c1346 of plates p1310.5 and p1310.6 in FIG. 13 are pooled in a well of plate p1310.8. For example, each of the contents of the wells of column c1346 in FIG. 13 is pooled in well w1320.4, for a total of 2*8=16 samples in well w1320.4. The source-tags in w1320.4 are shared by two samples so that there are eight different source-tags in well w1320.4. Alleles associated with the three polymorphic sites that are binned together ("LU, DO-323, and DO-350") are determined in well w1320.4, in accordance with the design in table 1220 The remaining wells of the columns of plates p1310.5 and p1310.6 are similarly pooled to form the pooled pools in the two rows r1348, r1349 of plate p1310.8. Each of the wells is labeled "16" in plate p1310.8. Thus, for the method 200 of FIG. 2 step (c) is performed for "d"=2.

For source tag sharing number "d"=8, the top four wells of each column c1352 of plate p1310.7 are pooled in a well w1320.5 in row r1350 of plate p1310.8. For example, the top four wells in column c1352 are pooled in well w1320.5 for a total of 4*8=32 samples in well w1320.5, where the source-tags are shared by 8 (eight) samples so that, in well w1320.5 of plate p1310.8, there are 4 different source-tags. Alleles associated with the two polymorphic sites binned together ("K(1/2), FY265") will be determined in well w1320.5, in accordance with the design in table 1220. The top four wells of each of the remaining columns of plate p1310.7 are similarly pooled to form the pooled pools of row r1350 of plate p1310.8 each labeled with "32". Thus, for the method 200 of FIG. 2 step (c) is performed for "d"=8.

For "d"=32, the wells of the last row r1354 of plate p1310.7 are moved into a well of the last row r1353 of plate p1310.8. For example, the well w1320.7 is moved into well 1320.6. Each of the wells w1320.6 may have only one source tag code, or in view of the chosen practical limit of pooling a maximum of only 32 samples, each of the wells 1320.6 may not have a source tag as discussed above for alternative embodiments. Alleles associated with the four polymorphic sites binned together ("SC, DI(B/A), CO, and LW") are determined in well 1320.6 and the other wells of row r1353 of plate 1310.8, in accordance with the design 1220. Thus, for the method 200 of FIG. 2 step (c) is performed for "d"=32.

In embodiments, the blood samples are pooled and then gDNA is extracted from the pooled blood samples. In embodiments, the gDNA may be a different kind of nucleic acid sample.

The method 200 of FIG. 2 continues with (d) for each of the alleles to be identified, performing a second reaction using said reaction products comprising said source tag to produce allele-specific second reaction products comprising a marker tag and a derived source tag, wherein said derived source tag is at least one of: said source tag, a copy of said source tag, or a copy of the complement of the source tag, and wherein said marker tag uniquely identifies an allele at a polymorphic site, and wherein said second reaction is in said pooled pool for the source tag sharing number "d", the "d" corresponding to the source tag sharing number "d" determined for the allele in step (a).

In some alternative embodiments step (d) comprises: (d) for each of the alleles to be identified, if "d" is less than a maximum_pool_size, performing a second reaction using said reaction products comprising said source tag to produce allele-specific second reaction products comprising a marker tag and a derived source tag, wherein said derived source tag is at least one of: said source tag, a copy of said source tag, or a copy of the complement of the source tag, and wherein said marker tag identifies an allele at a polymorphic site, and wherein said second reaction is in a pooled pool of said at least one pooled pool for the source tag sharing number "d", the "d" corresponding to the source tag sharing number "d" determined for the allele in step (a), otherwise if "d" is equal to or greater than a maximum_pool_size then performing a second reaction using said pooled subset of nucleic acid samples to produce allele-specific second reaction products comprising a marker tag, wherein said marker tag uniquely identifies an allele at a polymorphic site, and wherein said second reaction is in the pooled pool for "d", the "d" corresponding to the source tag sharing number "d" determined for the allele in step (a).

For the source tag sharing number "d"=1, added to the wells in rows r1344 of plate 1310.8 are allele-specific primers directed to the polymorphic sites FY, GYPBS, DO-793, GYPA, JK, HbS173, comprising visual markers to indicate alleles for each of these polymorphisms (see table 1220 of FIG. 12A). The samples in wells in the four rows r1344 are amplified so that if a DNA sample has an attribute or allele, then an amplicon is produced comprising the marker tag and the source tag identifying the well from which the DNA sample originated. For example, if the sample in the first row of column c1340 of plate 1310.1 had allele FYA, that is allele "A" of polymorphism FY, then an amplicon would be produced in well w1320.3 comprising a marker tag indicating FYA, and a source-tag indicating the DNA sample originated from the well in the first row of the first column of plate p1310.1. Thus, for the method 200 of FIG. 2 step (d) is performed for "d"=1.

For the source tag sharing number "d"=2, added to the wells in rows r1348 of plate p1310.8, are allele-specific primers directed to the polymorphic sites LU, DO-323, and DO-350, with visual labels to indicate alleles for each of these polymorphic sites (see table 1220 of FIG. 12A). The samples in wells in the two rows r1448 are amplified so that if a DNA sample comprises an allele, then an amplicon is produced comprising the marker tag and the source tag identifying the well from which the DNA sample originated. For example, if one of the samples in the first row of column r1346 of p1410.5 contained allele "LUA", that is allele "A" of polymorphism LU, then an amplicon would be produced in well w1320.4 comprising a marker tag indicating the presence of LUA and a source tag indicating that the DNA sample originated from the well in the first row of column c1346 of plate p1310.5. Thus, for the method 200 of FIG. 2 step (d) is performed for "d"=2.

For the source tag sharing number "d"=8, added to the wells in rows r1350 of plate p1310.8, are allele-specific primers directed to the polymorphic sites K(1/2) and FY265, with visual markers to indicate alleles for each of these polymorphic sites (see table 1220 of FIG. 12A). The samples in wells in the one row r1350 are amplified so that if a DNA sample comprises an allele, then an amplicon is produced with the marker tag and the source tag identifying the well from which the DNA sample originated. For example, if one of the samples in the first column of c1352 contained allele FY265A, that is allele "A" of polymorphic site FY265, then an amplicon would be produced in well w1320.5 with an marker tag indicating FY265A and a source tag indicating the DNA sample originated from the well in the first row of column c1352. Thus, for the method 200 of FIG. 2 step (d) is performed for "d"=8.

For source tag sharing number "d"=32, added to the wells in r1353 of plate 1310.8, are allele-specific primers directed to the polymorphisms SC, DI(B/A), CO, and LW, with visual markers to indicate alleles for each of these polymorphisms (see table 1220 of FIG. 12A). The samples in wells in the row r1353 are then amplified so that if a DNA sample contains an allele, then an amplicon is produced with the marker tag and the source tag identifying the well from which the DNA sample originated. For example, if one of the samples in well w1320.7 contained allele SCI, that is allele "I" of polymorphism SC, then an amplicon would be produced in well w1320.7 with a marker tag indicating SCI and a source tag indicating the DNA sample originated from the well w1320.7. Thus, for the method 200 of FIG. 2 step (d) is performed for "d"=32.

In alternative embodiments, the samples in wells in the row r1353 are then amplified so that if a DNA sample contains an allele, then an amplicon is produced with the marker tag and no source tag since no source tag was added in step (b) (iii).

The method 200 of FIG. 2 continues with step (e) identifying said allele-specific second reaction products by interrogating said derived source tag and said marker tag of said products, and if the interrogating of the derived source tag and the marker tag indicate unambiguous results, then identifying said alleles of the plurality of polymorphic sites, otherwise if the interrogating of the derived source tag and the marker tag indicate ambiguous results, then disambiguating at least some of the ambiguous results to identify.

In alternative embodiments, step (e) comprises: (e) if "d" is less than the maximum_pool_size, identifying said allele-specific second reaction products by interrogating said allele-specific second reaction products comprising said derived source tag and said marker tag, and if the interrogating of said allele-specific second reaction products indicates unambiguous results, then identifying said alleles of the plurality of polymorphic sites, otherwise if the interrogating of said allele-specific second reaction products indicates ambiguous results, then disambiguating the ambiguous results, otherwise if "d" is equal to or greater than the maximum_pool_size then identifying said allele-specific second reaction products by interrogating said allele-specific second reaction products comprising said marker tag, and if the interrogating of said allele-specific second reaction products indicates unambiguous results, then identifying said alleles of the plurality of polymorphic sites, otherwise if the interrogating of said allele-specific second reaction products indicates ambiguous results, then disambiguating the ambiguous results.

For the source tag sharing number "d"=1, for the wells of rows r1344, microparticles are added to the wells. The microparticles comprise attached capture probes comprising the complement of the source tag and the complement for each of the marker tags identifying alleles of polymorphisms FY, GYPBS, DO-793, GYPA, JK, HbS173. See FIG. 6A for an example of the microparticles that may be used. Note that here there can be no ambiguity in the present embodiment as the DNA samples are not sharing source tags. Alleles are identified by visually distinguishing the microparticles and the marker tags to determine alleles, for example by determining the presence or absence of visual markers 1 and 2 for each microparticle species.

For source tag sharing number "d"=2, for the wells of rows r1348, microparticles are added to the wells, the microparticles comprising attached capture probes comprises the complement of the source tag and the complement for each of the marker tags identifying alleles of polymorphic sites LU, DO-323, and DO-350. Note that here, as discussed with reference to FIG. 11, an ambiguity may arise if the DNA samples share a source code, and the DNA samples do not contain the same homozygous combination of alleles (either "AA" or "aa" as represented in FIG. 11). Alleles are identified by visually distinguishing the microparticles and the marker tags to determine alleles, for example by determining the presence or absence of visual markers 1 and 2 for each microparticle type. If a microparticle is observed to give two colors, then the samples implicated may be disambiguated in a subsequent step, as described below.

For source tag sharing number "d"=8, for the wells of rows 1350, microparticles are added to the wells, the microparticles comprising attached capture probes comprising the complement of the source tag and the complement for each of the marker tags identifying alleles of polymorphic sites K and FY265. Note that here, as discussed with reference to FIG. 11, an ambiguity may arise if the DNA samples share a source code, and the DNA samples do not have the same homozygous combination of alleles (either "AA" or "aa" as represented in FIG. 11). Alleles are identified by visually distinguishing the microparticles and the marker tags to determine alleles, for example by determining the presence or absence of visual markers 1 and 2 for each microparticle type. If a microparticle is observed to give two colors, then the samples implicated may be disambiguated in a subsequent step, as described below.

For source tag sharing number "d"=32, for the wells of rows 1353, microparticles are added to the wells, the microparticles comprising attached capture probes comprising the complement of the source tag and the complement for each of the marker tags identifying alleles of polymorphic sites SC, DI (referred to as DI(B/A) in FIG. 13), CO, and LW. In the alternative embodiments, the microparticles comprise attached capture probes comprising the complement of each of the marker tags identifying alleles of polymorphic sites, and no capture probe for source tags as source tags were not added in step (b) (iii). Note that in both cases, as discussed with reference to FIG. 10, an ambiguity may arise if all the DNA samples share a source tag, and the DNA samples do not contain the same homozygous combination of alleles (either "AA" or "aa" as represented in FIG. 11). Alleles are identified by visually distinguishing the microparticles and the marker tags to determine alleles, for example by determining the presence or absence of visual markers 1 and 2 for each microparticle species. If a microparticle is observed to give two colors, then the samples implicated may be disambiguated in a subsequent step, as described below.

Thus an attribute profile of 384 blood samples is determined.

In some embodiments, one or more alleles with a determined source tag sharing number "d" may be binned into a lower source tag sharing number "d". For example, a source tag sharing number of 8 was determined for the K(1/2) of FIG. 12A. However, if K(1/2) was to be determined with DO-323, which was determined to have a source tag sharing number of 2, and no other alleles were to be determined, then a source tag sharing number of "d"=2 may be used for K(1/2) so that the method could be performed to determine K(1/2) and DO-323 in the same wells.

In some embodiments, a set of pre-assembled planar arrays of encoded microparticles may be used to identify alleles in method 200 instead of microparticles being added to the wells. Aliquots of the products of the identifying step of method 200 may be transferred from the wells of plate p1310.8 to positions, in this case, containing a pre-assembled planar array of encoded microparticles.

In some embodiments, electrophoresis may be used to identify the alleles. The design of the source and marker tags to enable identification with electrophoresis is discussed in more detail below.

The method 200 of FIG. 2 continues with if the interrogating of the derived source tag and the marker tag indicate ambiguous results, then disambiguating the ambiguous results. In some embodiments, the method 200 is repeated for the allele that indicated an ambiguous result with the source tag sharing number "d" reduced so that the number of nucleic acid samples in pools sharing a source tag is reduced. For example, if the method 200 is performed with the source tag sharing number "d"=8, and an ambiguity is detected at a polymorphic site for the 8 nucleic acid samples sharing a source code, then the method may be performed with the 8 nucleic acid samples with a source tag sharing number less than 8, for example d="1". Performing the method with the source tag sharing number d="1", for the eight nucleic acid samples for determining the allele at a polymorphic site, would mean that none of the nucleic acid samples would share a source tag so there would be no ambiguities and the method would determine the allele at the polymorphic site for each of the 8 nucleic acid samples. In some embodiments, if there is an ambiguity in determining an allele at polymorphic site for a group of nucleic acids samples, the source tag sharing number "d" may first be reduced to a lower source tag sharing number and the method performed with the lower source tag sharing number, and then if there is still an ambiguity the method may be performed again with an even lower source tag sharing number. This may repeat until the source tag sharing number is reduced to 1 in which case there are no ambiguities because nucleic acid samples do not share a source tag with a source tag sharing number=1. In some embodiments, other alleles to be identified may be identified with the alleles that were not identified and thus were ambiguous.

Figure 14:
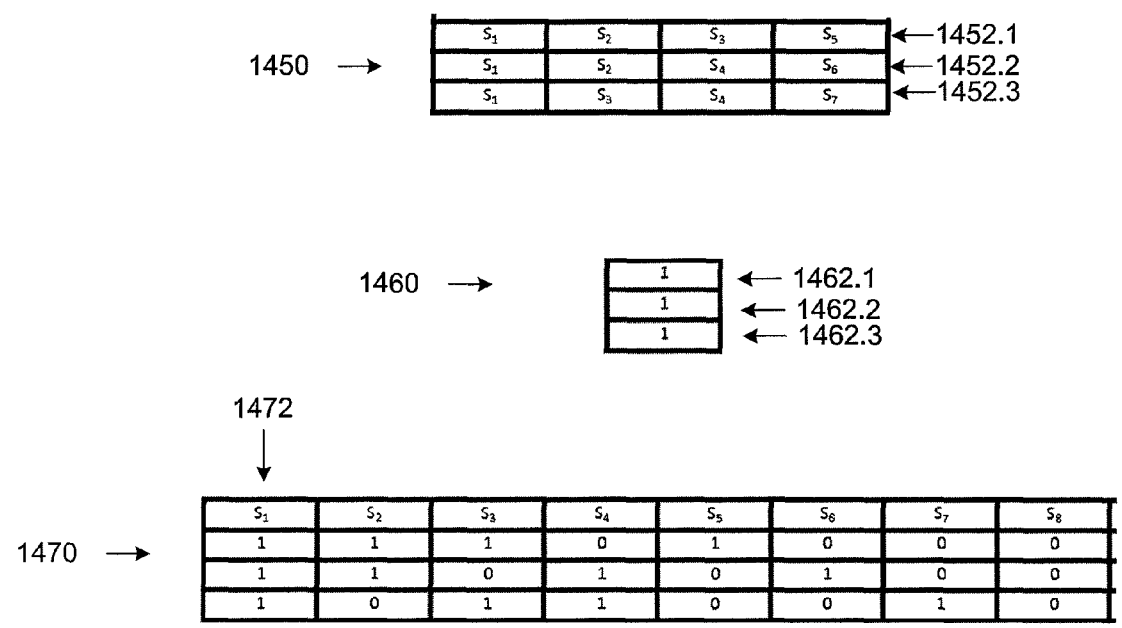
FIG. 14 schematically illustrates binary deconvolution for the case where "d"=8, when there is an ambiguity for a polymorphism with two alleles.

In some embodiments, a method of deconvolution may be used to disambiguate ambiguities arising from performing the method 200 of FIG. 2. Illustrated in FIG. 14 is an example of a method of deconvolution for the case with the source tag sharing number "d"=8, when there is an ambiguity in determining a polymorphism having two alleles. For example, the polymorphic site may be K(1/2) from table 1220 (of FIG. 12A) and the results in step (e) of method 200 may have indicated that at least one of the samples sharing a source tag contained the variant form of the allele at the polymorphic site (with a percentage frequency of 0.01 or 1%).

To disambiguate the results, three different operations are performed with different subsets of four of the eight samples sharing the same source tag, as illustrated in table 1450. The first operation 1452.1 in FIG. 14 pools $sample_1$, $sample_2$, $sample_3$, and $sample_5$, and then amplifies the pool with an allele-specific primer for the variant allele of K(1/2) to determine whether or not any of the samples contain the variant allele. The result is scores as either 0 or 1, and may be recorded in the table 1460. It is assumed for purposes of this example the result is a 1 and is recorded at 1462.1 of FIG. 14. Similarly, the second operation 1452.2 pools $sample_1$, $sample_2$, $sample_4$, and $sample_6$, and then amplifies the pool with an allele-specific primer for the variant allele of K(1/2) to determine whether or not any of the samples contain the variant allele. It is assumed for purposes of this example that the result is a 1 and is recorded at 1462.2 of FIG. 14. Similarly, the third operation 1452.3 pools $sample_1$, $sample_3$, $sample_4$, and $sample_7$, and then amplifies the pool with an allele-specific primer for the variant allele of K(1/2) to determine whether or not any of the samples contain the variant allele. It is assumed for purposes of this example that the result is a 1 and is recorded at 1462.3 of FIG. 14.

The sample that is positive for the variant allele K(1/2) can then be identified by examining table 1470 of FIG. 14. Table 1470 is a table constructed that identifies which of the samples contains the variant allele based on the results of the three operations performed above. Here, table 1460, with the single column of three 1's matches column 1472 of table 1470, which also has three 1's. Thus, $sample_1$ is the sample with the variant allele K(1/2). Note, that $sample_1$ is the sample that contains the variant allele because $sample_1$ is the only sample that was included in all three operations performed above and all three operations indicated the presence of the variant allele. However, it can not be conclusively determined that $sample_1$ contains the variant allele, because it may be that more than one sample contains the variant allele. In some embodiments, an additional operation may be perform on seven of the eight samples excluding $sample_1$. If the result of the operation indicates that none of the seven samples contains the variant allele, then the ambiguity has then been removed, and it is certain that $sample_1$ and only $sample_1$ of the eight samples contains the variant allele.

In some embodiments, step (b) of method 200 may be performed with for each of the plurality of sample containers for the source tag sharing number "d", contacting the nucleic acid samples contained in the sample container with probes, said probes comprising a source tag identifying the sample container, and elongating said probes to produce, in the sample container, amplicons from the nucleic acid samples, said amplicons comprising said source tag.

In some embodiments, step (d) of method 200 may be performed by contacting the amplicons in the pooling container for the source tag sharing number "d" with an allele specific hybridization probe comprising a marker tag for identifying the allele to produce an allele specific hybridization products, said allele specific products comprising said marker tag and said source tag.

In some embodiments, the number of alleles at the polymorphic site is greater than two.

In some embodiments, the source tags need only be unique for gDNA samples that are present in the same pool.

Some embodiments have the advantage of reducing the number of extraction and amplification operations when the source tag sharing number "d" is greater than 1. Additionally, the number of discrimination and detection operations is reduced from the traditional method which takes the number of samples for which the attribute profile is to be determined.

In some embodiments of the invention, ambiguities are encountered according to equation 2: Prob (ambiguity)=1−$f(N)^{m*d}$−$f(V)^{m*d}$, where m is the number of alleles for a polymorphism, and the reduction in the number of procedural steps may be estimated as follows, starting with the following expression for the expected number of steps ("tests"):

$$\text{Tests}=N/(2*d)+([1-(1-f(v))^{m*d}]*N/(m*d))*(m*d), \qquad \text{Equation 4}$$

where N is the number of samples. Minimization with respect to m*d for f(v)<<1, yields m*d=1/(√(f(v))). For example, f(v)=0.01, then m*d=10, and f(v)=0.001, then m*d=32. And, Tests(min)>=2*(√f(v))*N, and thus a reduction in the number of tests by a factor of 2*√f(v). For example, a five fold reduction in the number of tests for f(v)=0.01 and for f(v)=0.001 a 33 thirty-three fold reduction.

Some embodiments of the invention have the advantage of increasing the rate of "throughput" of allele determination. Source tags sharing between even 2 or 4 samples produce a significant reduction in the number of individual gDNA extractions and amplification steps while reducing the complexity. That is the number of amplicons simultaneously produced of the polymorphism amplification and discrimination by performing fewer polymorphism amplifications and discriminations per well.

The method described may have the advantage that it may be difficult to perform amplification for different polymorphisms either at the same time or sequentially because the parameters such as temperature and the contents of the well may vary depending on the polymorphism.

In some embodiments of the invention, the identifying step of method 200 is performed using microparticles comprising a complement source tag capture probe and a complement marker tag capture probe that is coded for both an allele and a specific polymorphic site. This embodiment is discussed above. One advantage of this embodiment is that the microparticles may be used in multiple wells or pools in the identifying step since the source tags and the marker tags may be shared between separate pools or wells.

Figure 15:
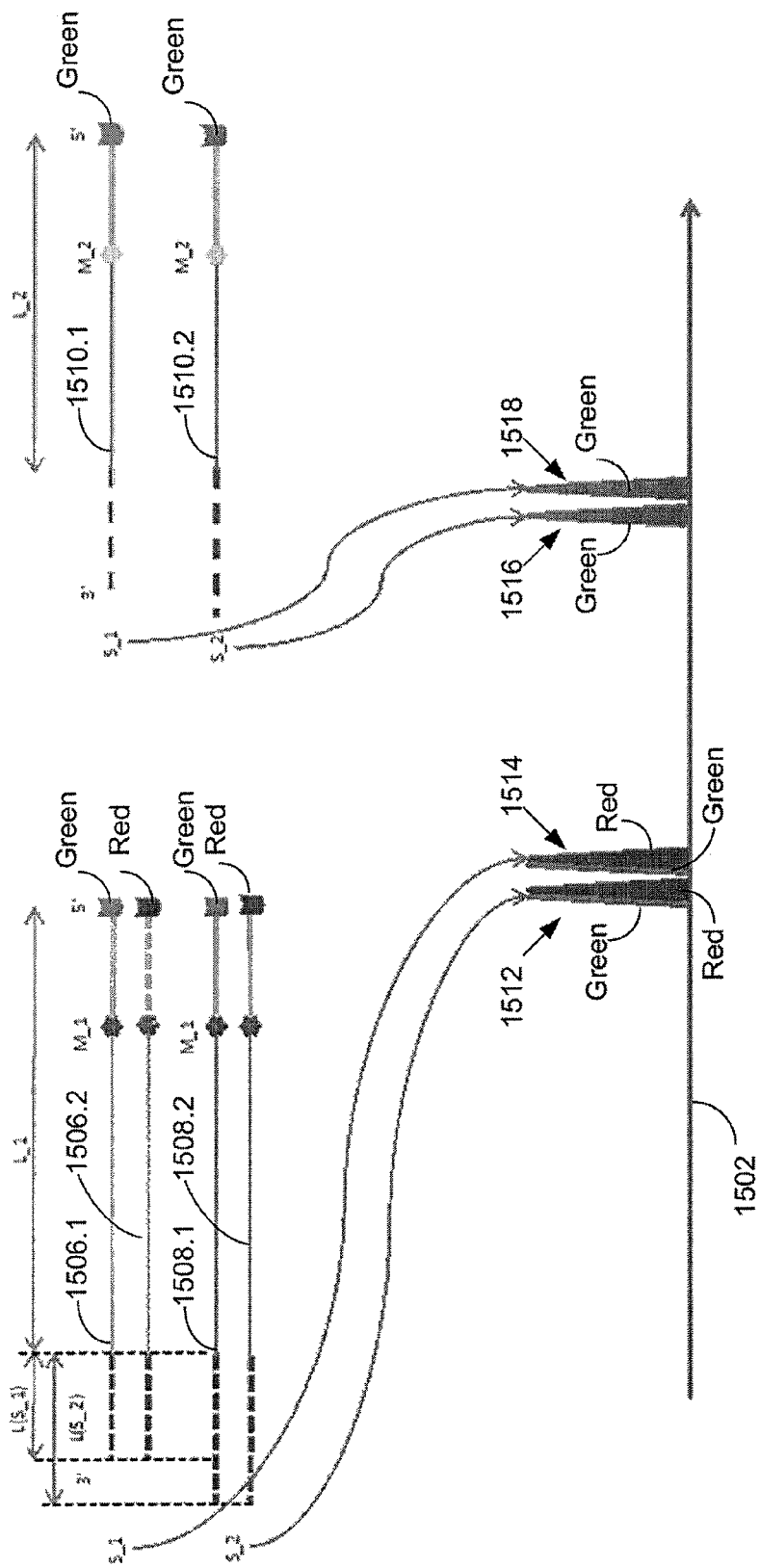
FIG. 15 schematically illustrates detection of products comprising specific combinations of source tags and marker tags by capillary electrophoresis.

In some embodiments of the invention, detection of hybridization or amplification products comprising source tags and marker tags may be accomplished by capillary electrophoresis, as illustrated in FIG. 15. Illustrated in FIG. 15 are six amplification products each comprising a source tag, labeled as either S_1 or S_2, and a marker tag, labeled as either M_1 or M_2. As illustrated, the differential electrophoretic mobility of amplicons of different length places a longer polynucleotide more to the left along the axis 1502 and the shorter polynucleotide more to the right. As illustrated, the amplicons 1506, 1508, 1510 comprise a fluorescent tag (red or green) so that the position along the axis 1502 can then be used to determine source tags and polymorphic sites. As illustrated the marker tags are the same length and the marker tag are distinguished by color, but different length marker tags could be used to distinguish between marker tags.

Since the total nucleotide sequence length (plus fluorescent tag) will determine where along the axis 1502 the fluorescence from the fluorescent tag can be detected, the following illustrates how to design hybridization or amplification products to enable them to be identified using electrophoretic separation.

In some embodiments, polymorphic sites may be distinguished by designing pairs of primers that produce different lengths of amplicons that include the polymorphic site that is being interrogated. For example, in FIGS. 15, 1506.1, 1506.2, 1508.1, and 1508.2 are all of the same length (number of nucleotides plus marker tag) L_1. So, this length L_1 may be used to identify one polymorphic site. Then a different length, L_2, may be used for 1510.1 and 1510.2 to identify a second polymorphic site. As illustrated in FIGS. 15, 1510.1 and 1510.2 are separated to the right of 1506 and 1508 due to the smaller size of L_2 compared with L_1. In one embodiment, no additional marker tag is used (that is, the length of the marker tag is zero), as no sequence-specific capture is required for electrophoretic detection.

The different source tags can then be distinguished by using different lengths for different source tags. As illustrated, S_1 is shorter than S_2 so the hybridization or amplification products including S_1 are to the right of the hybridization or amplification products that are the same except for comprising S_2. For example, 1510.1 and 1510.2 may represent the hybridization or amplification products for one allele determination from two different source samples. Both, 1510.1 and 1510.2 are green so for the purposes of this example we can assume that 1510.1 and 1510.2 indicate that the nucleic acid sample labeled with S_1 and S_2 has the Normal allele for the polymorphic site that is encoded with length L_2.

Illustrated in FIG. 15 is also 1506.1 and 1506.2 which are hybridization or amplification products with a length L_1 that encodes a different polymorphic site than L_2. In this case, since both 1506.1 and 1506.2 are generated, at least one of the nucleic acid samples encoded with S_1 is heterozygous for the polymorphic site encoded by L_1. Note that both the green and red signal can be distinguished at 1514.

Thus, by choice of amplicon length and source tag length, electrophoretic separation may be used to identify alleles for multiple source tags and for multiple polymorphic sites.

In some embodiments, allele-specific second reaction products are interrogated by differential melting curve analysis.

In some alternative embodiments, if "d"=maximum_pool_size and no source tags are applied then in a pool comprising "d"=maximum_pool_size samples, the method may perform step (d) by putting allele-specific primers for one or more of the alleles to be identified, with each N/V pair of allele-specific primers (possibly directed to different variable sites) fluorescently labeled with the same colors (e.g. "Green" for N, "Red" for V), but different allele-specific primers differing in length (for example by inclusion of a marker sequence tag) so that product length identifies the allele, and then performing PCR to produce allele-specific reaction products. In this alternative embodiment, step (e) comprises a screening step of detecting, in the pool, the presence of any "Red" signal indicating the presence of at least one sample having at least one variant allele, among the target alleles; and, if there are any "Red" signals then performing a length analysis of the allele-specific reaction products formed in order to determine the identify of the variant allele among the group of binned alleles. The colors "Red" and "Green" can be any two colors that are distinguishable.

A number of other techniques are available for nucleic acid analysis based upon nucleic acid length. One such method is denaturing gradient gel electrophoresis.

In some embodiments, source tags also may be modified to display "drag" tags to modulate electrophoretic mobility. For example, see Won et al., "Electrophoresis", 26(11): 2138-2148 (2005), the entire disclosure of which is incorporated herein by reference. In some embodiments, the marker tags may vary in length to encode source tag, polymorphic site, and allele. For example, a shorter marker tag with a green fluoresce may indicate the normal allele, and a longer maker tag with a green fluoresce may indicate the variant allele.

In some embodiments, the method of the invention can be used to identify alleles comprising epigenetic modifications. Nucleic acid samples comprising single-stranded DNA are first treated with sodium bisulfite to convert non-methylated cytosine residues to uracil residues. The bisulfite-treated sample is then subject to analysis as described herein. Methods for bisulfite conversion of non-methylated cytosine residues and subsequent methylation-specific PCR are described, for example, by Herman et al., Proc. Natl. Acad. Sci USA, 93(18):9821-9826 (1996), the entire disclosure of which is incorporated herein by reference.

In some embodiments of the method, where the source tag sharing number "d" determined for at least one allele is equal to maximum_pool_size, the method comprises identifying at least two alleles wherein there is at least one allele for which the source tag sharing number "d" is determined to be less than maximum_pool_size. In some embodiments of the method, where the source tag sharing number "d" determined for at least one allele of a first polymorphic site is equal to maximum_pool_size, the method comprises an allele at another polymorphic site for which the source tag sharing number "d" is determined to be less than maximum_pool_size.

In some embodiments of the method, the method comprises identifying at least two alleles, wherein the source tag sharing number "d" for a first allele is different from the source tag sharing number "d" for the at least second allele, and the source tag sharing number "d" is determined based on the frequency of the allele.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

Although described in connection with preferred embodiments thereof, it will be appreciated by those skilled in the art that additions, deletions, modifications, and substitutions not specifically described may be made without departure from the spirit and scope of the invention as defined in the appended claims.

What is claimed is:

1. A method of determining allele profiles by identifying alleles at one or more polymorphic sites, for at least two nucleic acid samples in a plurality of nucleic acid samples, the method comprising:

(a) binning one or more of the alleles to be identified based on the alleles to be binned having the same source tag sharing number "d",
wherein said source tag sharing number "d" is determined based on a frequency of the one or more alleles to be identified,
wherein if said number "d" is not an integer, then said number "d" is set to the closest positive integer that is less than "d";
provided that if "d" is less one, then "d" is set to one;
further provided that if the resulting integer "d" exceeds a preset upper limit of "d", it is replaced by said preset upper limit of "d", wherein said preset upper limit of "d" is the lesser of:
(i) a value of "d" determined by the condition that the probability of an ambiguity in the identification of said alleles occurring in "d" nucleic acid samples of the plurality of nucleic acid samples does not exceed a user-selected highest acceptable probability of an ambiguity in the identification of said alleles occurring in "d" nucleic acid samples of the plurality of nucleic acid samples;
provided that the user-selected highest acceptable probability of an ambiguity is not 0 or 1 and provided that the frequency of a variant allele based on the alleles to be identified is not 0; and
(ii) the maximum pool size, which is a number of nucleic acid samples that may be pooled, wherein the number is greater than one and is based on technical limitations of performing the steps of the herein method of determining allele profiles;

(b) collecting aliquots from the plurality of nucleic acid samples and combining "d" number of said aliquots to form at least one nucleic acid sample pool;

(c) performing a reaction in each nucleic acid sample pool to produce reaction products comprising a source tag identifying each said pool and polymorphic sites comprising said binned alleles, wherein said reaction is performed using as templates said nucleic acid samples in each said pool;

(d) if "d" is less than the maximum pool size, then forming at least one pooled pool comprising at least some of the said produced reaction products from a number of pools, said number determined as the result of dividing the maximum pool size by "d"; or if "d" is equal to the maximum pool size, then proceeding to step (e) without forming pooled pools;

(e) for each of the alleles to be identified, performing a second reaction in the at least one pool or pooled pool using said reaction products comprising said source tag to produce allele-specific second reaction products comprising a marker tag and a derived source tag, wherein said derived source tag is at least one of: said source tag, a copy of said source tag, or a copy of the complement of the source tag, and wherein said marker tag identifies an allele at a polymorphic site;

(f) interrogating said marker tags;

(g) (i) if the marker tags at a polymorphic site comprising the one or more alleles to be identified are identical, then identifying the nucleic acid samples identified by source tags or derived source tags as being homozygous for said allele of the one or more alleles to be identified;

(g) (ii) if the marker tags at a polymorphic site comprising one or more alleles to be identified are different, then identifying the polymorphic site with said different marker tags; and (h) for nucleic acid samples comprising polymorphic site(s) identified in (g) (ii), repeating steps (a)-(g) as needed on said identified nucleic acid samples until all of the alleles constituting the allele profile to be determined have been determined for each of the nucleic acid samples, wherein in carrying out repetitions of steps (a)-(g) "d" is replaced by an integer "d*" that is different than "d".

2. The method of claim 1, wherein in step (c) performing a reaction in a pool comprises: amplifying the nucleic acid samples in the pool with primers comprising a source tag, and wherein said reaction products comprise amplicons.

3. The method of claim 2, wherein said amplifying the nucleic acid samples comprises amplifying the nucleic acid samples by performing a polymerase chain reaction (PCR).

4. The method of claim 1, wherein in step (e) performing a second reaction comprises:

amplifying said reaction products with dye-labeled allele-specific primers using said reaction products as templates, and wherein said allele-specific second reaction products comprise dye-labeled allele-specific amplicons.

5. The method of claim 4, wherein said allele-specific amplicons indicate the identity of the allele of the allele-specific amplicon by a dye color or by a length of the allele-specific amplicon.

6. The method of claim 4, wherein said amplifying the nucleic acid samples comprises amplifying the nucleic acid samples by performing a polymerase chain reaction (PCR).

7. The method of claim 1, wherein step (g)(ii) further comprises:

performing a method of deconvolution for each allele that was not identified because the interrogating of said allele-specific products indicates ambiguous results.

8. The method of claim 1, wherein said marker tag of said second reaction products comprises at least one of the following to identify an allele: an oligonucleotide tag or a fluorescent tag.

9. The method of claim 1, wherein said marker tag of said second reaction products comprises an oligonucleotide tag comprising a first nucleotide sequence to identify an allele and wherein a second nucleotide sequence is linked to said marker tag to target a polymorphic site.

10. The method of claim 8, wherein said oligonucleotide tag comprises a nucleotide sequence to identify an allele of a polymorphic site, and wherein a second nucleotide sequence is linked to said marker tag to target a polymorphic site.

11. The method of claim 1, wherein said marker tag of said second reaction products comprises at least one of the following to identify a polymorphic site of the plurality of polymorphic sites: an oligonucleotide tag or a fluorescent tag.

12. The method of claim 1, wherein in step (f) interrogating comprises:

interrogating said derived source tag and said marker tag of said second reaction products by contacting said second reaction products with micro-particles, said micro-particles comprising a first capture probe complementary to said derived source tag and comprising an optical tag that identifies each first capture probe displayed on said micro-particle.

13. The method of claim 12, wherein said micro-particles further comprise a second capture probe complementary to said marker tag, and wherein said marker tag is an oligonucleotide tag.

14. The method of claim 12, wherein said marker tag comprises an optical tag.

15. The method of claim 14, wherein said optical tag is a fluorescent tag.

16. The method of claim 1, wherein in step (f) interrogating comprises:

interrogating said derived source tag and said marker tag of said second reaction products by electrophoretic separation of said second reaction products.

17. The method of claim 16, wherein the interrogating comprises determining a length of the second reaction products by electrophoretic separation.

18. The method of claim 16, wherein said marker tag comprises an optical tag.

19. The method of claim 16, wherein the source tag identifying said each pool or pooled pool encodes said each pool or pooled pool by a length of the source tag.

20. The method of claim 16, wherein the marker tag encodes an identity of a polymorphic site by a length of the marker tag.

21. The method of claim 16, wherein the identity of a polymorphic site for each sample in each said pool or pooled pool is encoded by the total length of said second reaction products.

22. The method of claim 16, wherein said second reaction products encode at least one of an allele or a polymorphic site.

23. The method of claim 1, wherein said source tag is an unique nucleotide sequence.

24. The method of claim 1, wherein said marker tag is an unique nucleotide sequence.

25. The method of claim 1, wherein said marker tag uniquely identifies an allele at a polymorphic site.

26. The method of claim 1 wherein said source tag sharing number "d" is determined using the following formula:

$$d=0.5*\log(1-C)/\log(1-f(V));$$

wherein C is said user-selected highest acceptable probability of an ambiguity and f(V) is the frequency of a variant allele.

27. The method of claim 1 wherein if the value of "d" is not a natural number of the form $2^n$, wherein n is a non-negative integer, then "d" is set to the nearest natural number of the form $2^n$ that is less than "d".

28. The method of claim 1 wherein the value of "d" is set to the closest integer less than or equal to the maximum pool size.

29. The method of claim 1 further comprising repeating steps (a)-(g) as needed with one or more additional alleles as the one or more alleles to be identified.

30. The method of claim 4, wherein said allele-specific amplicons indicate the identity of the polymorphic site giving rise to the allele-specific amplicon by a length of the allele-specific amplicon.

31. The method of claim 1, wherein the steps of interrogating marker tags and interrogating source tags or derived source tags are performed simultaneously.

* * * * *

```
                           SEQUENCE LISTING

<160> NUMBER OF SEQ ID NOS: 9

<210> SEQ ID NO 1
<211> LENGTH: 18
<212> TYPE: DNA
<213> ORGANISM: Artificial sequence
<220> FEATURE:
<223> OTHER INFORMATION: Created in silico

<400> SEQUENCE: 1
ccccatgtcg acatgaag                                                   18

<210> SEQ ID NO 2
<211> LENGTH: 18
<212> TYPE: DNA
<213> ORGANISM: Artificial sequence
<220> FEATURE:
<223> OTHER INFORMATION: Created in silico

<400> SEQUENCE: 2
cttcatgtcg acatgggg                                                   18

<210> SEQ ID NO 3
<211> LENGTH: 18
<212> TYPE: DNA
<213> ORGANISM: Artificial Sequence
<220> FEATURE:
<223> OTHER INFORMATION: Created in silico

<400> SEQUENCE: 3
ccccatgttg acgtgaag                                                   18

<210> SEQ ID NO 4
<211> LENGTH: 18
<212> TYPE: DNA
<213> ORGANISM: Artificial sequence
<220> FEATURE:
<223> OTHER INFORMATION: Created in silico

<400> SEQUENCE: 4
cttcacgtca acatgggg                                                   18

<210> SEQ ID NO 5
<211> LENGTH: 18
<212> TYPE: DNA
<213> ORGANISM: Artificial sequence
<220> FEATURE:
<223> OTHER INFORMATION: Created in silico

<400> SEQUENCE: 5
ccccatgttg acatgaag                                                   18
```

```
<210> SEQ ID NO 6
<211> LENGTH: 18
<212> TYPE: DNA
<213> ORGANISM: Artificial sequence
<220> FEATURE:
<223> OTHER INFORMATION: Created in silico

<400> SEQUENCE: 6
cttcatgtca acatgggg                                                 18

<210> SEQ ID NO 7
<211> LENGTH: 12
<212> TYPE: DNA
<213> ORGANISM: Artificial sequence
<220> FEATURE:
<223> OTHER INFORMATION: Created in silico

<400> SEQUENCE: 7
agctaacatg aa                                                       12

<210> SEQ ID NO 8
<211> LENGTH: 13
<212> TYPE: DNA
<213> ORGANISM: Artificial sequence
<220> FEATURE:
<223> OTHER INFORMATION: Created in silico

<400> SEQUENCE: 8
gtcgaaacat gaa                                                      13

<210> SEQ ID NO 9
<211> LENGTH: 13
<212> TYPE: DNA
<213> ORGANISM: Artificial sequence
<220> FEATURE:
<223> OTHER INFORMATION: Created in silico

<400> SEQUENCE: 9
gtcgcaacat gaa                                                      13
```